(12) United States Patent
Williams et al.

(10) Patent No.: US 9,017,966 B2
(45) Date of Patent: Apr. 28, 2015

(54) E. COLI PLASMID DNA PRODUCTION

(75) Inventors: James A. Williams, Lincoln, NE (US); Clague P. Hodgson, Omaha, NE (US); Aaron E. Carnes, Lincoln, NE (US)

(73) Assignee: Nature Technology Corporation, Lincoln, NE (US)

( * ) Notice: Subject to any disclaimer, the term of this patent is extended or adjusted under 35 U.S.C. 154(b) by 859 days.

(21) Appl. No.: 12/601,504

(22) PCT Filed: May 22, 2008

(86) PCT No.: PCT/US2008/006553
§ 371 (c)(1),
(2), (4) Date: Nov. 23, 2009

(87) PCT Pub. No.: WO2009/025690
PCT Pub. Date: Feb. 26, 2009

(65) Prior Publication Data
US 2010/0184157 A1    Jul. 22, 2010

Related U.S. Application Data

(60) Provisional application No. 60/931,465, filed on May 23, 2007.

(51) Int. Cl.
C12N 15/10 (2006.01)
C12N 1/06 (2006.01)

(52) U.S. Cl.
CPC .............. *C12N 15/1003* (2013.01); *C12N 1/06* (2013.01)

(58) Field of Classification Search
CPC ........ C12N 15/1003; C12N 1/06; C12N 15/63
See application file for complete search history.

(56) References Cited

U.S. PATENT DOCUMENTS

| | | | |
|---|---|---|---|
| 4,637,980 A | 1/1987 | Auerbach et al. | |
| 5,837,452 A | 11/1998 | Clark et al. | |
| 5,837,529 A | 11/1998 | Wan et al. | |
| 6,180,367 B1 | 1/2001 | Leung et al. | |
| 6,197,553 B1 | 3/2001 | Lee et al. | |
| 6,258,560 B1 | 7/2001 | Leung et al. | |
| 6,395,516 B1 | 5/2002 | Nienow et al. | |
| 6,455,287 B1 | 9/2002 | Jem | |
| 6,503,738 B1 | 1/2003 | Thatcher et al. | |
| 6,664,049 B1 | 12/2003 | Chevalier | |
| 6,699,706 B1 | 3/2004 | Brooks | |
| 2002/0197637 A1 | 12/2002 | Willson, III et al. | |
| 2006/0040393 A1 | 2/2006 | Jai et al. | |
| 2008/0138886 A1* | 6/2008 | Murphy et al. | 435/270 |
| 2010/0222558 A1* | 9/2010 | Gehant | 530/412 |

FOREIGN PATENT DOCUMENTS

| | | |
|---|---|---|
| EP | 0493926 A1 | 7/1992 |
| WO | 9816653 A1 | 4/1998 |
| WO | 9916869 A1 | 4/1999 |
| WO | 03046177 A1 | 6/2003 |
| WO | 2004022581 A1 | 3/2004 |
| WO | 2005026331 A2 | 3/2005 |
| WO | 2005078115 A1 | 8/2005 |
| WO | 2005097990 A1 | 10/2005 |
| WO | 2005098002 A1 | 10/2005 |
| WO | 2006023546 A2 | 3/2006 |
| WO | 2006026125 A2 | 3/2006 |
| WO | 2006060282 A2 | 6/2006 |
| WO | 2006073472 A2 | 7/2006 |
| WO | 2006083721 A2 | 8/2006 |
| WO | 2007035283 A1 | 3/2007 |

OTHER PUBLICATIONS

Li et al. "A set of UV—Inducible Autolytic Vectors for High Throughput Screening", Journal of Biotechnology 2007, vol. 127, p. 647-652.
Prather et al. "Industrial Scale Production of Plasmid DNA for Vaccine and Gene Therapy: Plasmid Design, Production, and Purification", Enzyme and Microbial Technology 2003, vol. 33, p. 865-883.
Salazar et al. "Enzymatic Lysis of Microbial Cells" Biotechnol. Lett. 2007, vol. 29, p. 985-994.
Walderich et al. "Induction of the Autolytic System of *Escherichia coli* by Specific Insertion of Bacteriophage MS2 Lysis Protein into the Bacterial Cell Envelope", Journal of Bacteriology Nov. 1988, vol. 170, No. 11, p. 5027-5033.
Willaims et al. "Generic Plasmid DNA Production Platform Incorporating Low Metabolic Burden Seed-Stock and Fed-Batch Fermentation Processes", Biotechnology and Bioengineering Aug. 2009, vol. 103, No. 6, p. 1129-1143.
Zhu et al. "A Continuous Thermal Lysis Procedure for the Large—Scale Preparation of Plasmid DNA", Journal of Biotechnology 2005, vol. 118, p. 257-264.
Carnes "Fermentation Design for the Manufacture of Therapeutic Plasmid DNA", Bioprocess Oct. 2005, p. 2-7.
Birnboim et al. "A Rapid Alkaline Extraction Procedure for Screening Recombinant Plasmid DNA", Nucleic Acids Research 1979, vol. 7, No. 6, p. 1513-1523.
Dabora et al. "Intracellular Lytic Enzyme Systems and Their Use for Disruption of *Escherichia coli*", Advances in Biochemical Engineering Jan. 1990, vol. 43, p. 11-30.
During "A Tightly Regulated System for Overproduction of Bacteriophage T4 Lysozyme in *Escherichia coli*", Protein Expression and Purification Academic Press Oct. 1993, vol. 4, No. 5, p. 412-416.

(Continued)

*Primary Examiner* — Michele K Joike

(74) *Attorney, Agent, or Firm* — Brooks Kushman P.C.

(57) ABSTRACT

General methods and strains of bacteria are described, that dramatically simplify and streamline plasmid DNA production. In one preferred embodiment, endolysin mediated plasmid extraction combined with flocculation mediated removal of cell debris and host nucleic acids achieves increased yield and purity with simplified downstream purification and reduced waste streams, thus reducing production costs.

14 Claims, 18 Drawing Sheets

(56) References Cited

OTHER PUBLICATIONS

Figure 1:
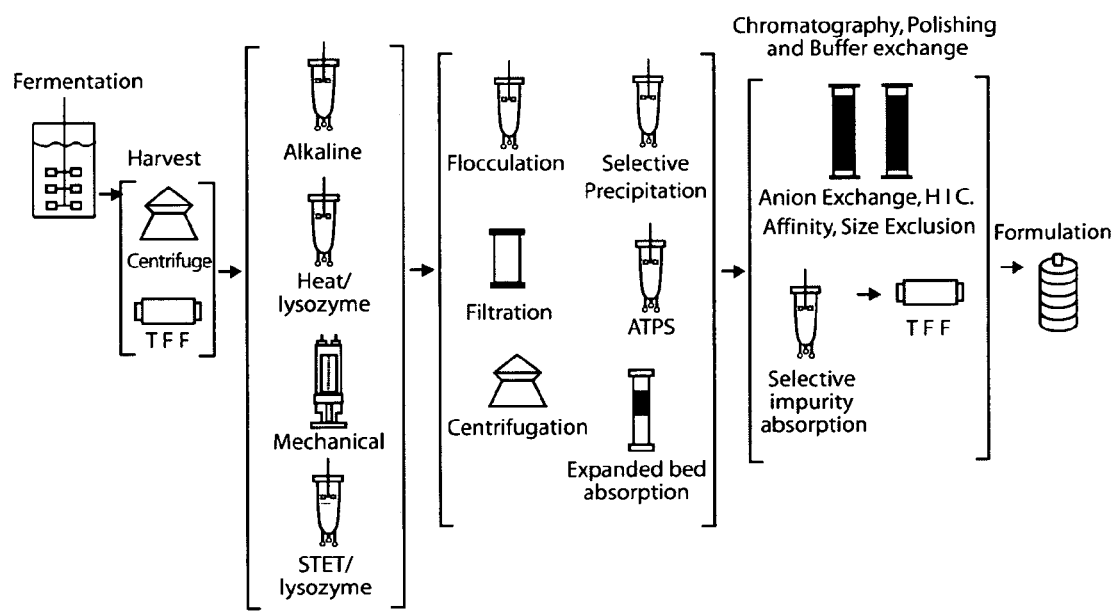

Lahihani et al. "High-Yield Production of pBR322-Derived Plasmids Intended for Human Gene Therapy by Employing a Temperature—Controllable Point Mutation", Human Gene Therapy Oct. 1996, vol. 7, p. 1971-1980.

Calvin et al. "High-Efficiency Transformation of Bacterial Cells by Electroporation" Journal of Bacteriology Jun. 1988, vol. 170, No. 6, p. 2796-2801.

Carnes et al. "Inducible *Escherichia Coil* Fermentation for Increased Plasmid DNA Production", Biotechnol. Appl. Biochem. 2006, vol. 45, p. 155-166.

Choe et al. "Direct Chemical Extraction of a Recombinant Viral Coat Protein from *Escherichia Coli* at High Cell Density", Biotechnology and Bioengineering Nov. 2001, vol. 75, No. 4, p. 451-455.

Ciccolini et al. "Time Course of SDS-Alkaline Lysis of Recombinant Bacterial Cells for Plasmid Release", Biotechnology and Bioengineering Dec. 1998, vol. 60, No. 6, p. 768-770.

Clewell et al. "Nature of col. E1 Plasmid Replication in *Escherichia Coli* in The Presence of Chloramphenicol" Journal of Bacteriology May 1972, vol. 110, No. 2, p. 667-676.

Clewell et al. "Properties of a Supercoiled Deoxyribonucleic Acid-Protein Relaxation Complex ad Strand Specificity of the Relaxation Event", Biochemistry 1970, vol. 9, No. 22, p. 4428-4440.

Cooke et al. "A Modified *Escherichia Coli* Protein Production Strain Expressing Staphylococcal Nuclease, Capable of Auto-hydrolysing Host Nucleic Acid", Journal of Biotechnology 2003, vol. 101, p. 229-239.

Crabtree et al. "Facile and Gentle Method for Quantitative Lysis of *Escherichia Coli* and *Salmonella typhimurium*", Journal of Bacteriology Apr. 1984, vol. 158, No. 1, p. 354-356.

Datsenko et al. "One-Step Inactivation of Chromosomal Genes in *Escherichia Coli* K-12 Using PCR Products" PNAS Jun. 2000, vol. 97, No. 12, p. 6640-6645.

Eon-Duval et al. "Precipitation of RNA Impurities With High Salt in a Plasmid DNA Purification Process: Use of Experimental Design to Determine Reaction Conditions" Biotechnology and Bioengineering Sep. 2003, vol. 83, No. 5, p. 544-553.

Evrard et al. "Histidine Modification and Mutagenesis Point to the Involvement of a Large Conformational Change in the Mechanism of Action of Phage Lambda Lysozyme", FEBS Letters 460, 1999, p. 442-446.

Ferreira et al. "Anion Exchange Purification of Plasmid DNA using Expanded Bed Adsorption", Bioseparation 2000, vol. 9, p. 1-6.

Guzman et al. "Tight Regulation, Modulation, and High-Level Expression by Vectors Containing the Arabinose P BAD Promoter", Journal of Bacteriology Jul. 1995, vol. 177, No. 14, p. 4121-4130.

Haldimann et al. "Conditional-Replication, Integration, Excision, and Retrieval Plasmid-Host Systems for Gene Structure-Function Studies of Bacteria", Journal of Bacteriology Nov. 2001, vol. 183, No. 21, p. 6384-6393.

Haskins et al. "Clone Unstable DNA by Lowering the Number of Common Vectors Using CopyCutter TMEPI400 TM *E.Coli* Cells*", Epicentre Forum 2004, vol. 11, p. 6-7.

Helander et al. "Polyethyleneimine is an Effective Permeabilizer of Gram-Negative Bacteria", Microbiology 1997, vol. 143, p. 3193-3199.

Hoare et al. "Bioprocess Engineering Issues that would be Faced in Producing a DNA Vaccine at up to 100 m 3 Fermentation Scale for an Influenza Pandemic", Biotechnol. Prog. 2005, vol. 21, p. 1577-1592.

Holmes et al. "A Rapid Boiling Method for the Preparation of Bacterial Plasmids", Analytical Biochemistry 1981, vol. 114, p. 193-197.

Horn et al. "Cancer Gene Therapy Using Plasmid DNA: Purification of DNA for human Clinical Trials", Human Gene Therapy May 1995, vol. 6, p. 565-573.

Jain et al. "Use of Lambda Phage S and R Gene Products in an Inducible Lysis System for Vibrio Cholerae- and *Salmonella enterica* Serovar Typhimurium-Based DNA Vaccine Delivery Systems", Infection and Immunity Feb. 2000, vol. 68, No. 2, p. 986-989.

Jensen et al. "Effect of Ionic Strength, pH, Amines and Divalent Cations on the Lytic Activity of T4 Lysozyme", Eur. J. Biochem. 1972, vol. 28, p. 116-122.

Jian-Xiao et al. "Interaction Mechanisms Between Anionic Surfactant Micelles and Different Metal Ions in Aqueous Solutions" Journal of Dispersion Science and Technology 2006, vol. 27, p. 1073-1077.

Joshi et al. "Production of DNA-Recombinant Polypeptides by Tac-Inducible Vectors Using Micromolar Concentrations of IPTG", BioTechniques 1993, vol. 14, No. 6, p. 886-887.

Kline et al. "Nonintegrated Plasmid—Chromosome Complexes in *Escherichia Coli*", Journal of Bacteriology Aug. 1976, vol. 127, No. 2, p. 881-889.

Kloos et al. "Inducible Cell Lysis System for the Study of Natural Transformation and Environmental Fate of DNA Released by Cell Death", Journal of Bacteriology Dec. 1994, vol. 176, No. 23, p. 7352-7361.

Love et al. "Stable High-Vopy—Number Bacteriophage λ Promoter Vectors for Overproduction of Proteins in *Escherichia Coli*", GENE International Journal on Genes and Genomes 1996, vol. 176, p. 49-53.

Makrides et al. "Strategies for Achieving High—Level Expression of Genes in *Escherichia Coli*", Microbiological Reviews Sep. 1996, vol. 60, No. 3, p. 512-538.

Manas et al. "Morphological and Physiological Changes Induced by High Hydrostatic Pressure in Exponential and Stationary—Phase Cells of *Escherichia Coli*: Relationship with Cell Death", Applied and Environmental Microbiology Mar. 2004, vol. 70, No. 3, p. 1545-1554.

Murphy "Use of Bacteriophage λ Recombination Functions to Promote Gene Replacement in *Escherichia Coli*", Journal of Bacteriology Apr. 1998, vol. 180, No. 8, p. 2063-2071.

Murphy et al. "A Limited Loss of DNA Compaction Accompanying the Release of Cytoplasm from Cells of *Escherichia Coli*", Journal of Structural Biology 2001, vol. 133, p. 75-86.

O'Mahony et al. "Integration of Bacteria Capture via Filtration and in Situ Lysis for Recovery of Plasmid DNA under Industry—Compatible Conditions", Biotechnol. Prog. 2007, vol. 23, No. 4, p. 895-903.

Paul et al. "Production of Extracellular Nucelic Acids by Genetically Altered Bacteria in Aquatic—Environment Microcosms", Applied and Environmental Microbiology Aug. 1989, vol. 55, No. 8. p. 1865-1869.

Pierson et al. "Development of *E. Coli* Host Strains Tolerating Unstable DNA Sequences on ColE1 Vectors", Focus 1999, vol. 21, No. 1, p. 18-19.

Prather et al. "Identification and Characterization of IS1 Transposition in Plasmid Amplification Mutants of *E. Coli* Clones Producing DNA Vaccines", Appl. Microbiol. Biotechnol. 2006, vol. 73, p. 815-826.

Rodriguez et al. "Precipitation in Solutions Containing Mixtures of Synthetic Anionic Surfactant and Soap. I. Effect of Sodium Octanoate on Hardness Tolerance of Sodium Dodecyl Sulfate", Journal of Surfactants and Detergents Jul. 1998, vol. 1, No. 3, p. 321-328.

Rodriguez et al. "Kinetics of Precipitation of Surfactants. I. Anionic Surfactants with Calcium and with Cationic Surfactants", Journal of Surfactants and Detergents Jan. 2001, vol. 4, No. 1, p. 1-14.

Saida et al. "Expression of Highly Toxic Genes in *E. Coli*: Special Strategies and Genetic Tools", Current Protein and Peptide Science 2006, vol. 7, No. 1, p. 47-56.

Shellman et al. "Introduction of Proteins into Living Bacterial Cells: Distribution of Labeled HU Protein in *Escherichia Coli*", Journal of Bacteriology May 1991, vol. 173, No. 10, p. 3047-3059.

Studier et al. "Use of Bacteriophage T7 Lysozyme to Improve an Inducible T7 Expression System", J. Mol. Biol. 1991, vol. 219, p. 37-44.

(56) References Cited

OTHER PUBLICATIONS

Theodossiou et al. "Design of Expanded Bed Supports for the Recovery of Plasmid DNA by Anion Exchange Absorption", Bioseparation 2001, vol. 10, p. 31-44.

Trinh et al. "An *Escherichia Coli* Strain for the Stable Propagation of Retroviral Clones and Direct Repeat Sequences", Focus 1994, vol. 16, p. 78-80.

Vaara et al. "Agents that Increase the Permeability of the Outer Membrane" Microbiological Reviews Sep. 1992, vol. 56, No. 3, p. 395-411.

Wicks et al. "Bacterial Lipoplysaccharide Copurifies with Plasmic DNA: Implications for Animal Models and Human Gene Therapy", Human Gene Therapy Mar. 1995, vol. 6, p. 317-323.

Zapf et al. "Calcium Surfactants: A Review", Advances in Colloid and Interface Science 2003, p. 348-380.

\* cited by examiner

E. COLI PLASMID DNA PRODUCTION

This application claims benefit of Provisional Patent Application Ser. No. U.S. 60/931,465 filed 23 May 2007

STATEMENT REGARDING FEDERALLY SPONSORED RESEARCH OR DEVELOPMENT

This invention was made in part with government support under Grant No. 2 R44 GM072141-02, awarded by the National Institutes of Health. The government has certain rights in this invention.

SEQUENCE LISTING

The text file is Autolysis_ST25.txt, created Nov. 23, 2009, and of size 10 KB, filed therewith, is hereby incorporated by reference.

FIELD OF THE INVENTION

The present invention relates to the production of covalently closed circular (ccc) recombinant DNA molecules such as plasmids, cosmids, bacterial artificial chromosomes (BACs), bacteriophages, viral vectors and hybrids thereof, and more particularly is methods for creating seed stocks, fermentation, cell lysis, and purification of plasmid DNA.

BACKGROUND OF THE INVENTION

The present invention relates to the production of covalently closed circular (ccc) recombinant DNA molecules. Such molecules are useful in biotechnology, transgenic organisms, gene therapy, therapeutic vaccination, agriculture and DNA vaccines.

With the invention in mind, a search of the prior art was conducted. E. coli plasmids have long been the single most important source of recombinant DNA molecules used by researchers and by industry. Today, plasmid DNA is becoming increasingly important as the next generation of biotechnology products (gene medicines and DNA vaccines) make their way into clinical trials, and eventually into the pharmaceutical marketplace. Plasmid DNA vaccines may find application as preventive vaccines for viral, bacterial, or parasitic diseases; immunizing agents for the preparation of hyper immune globulin products; therapeutic vaccines for infectious diseases; or as cancer vaccines.

Fermentation
Vector Backbones

Therapeutic plasmids typically contain a pMB1, ColE1 or pBR322 derived replication origin. Common high copy number derivatives have mutations affecting copy number regulation, such as rop (Repressor of primer gene) deletion, with a second site mutation that increases copy number (e.g. pMB1 pUC G to A point mutation, or ColE1 pMM1). Higher temperature (42° C.) can be employed to induce selective plasmid amplification with pUC and pMM1 replication origins.

Nature Technology Corporation fed-batch process:

Carnes, A E., Williams, J A 2006 World Patent Application WO2006023546 discloses methods for fed-batch fermentation, in which plasmid-containing E. coli cells are grown at a reduced temperature during part of the fed-batch phase, during which growth rate is restricted, followed by a temperature up-shift and continued growth at elevated temperature in order to accumulate plasmid; the temperature shift at restricted growth rate improves yield and purity of plasmid. This process takes advantage of the temperature sensitivity of high copy number plasmids. In the preferred process, the initial temperature setpoint is 30° C., at which the plasmid is maintained stably at low levels while biomass can accumulate efficiently. During this period, the specific growth rate is controlled at approximately $\mu=0.12$ $h^{-1}$ by an exponential feeding strategy. Induction of plasmid accumulation is performed when the cell density is in the range of 25-60 $OD_{600}$ by shifting the temperature to 42° C. and continued exponential nutrient feeding for up to 15 hours.

Plasmid yields prior to the temperature shift remain low. The specific plasmid yields after temperature shift are very high. Interestingly, after the temperature shift, the cells are able to tolerate significantly higher quantities of plasmid than cells grown at a constant temperature of 37° C. with the same media and feeding strategy.

The examples in the patent report yields up to 1.1 g/L achieved when the disclosed process was used with a temperature shift from 30° C. to 42° C. The preferred process of Carnes and Williams, Supra, 2006 is also described in Carnes, A E, Hodgson C P, Williams J A. 2006 Biotechnol Appl Biochem 45:155-66 where volumetric yields of 1.5-2.1 g/L, and specific yields as high as 43 mg plasmid/g dry cell weight (DCW) are reported. The plasmid DNA produced with the process is of a high quality, being 96% supercoiled or greater with no detectable deletion or other rearrangement. The method is simple, can be used with multiple pUC based backbones, and does not require prescreening of individual colonies for high producing cell lines. A key advantage of the inducible fed-batch process is that amplification of plasmid copy number after suitable biomass accumulation helps preserve quality and stabilize toxic plasmids, while maximizing yield. This is because selection pressure at the cellular level is reduced during the biomass accumulation phase by minimizing the growth rate difference between monomer containing cells and dimer, or rearranged plasmid or plasmid-free cells.

Fermentation Summary

High specific yields are very desirable since increased plasmid yield per gram of bacteria, or increased plasmid relative to genomic DNA (utilizing the Carnes and Williams, Supra, 2006 process, up to 75% of the total DNA in the cell at harvest is plasmid DNA) lead directly to higher final product purities. Further improvements in yield or increases in the percentage plasmid per total DNA would further decrease production cost, improve purity and simplify removal of genomic DNA (gDNA). Other fermentation processes for plasmid production are reviewed in Carnes et al., Supra, 2006, and Carnes A. E. BioProcess Intl 2005; 3:36-44, and are included herein by reference.

Cell Disruption—Plasmid Release

The E. coli biomass generated by a fermentation process must be lysed to release the plasmid DNA (pDNA). Cell disruption methods fall into two main categories:

| Physico-mechanical | Chemical |
| --- | --- |
| liquid shear | detergents |
| solid shear | osmotic shock |
| agitation with abrasives | alkali treatment |
| freeze-thawing | enzyme treatment |
| ultrasonication | |
| heat | |

The cell disruption method for plasmid isolation must be chosen such that minimal damage is inflicted on the pDNA product, and in most cases, it is also desired to avoid shearing of the host cell gDNA into smaller fragments that are more difficult to separate from pDNA. Thus, the methods available for plasmid purification are more limited compared to the harsher methods that are often used for purifying smaller molecules such as proteins. Ideally the method releases a high yield of intact plasmid, while limiting release of difficult to remove impurities such as gDNA.

Most of the above methods have been applied, either alone or combined, to pDNA purification. To date, the two most commonly used methods for pDNA recovery are alkaline lysis and heat lysis; additionally, detergents and enzyme (i.e. lysozyme) treatment are often used to aid heat lysis and other methods.

Alkaline Lysis

The standard alkaline lysis method of Birnboim H C, Doly J. 1979 *Nucleic Acids Res.* 7:1513-23 is well known and is widely used without restriction in molecular biology laboratories. Generally, a lysis time of five minutes has been used with the standard alkaline lysis method; longer times have been known to cause irreversible denaturation of pDNA. A study (Ciccolini L A, Shamlou P A, Titchener-Hooker N J, Ward J M, Dunnill P. 1998 *Biotechol Bioeng.* 60: 768-770) on the time course of standard alkaline lysis was performed by measuring viscosity of a lysis mixture as a function of time and by performing cell counts over a range of lysis times. The results indicate that for *E. coli* DH5α, complete cell lysis occurs after about 40 sec and complete denaturation of gDNA takes 80-120 sec after mixing with the lysis buffer. Longer reaction times were reported to lead to shear degradation of gDNA.

Thatcher D R, Hitchcock A, Hanak J A J, Varley D. 2003 U.S. Pat. No. 6,503,738 describe a method to determine the optimum lysis pH value, which is about 0.2 pH below the "irreversible alkaline denaturation value", defined as "the pH value at which no more than about 50% of the alkaline denatured pDNA fails to renature as determined by standard agarose gel electrophoresis". The optimum lysis value can be different for various plasmid/host strain combinations.

The patent landscape includes various methods and devices aimed at performing alkaline lysis at large scale. Insufficient mixing will result in local pH extremes, causing irreversibly denatured plasmid. Mixing that is too aggressive can damage the pDNA and fragment gDNA. At the laboratory scale, mixing is performed gently by hand. Hand mixing at larger scales is not possible because of the large volumes and lack of reproducibility from person to person. Thus, batch mixing in a mechanically agitated vessel is often used, but the viscous, non-Newtonian properties of the lysis mixture require some consideration. Nienow A W, Hitchcock A G, Riley G L. 2003 U.S. Pat. No. 6,395,516 discloses a specialized vessel design for mixing cell lysate that utilizes baffles, low power number impellers, feed lines, and monitoring the degree of lysis by measuring viscosity.

Continuous flow through devices have been employed as alternatives to the challenge of achieving complete, but gentle mixing of large lysis volumes in stirred tanks, and are perhaps more easily implemented in facilities that do not already contain specialized batch mixing equipment. Additionally, the lysis reaction time can be closely controlled by the residence time of tubing or pipe (e.g. as in Wan N C, McNeilly D S, Christopher C W. 1998 U.S. Pat. No. 5,837,529; Chevalier, M 2003 U.S. Pat. No. 6,664,049; Detraz N J F, Rigaut G. 2006 World Patent Application WO2006060282), or of the holding vessel (e.g. as in Brooks R C. 2004 U.S. Pat. No. 6,699,706) before the neutralization step.

Inline static mixers (motionless mixers) have long been used in industry and more recently have been applied for cell lysis. A static mixer is a cylindrical tube containing stationary mixing elements. The mixing elements are shaped and positioned to combine materials as they flow through the mixer. Wan et al, *Supra* 1998 describes the use of static mixers to achieve gentle mixing of a cell suspension with a lysis solution. Mixing of the cell suspension stream with the lysis buffer stream is completed rapidly and the degree of mixing and lysis time can be adjusted by the number of mixing elements, flowrate, and length. Neutralization may occur in a second static mixer.

Chevalier, *Supra*, 2003 claims mixing methods that use only tubing, without the static mixers; instead, smaller diameter tubing is used and flowrates are adjusted to cause homogeneous mixing for the desired contact time.

Detraz and Rigaut, *Supra*, 2006 discloses flow-through mixing devices consisting of a conduit through which the lysis solution flows, and an inlet, such as a nozzle, into the conduit in which the cell suspension is injected in either a counter-flow or co-flow direction.

Brooks, *Supra*, 2004 claims the use of fluidic vortex mixers for continuous flow-through lysis and neutralization. A vortex mixer is described by the patent as a cylindrical chamber with an axial outlet at the center of one end wall with two tangential inlets along the periphery. The dimensions of the mixer and the flowrates used are chosen so that the residence time in the mixers is much less that the time required for lysis (about 0.01-0.1 sec) so that the cell suspension and lysis solution are mixed completely. The cells can then react with the lysis solution after exiting the vortex mixer. In an example, the cells and lysis solution are mixed in a first vortex mixer, flow into a tank for completion of lysis, and then the mixture flows through an outlet of the tank where it is mixed with neutralization buffer in a second vortex mixer.

Blanche F, Couder M, Maestrali N, Gaillac D, Guillemin T. 2005 World Patent Application WO2005026331 discloses continuous alkaline lysis through the use of T tubes with lengths of turbulent flow (achieved by small diameter tubing) to rapidly mix the cell suspension and lysis solution, followed by a length of laminar flow (in larger diameter tubing) for incubation and time for lysis and denaturation without substantial agitation which would damage the plasmid and fragment gDNA. Neutralization solution may then be introduced continuously in a second T tube.

The above flow-through mixing devices enable low shear mixing. It has been generally recognized that shear forces created by mixing too intensely may cause damage to pDNA and fragmentation of gDNA, leading to co-purification of gDNA with pDNA (Horn N A, Meek J A, Budahazi G, Marquet M. 1995 *Hum. Gene Ther.* 6: 565-573).

Alternative Lysis Methods

Heat Lysis

Plasmid isolation using heat lysis was first reported by Holmes D S, Quigley M. 1981 *Anal Biochem* 114:193-7, and is perhaps the most widely used method after alkaline lysis.

Merck has developed and patented processes to adapt heat lysis to large scale processing. In Lee, Ala., Sagar, S. 2001 U.S. Pat. No. 6,197,553, a bacterial suspension in modified STET buffer (e.g. 50 mM Tris, 50-100 mM EDTA, 8% sucrose, 2% Triton X-100, pH 8.0-8.5) with a density of about 30 $OD_{600}$ is pumped through a heat exchanger at such a rate that the suspension exits with a temperature of 70-100° C., resulting in lysis. The lysate is then centrifuged to pellet large cell debris, protein, and gDNA, leaving RNA and plasmid in solution. The optional use of lysozyme is reported to increase the plasmid concentration in the lysate by 4-5 times. It was also determined that the formation of undesirable open circle plasmid by endogenous DNase during this lysis process could be reduced by increasing the EDTA concentration from 50 mM to 100 mM. They report higher plasmid recovery than by chemical lyses.

A similar process is described by Zhu K, Jin H, Ma Y, Ren Z, Xiao C, He Z, Zhang F, Zhu Q, Wang B. 2005 *J Biotechnol.* 118: 257-264, which reports to have made improvements on the heat lysis methods of Holmes and Quigley, *Supra*, 1981, and Lee and Sagar, *Supra*, 2001. In this protocol, cell paste is resuspended with 10 mM Tris, 50 mM EDTA, pH 8.0 to a density of 100 $OD_{600}$ and treated with 0.1M NaCl, 2% Triton X-100, and lysozyme at 37° C. for 20 minutes. The cell suspension is then pumped through a copper coil immersed in a 70-80° C. water bath with a residence time of 20 sec, then it enters another copper coil immersed in an ice bath.

Mechanical Disruption

Generally, mechanical disruption of bacteria (e.g. french press, sonication, homogenization, nebulization) for plasmid isolation is seen as unfeasible due to the damage it would cause to the DNA. Jem K J. 2002 U.S. Pat. No. 6,455,287 reports that sonication, nebulization, and Gaulin Mill homogenization resulted in almost complete destruction of pDNA. However, disruption with a bead mill device under optimized conditions resulted in over 90% of the plasmid solubilized without destruction. They also report that an impinging-jet homogenizer released up to 50% of the pDNA intact.

Another method used to overcome destruction of DNA during mechanical disruption is the use of DNA compaction agents. Wilson R C, Murphy J C. 2002 US Patent Application US2002197637 disclose the use of polycationic compaction agents (e.g. polylysine, spermine, spermidine) to protect DNA from shear damage during mechanical lysis. The compaction agents cause the DNA to be pelleted with the insoluble cell debris. The pellet is washed, and the pDNA is resolubilized to give an enriched solution. The use of compaction agents also results in reduced lysate viscosity.

Lysozyme Lysis

A process developed by Merck (Boyd D B, Kristopeit A J, Lander R J, Murphy J C, Winters M A. 2006 World Patent Application WO2006083721) describes a STET/lysozyme lysis performed at 20° C. or 37° C., preferably with an additional alkaline pH shift to denature gDNA. While the process retains the pH shifting of alkaline lysis, shear forces are reduced by performing the shift after lysis. Therefore this process does eliminate many of the difficult processing and equipment needs of alkaline or heat lysis. The limitation of this reduced temperature lysis method is the need for large amounts of recombinant lysozyme.

Autolysis

Autolytic strains using phage T4 lysis proteins have been patented for protein production as in Leung W S, Swartz J R. 2001 U.S. Pat. No. 6,258,560. In this system, lysozyme (endolysin) is expressed by the cell in the cytoplasm and released to the periplasm at the desired time by co-expression of a holin (membrane spanning peptide or protein) that creates a channel, allowing leakage of lysozyme from the cytoplasm to the periplasm. Other autolytic *E. coli* strains that are described in Jia X, Kostal J, Claypool JA. 2006 US Patent Application US20060040393 contain the bacteriophage λR lytic endolysin gene. The endolysin is induced by arabinose, which then causes the *E. coli* to be lysed after a freeze-thaw cycle.

Autolysis conditions, as opposed to alkaline or heat lysis, do not selectively denature gDNA. The product of lysis is very viscous due to high levels of residual gDNA, creating processing problems. For protein production, non specific nucleases (e.g., Benzonase®) are added, or expressed periplasmically in the strain [e.g., endA or *Staphylococcus* nuclease (Cooke G D, Cranenburgh R M, Hanak J A J, Ward J M. 2003 *J Biotechnology* 101: 229-239)] to reduce viscosity after cell lysis. Such systems could not be utilized for plasmid production, since the plasmid would be degraded or damaged by the nuclease. While autolysis is not an essential design improvement for protein production (since cell lysis is performed at high density using generally available equipment) it has tremendous potential for plasmid purification since alkaline or heat lysis steps are key bottlenecks in plasmid processing.

Bacteriophage T5 exonuclease is an ideal DNase to use in plasmid processing. T5 exonuclease does not digest supercoiled plasmid, but is able to digest linear single- and double-stranded DNA (ssDNA, dsDNA). It will also digest DNA with denaturation loops, such as 'ghost' or 'shadow band' DNA, which often retains biological activity and is refractile to restriction enzyme digestion. Williams J A, Hodgson C P. 2006 World Patent Application WO2006026125 describe plasmid purification using *E. coli* strains expressing plasmid-safe nuclease (chimeric ribonuclease-T5 exonuclease genes) in combination with endolysin/holin pairs for autolysis.

Cell Disruption Summary

While the basic methods for obtaining plasmids (by bacterial fermentation), and for their purification (e.g., by heat or alkaline lysis) are well-known, and large scale manufacturing methods have been developed, these processes are problematic for transfer to new facilities due to specialized equipment needs, scaling issues, and tremendous lysis volumes. As well, they add excessive additional cost to the production of plasmids through reduced capacity, increased wastestreams, and expensive equipment and reagents. These limitations place a cost burden on commercialization of pDNA production processes. A new technology is needed to eliminate this critical processing bottleneck.

DISCLOSURE OF THE INVENTION

One embodiment of the invention is methods for production of plasmid DNA, using host strains in which a peptidoglycan hydrolase gene is inserted into the bacterial genome and expressed during production. After a plasmid or DNA replicon is grown in the cells, the peptidoglycan hydrolase is released from the cytoplasm, digesting the bacterial cell wall.

In one preferred embodiment, autolysis, peptidoglycan hydrolase digestion of the cell wall is utilized to effect cell lysis (autolysis process). In a preferred embodiment, peptidoglycan hydrolase expressing cells are used as an endogenous source of lysozyme in standard heat or lysozyme/STET lysis methods. In a preferred embodiment, cell lysis is modified from standard alkaline or heat lysis methods to lysis with a single solution containing concentrations of flocculating agents and salts that allows: 1) plasmid to be released from the cells and become soluble in the lysis solution and; 2) bacterial gDNA removal by its insolubility in the lysis buffer. In a preferred embodiment, the resulting liquid lysate containing pDNA is purified in a downstream process. In a preferred embodiment, after removal of cell debris and insoluble gDNA and other impurities, the pDNA is recovered by precipitation through the addition of more salt.

In an alternative preferred embodiment, extraction, peptidoglycan hydrolase digestion of the cell wall is utilized to permeabilize cells to affect plasmid release without complete lysis of the cell or extensive extraction of gDNA. In one preferred embodiment, the extraction process is performed by resuspension of peptidoglycan hydrolase containing cells in a buffer containing Triton X-100 and EDTA and/or polyethyleneimine at a slightly acid pH (low pH extraction process). In a preferred embodiment, extracted cells are flocculated by heat treatment and removed by filtration. In a preferred embodiment, plasmid present in the liquor after removal of extracted cells is purified in a downstream process.

In one preferred embodiment, the peptidoglycan hydrolase is a bacteriophage endolysin. In another preferred embodiment, the endolysin is the bacteriophage lambda gene R protein. In yet another preferred embodiment, the endolysin is the bacteriophage T4 gene e protein. In yet another preferred embodiment, the endolysin is the bacteriophage T7 lysozyme protein. In yet other preferred embodiments, the endolysin is a combination of endolysins, such as phage T4 (gene e) and phage lambda (lambdaR) endolysin proteins.

In yet another preferred embodiment, methods for producing peptidoglycan hydrolase in cells are disclosed, using host strains in which a peptidoglycan hydrolase gene is inserted into the bacterial genome or F plasmid, and selectively expressed during production. In a preferred embodiment the integrated peptidoglycan hydrolase is cloned downstream of a heat inducible promoter and selectively expressed during production by heat induction. In yet another preferred embodiment, the heat inducible promoter is the bacteriophage lambda pR and/or pL promoter(s) regulated by the C1857 temperature sensitive lambda repressor.

In yet another preferred embodiment, methods for improving fermentation yield and quality are disclosed, wherein fermentation cells are held at reduced temperature post production. In a preferred embodiment, the culture is held at 25-30° C. for 0.5 to 2 hrs post plasmid production prior to harvesting.

In yet another preferred embodiment, methods for improving plasmid yield and cell line viability are disclosed, wherein bacterial seed stocks are made at reduced temperature prior to cryopreservation. In a preferred embodiment, seed stocks are manufactured by growth of cells at 25-30° C. during production.

BRIEF SUMMARY OF THE INVENTION

It is a purpose and/or objective of the present invention to provide compositions of matter and processes for plasmid production. Another objective of the invention is to provide methods to reduce nucleic acid impurities, such as RNA and genomic DNA, in purified pDNA. Yet another objective of the invention is to reduce production costs for pDNA purification. Yet another objective and/or purpose of the invention is to reduce toxic waste in pDNA purification. Another objective of the invention is improved plasmid production processes that, compared to processes defined in the art, are improved by: increased quality of plasmid by reduced levels of nicked (open circular) or linearized versions of the plasmid; simplified production using robust production steps in dramatically reduced process volumes; simplified production through elimination of multiple production steps; reduced cost through elimination of multiple production steps and reduction of process volumes; reduced cost through elimination of expensive reagents currently utilized in cell lysis; increased quality of plasmid by reduction of nucleic acid impurities after plasmid purification due to elimination of key contaminants prior to entry into downstream processing; improved regulatory compliance by elimination of gDNA from final plasmid preparations; and improved regulatory compliance by elimination of toxic waste streams.

Further objects and advantages of the invention will become apparent from a consideration of the drawings and ensuing description.

BRIEF DESCRIPTION OF THE DRAWING FIGURES

FIG. 1. Plasmid production flowchart
FIG. 2. Application of various embodiments of the invention in plasmid production
FIG. 3. Plasmid extraction
FIG. 4. Overview of the inducible fed-batch fermentation process
FIG. 5. Plasmid quality analysis of samples from an inducible fed-batch fermentation.
FIG. 6. pAH144 heat inducible overexpression vectors
FIG. 7. STET cell suspensions
FIG. 8. Agarose gel analysis of clarified lysates
FIG. 9. Agarose gel analysis of PEG clarified lysates
FIG. 10. Agarose gel analysis of PNL clarified lysates
FIG. 11. Agarose gel analysis of samples from a purification of pDNA using autolysis and filter membranes
FIG. 12. Agarose gel analysis of samples from a purification of pDNA using autolysis and a non-chromatographic process
FIG. 13. Effects of salt concentration, extraction time, Triton X-100, and PEG8000 on plasmid extraction from autolytic cells
FIG. 14. Effect of pH and sodium acetate concentration on plasmid extraction. Agarose gel analysis
FIG. 15. low pH extraction of various plasmids, with or without endolysin, is shown
FIG. 16. Substitution of lysozyme for endolysin in low pH extraction is shown
FIG. 17. Improved solid liquid separation by thermal flocculation of an autolytic extraction mixture
FIG. 18. Improved plasmid quality by thermal flocculation of an autolytic extraction mixture
Table 1: Process hold step post 42° C. increases plasmid yield
Table 2: Seed stock preparation at reduced temperature increases plasmid yield
Table 3: Autolysis using Endolysin expressing cell lines
Table 4: Extraction of pDNA from endolysin containing cells using acetate solutions
Table 5: Protein extraction
Table 6: EDTA versus PEI extraction efficiency
Table 7: SDS-Calcium conditioning of a plasmid extract to remove RNA
Table 8: Thermal treatment

DETAILED DESCRIPTION OF THE INVENTION

Turning now to the drawings, in FIG. 1., a flowchart of plasmid production is shown.

Figure 2:
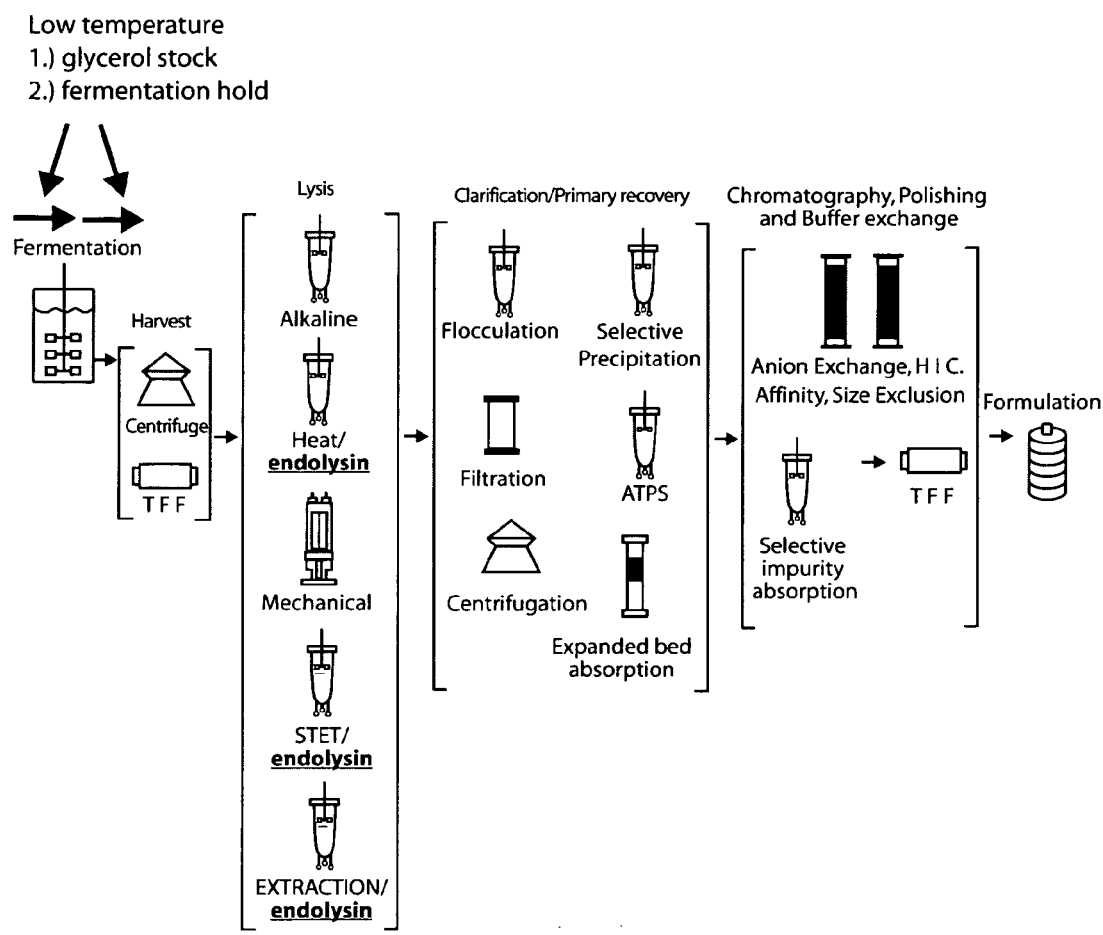

In FIG. 2., the plasmid production flowchart is modified to highlight improvements to specified steps by various embodiments of the invention.

Figure 3:
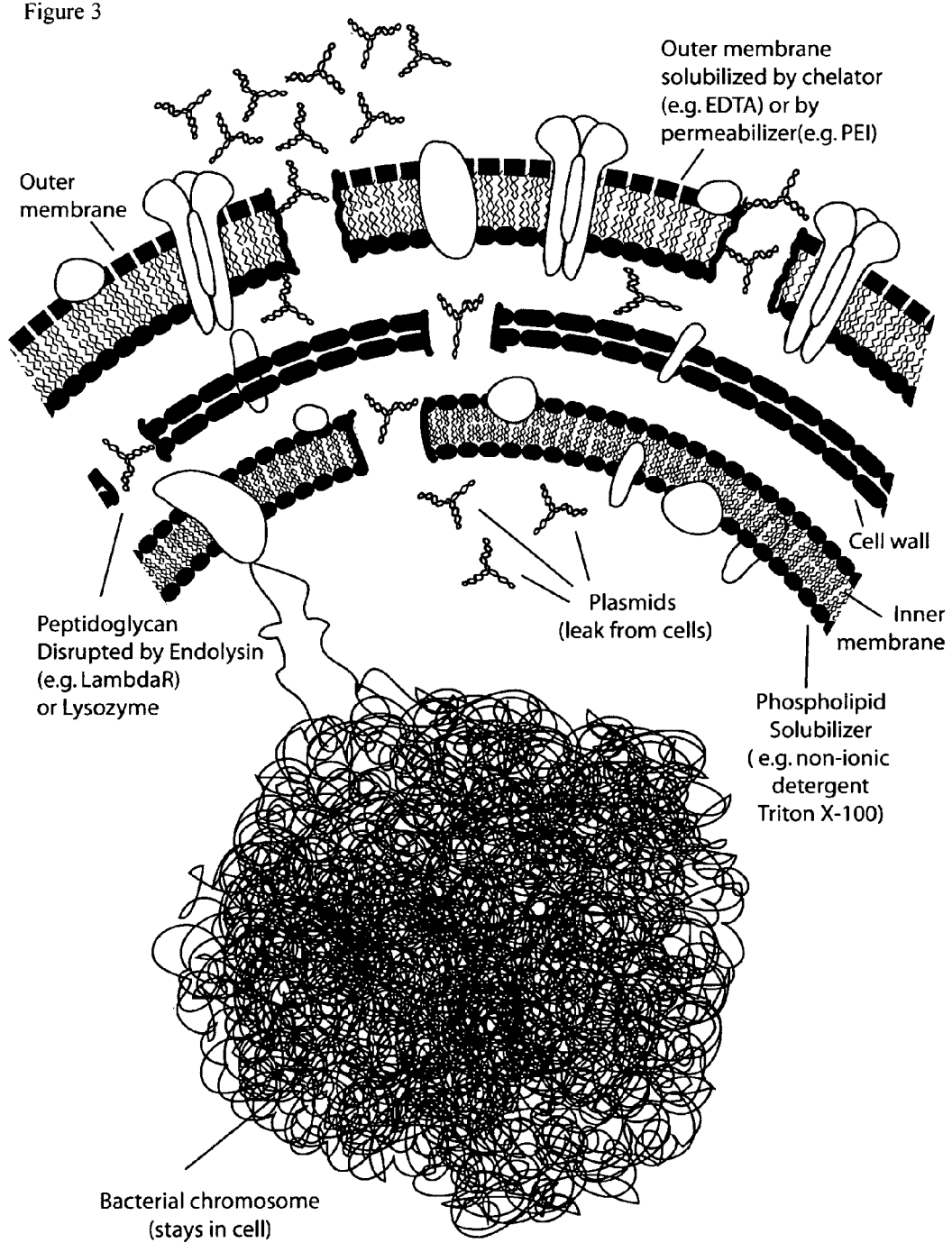

In FIG. 3., the structure of an *E. coli* cell is shown, highlighting various barriers to plasmid extraction, and example chemical or enzyme treatments that permeabilize each barrier.

Figure 4:
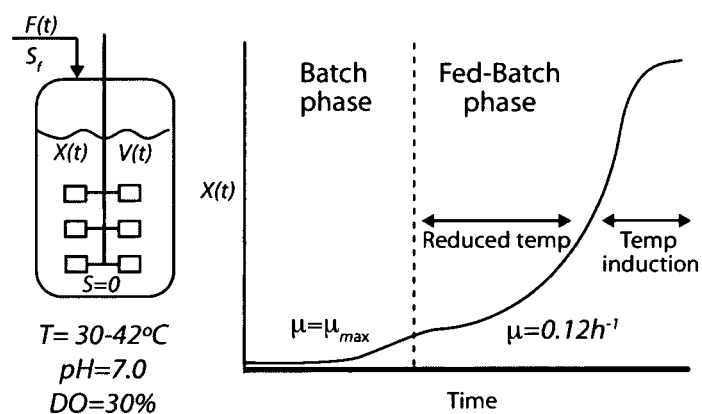

In FIG. 4., the inducible fed-batch fermentation of Carnes and Williams, *Supra*, 2006 is shown, in which plasmid-containing *E. coli* cells are grown at a reduced temperature during part of the fed-batch phase, during which time growth rate is restricted, followed by a temperature up-shift and continued growth at elevated temperature in order to accumulate plasmid.

Figure 5:
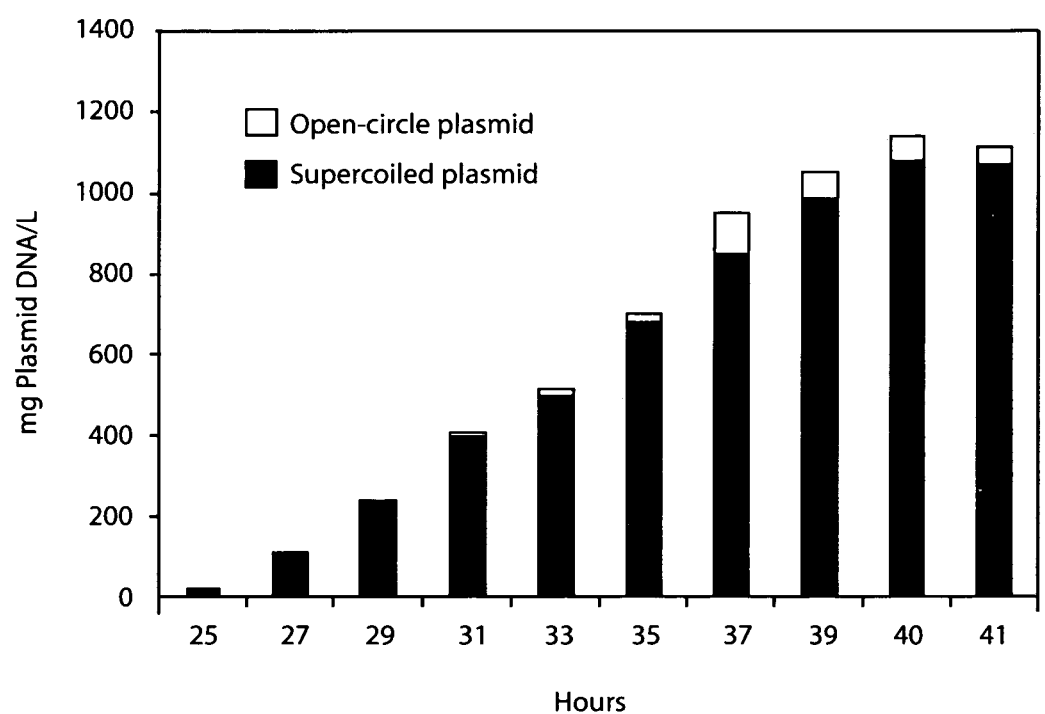
Figure 6A:
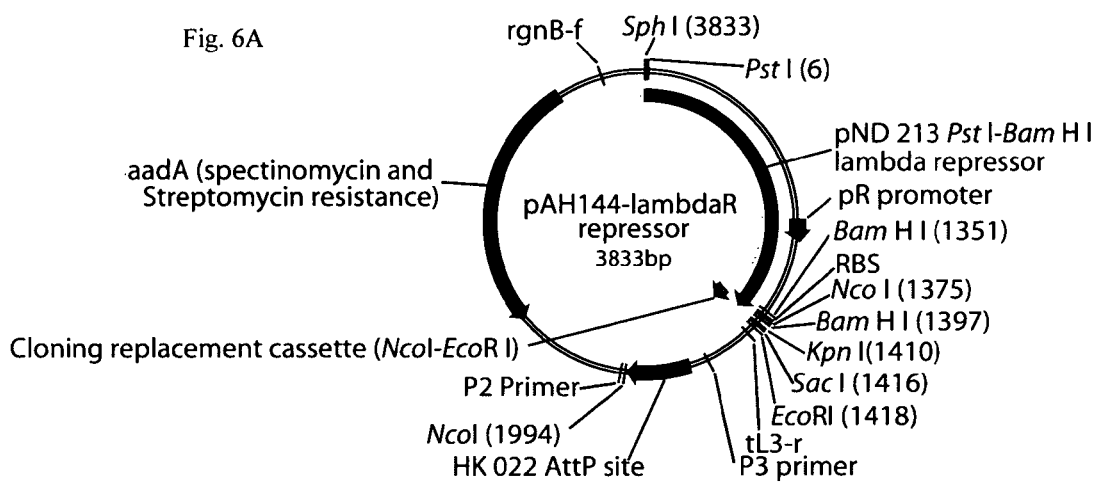
Figure 6B:
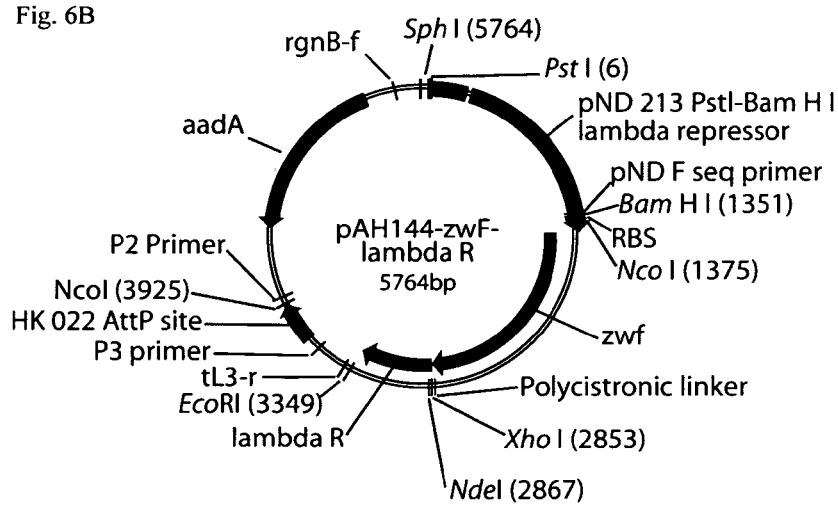
Figure 6C:
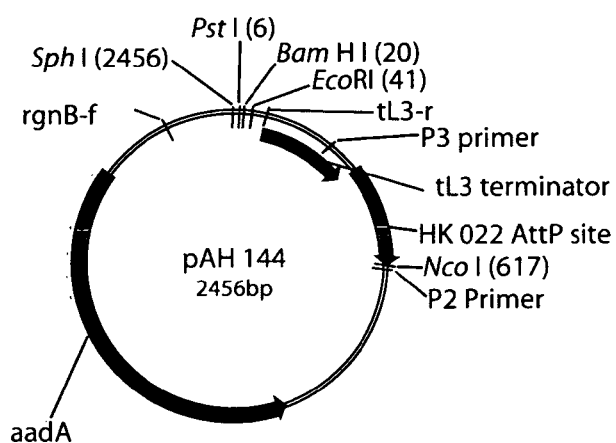

In FIG. 5., Plasmid quality analysis over the course of an inducible fed-batch fermentation is shown. Plasmid production was induced from 30° C. to 42° C. at 25 hrs. Induction was for 14 hrs (25-39 hrs) followed by a 2 hr hold at 25° C. The ratio of supercoiled to open-circle plasmid was determined with the PlasmidSelect Xtra Screening Kit (GE Healthcare, Uppsala, Sweden). The supercoiled plasmid purity in the final sample (41 hours) after a 2 hr hold at 25° C. is 96%.

In FIG. 6., maps of the pAH144 zwf-lambdaR heat inducible overexpression vector, and selected precursors, are shown.

Figure 7:
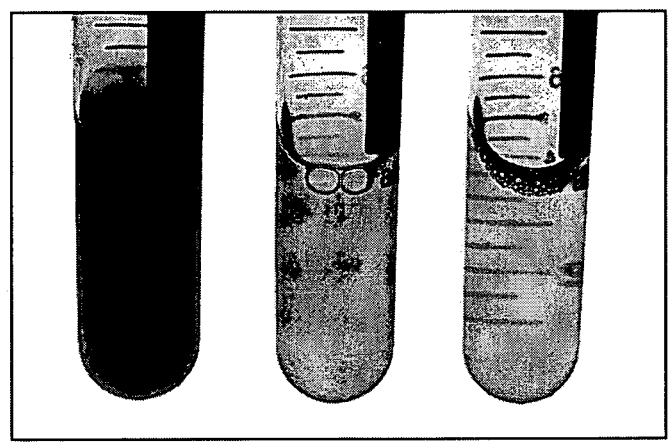

In FIG. 7., three STET cell suspension aliquots after aging 30 minutes at room temperature are shown.

Figure 8:
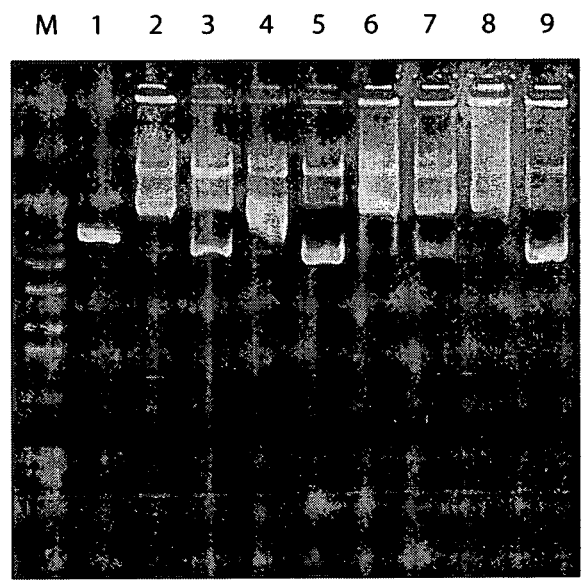

In FIG. 8., agarose gel analysis of clarified lysates using lysis solutions containing glucose and/or Triton X-100 and EDTA are shown. Endolysin containing fermentation cells carrying a high copy DNA vaccine plasmid were utilized in autolysis. Lanes: M) 1 kb DNA ladder (Invitrogen, Carlsbad CA); 1) a miniprep sample of the plasmid; 2) autolysis with 0.04% Triton X-100, 1 mM EDTA, 0% glucose; 3) autolysis with 0.04% Triton X-100, 50 mM EDTA, 0% glucose; 4) autolysis with 0.04% Triton X-100, 1 mM EDTA, 8% glucose; 5) autolysis with 0.04% Triton X-100, 50 mM EDTA, 8% glucose; 6) autolysis with 2% Triton X-100, 1 mM EDTA, 0% glucose; 7) autolysis with 2% Triton X-100, 50 mM EDTA, 0% glucose; 8) autolysis with 2% Triton X-100, 1 mM EDTA, 8% glucose; 9) autolysis with 2% Triton X-100, 50 mM EDTA, 8% glucose.

Figure 9:
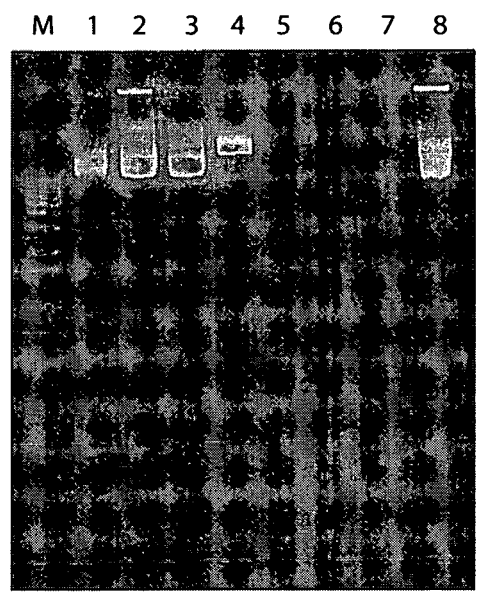

In FIG. 9., agarose gel analysis of clarified lysates using lysis solution containing PEG and different amounts of NaCl are shown. Endolysin containing fermentation cells carrying a high copy DNA vaccine plasmid were utilized in autolysis. Lanes: M) 1 kb DNA ladder; 1) Standard: 200 ng purified plasmid; 2) Supernatant of autolysis with 7.5% PEG-8000, 50 mM Tris pH 8.0, 10 mM EDTA, 1% Triton X-100; 3) Supernatant of autolysis with 7.5% PEG-8000, 50 mM Tris pH 8.0, 10 mM EDTA, 1% Triton X-100+0.1M NaCl; 4) Supernatant of autolysis with 7.5% PEG-8000, 50 mM Tris pH 8.0, 10 mM EDTA, 1% Triton X-100+0.2M NaCl; 5) Supernatant of autolysis with 7.5% PEG-8000, 50 mM Tris pH 8.0, 10 mM EDTA, 1% Triton X-100+0.3M NaCl; 6) Supernatant of autolysis with 7.5% PEG-8000, 50 mM Tris pH 8.0, 10 mM EDTA, 1% Triton X-100+0.4M NaCl; 7) Same as lane 6; 8) TE (10 mM Tris pH 8.0, 1 mM EDTA) extraction of insoluble material pelleted from autolysis with 7.5% PEG-8000, 50 mM Tris pH 8.0, 10 mM EDTA, 1% Triton X-100+0.4M NaCl In FIG. 10., agarose gel analysis of clarified lysate by autolysis in PNL buffer with SDS and $Ca^{2+}$ is shown. Endolysin containing fermentation cells carrying a high copy DNA vaccine plasmid were utilized in autolysis.

Figure 11:

In FIG. 11., agarose gel analysis of samples from a purification of pDNA using autolysis and filter membranes is shown. Endolysin containing fermentation cells carrying a high copy DNA vaccine plasmid were utilized in autolysis. Lanes: M) 1 kb DNA ladder; 1) clarified lysate, 2) filtrate of the plasmid precipitation mixture; 3) wash filtrate; 4) first 5 mL TE filtrate fraction; 5) second 5 mL TE filtrate fraction; 6) 75 mL TE filtrate fraction.

Figure 12:
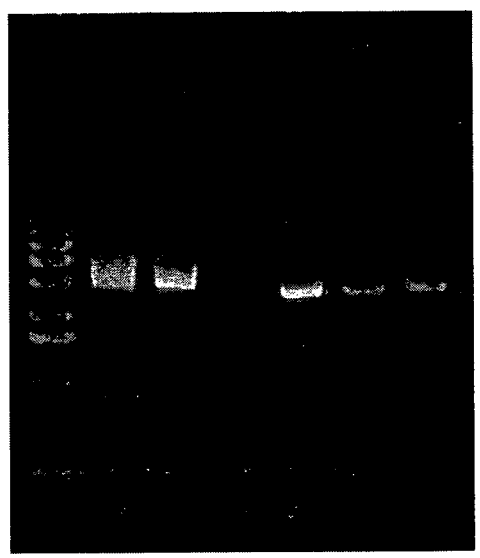

In FIG. 12., agarose gel analysis of samples from a purification of pDNA by autolysis and a non-chromatographic process is shown. Endolysin containing fermentation cells carrying a high copy DNA vaccine plasmid were utilized in autolysis. Lanes: M) 1 kb DNA ladder; 1) 2 μL clarified lysate; 2) 2 μL clarified lysate after 65° C. step; 3) 2 μL supernatant after precipitation of plasmid DNA by NaCl addition; 4) 2 μL of the redissolved plasmid DNA; 5) 2 μL after removal of the hydrated calcium silicate; 6) 0.1 μL of the final plasmid solution (diluted prior to loading).

Figure 13:
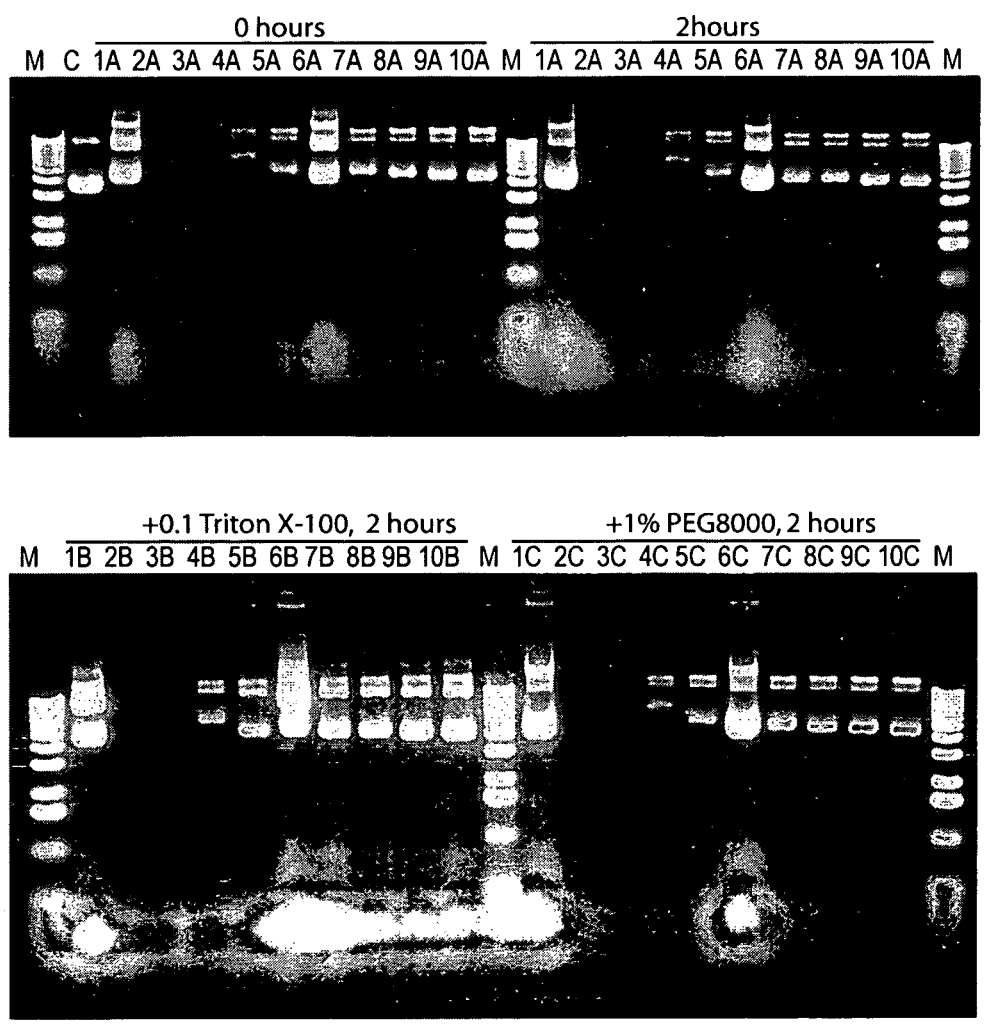

In FIG. 13., effects of salt concentration, extraction time, Triton X-100 and PEG8000 on plasmid extraction from endolysin containing fermentation cells carrying a high copy plasmid are shown.

Lanes: M, 1 kb DNA ladder; C, 0.5 μg of the same plasmid prepared by alkaline lysis (equivalent 100% recovery for comparison of the extractions shown). 1 μL of supernatant from each of the extractions described in Table 4 (samples 1-10A, B or C) was loaded.

Figure 14:
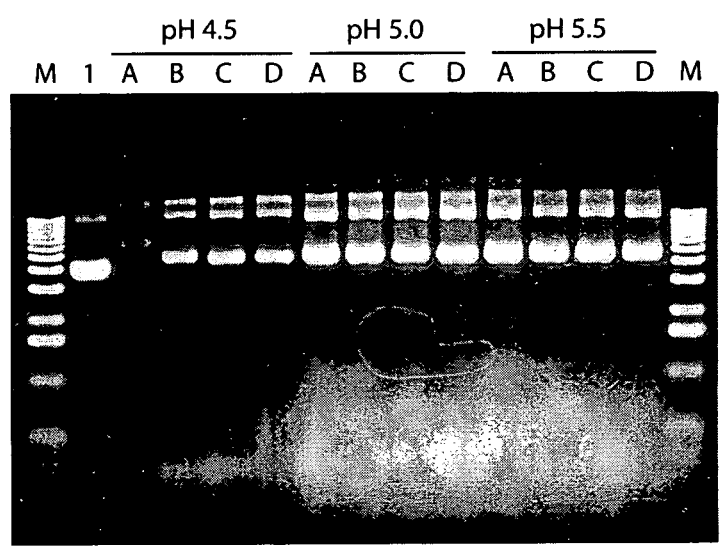

In FIG. 14., the effect of pH and sodium acetate concentration on plasmid extraction is shown. Agarose gel analysis, Lanes: M, 1 kb DNA ladder; 1, 0.5 μg plasmid control sample; A lanes, 0.4 M sodium acetate; B lanes, 0.6 M sodium acetate; C lanes, 0.8 M sodium acetate, D lanes, 1.0 M sodium acetate.

Figure 15:
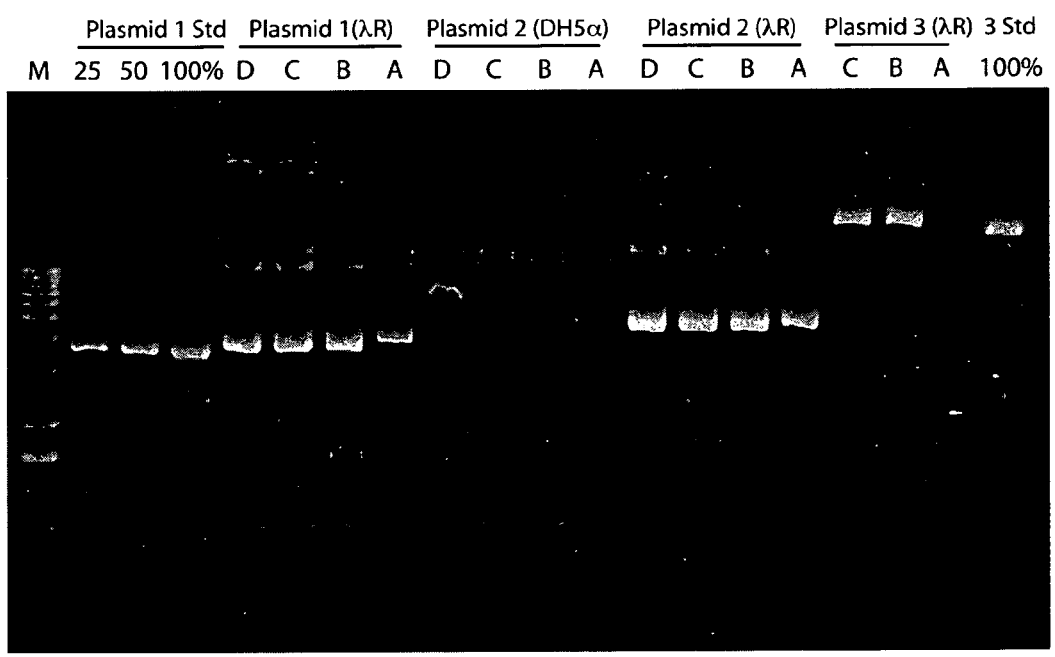

In FIG. 15., low pH extraction of various plasmids, with or without endolysin, is shown.

Figure 16:
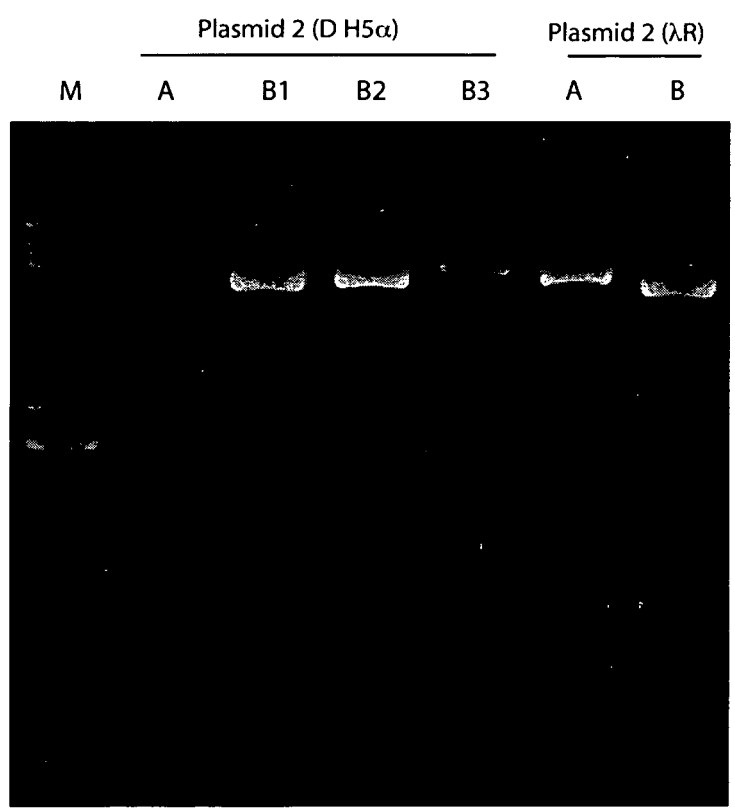

In FIG. 16., substitution of lysozyme for endolysin in low pH extraction is shown.

Figure 17:
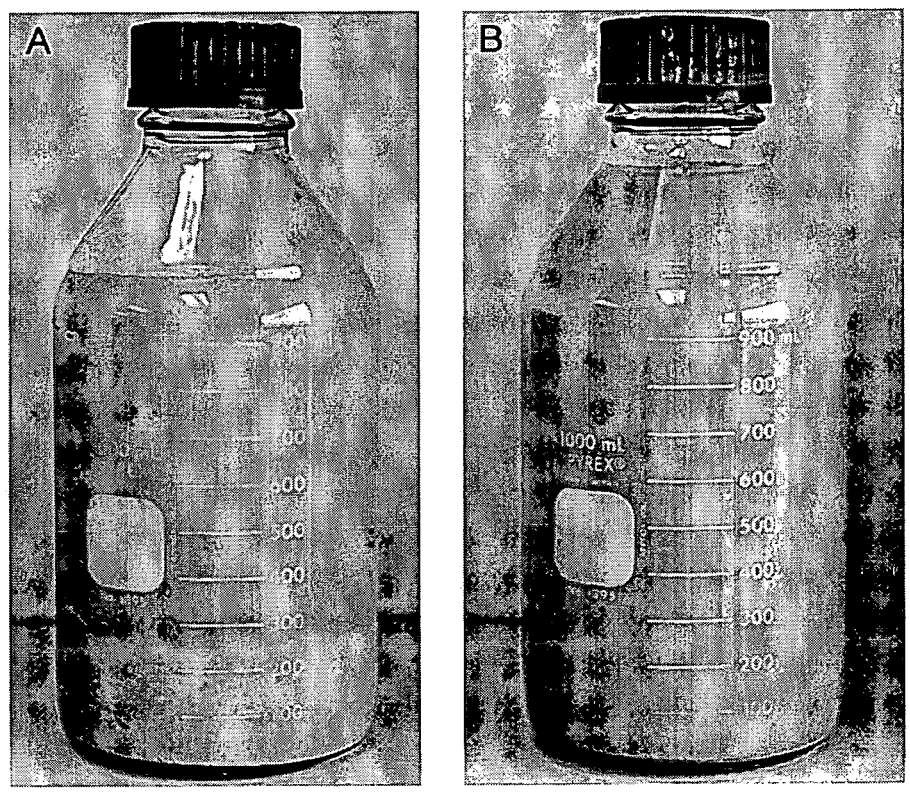

In FIG. 17., improved solid liquid separation by thermal flocculation of an autolytic extraction mixture is shown. A) Autolytic acidic plasmid extraction lysate followed by thermal treatment resulting in flocculation and sedimentation of cell debris. B) Lysate prepared from autolytic cell paste in a pH 8.0 buffer resulting in poor flocculation and sedimentation of cell debris.

Figure 18:
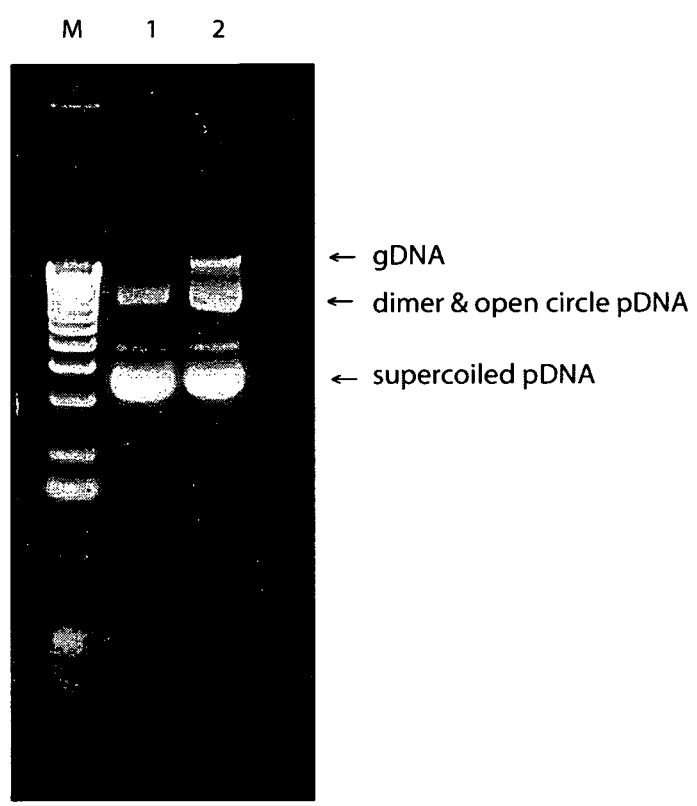

In FIG. 18., an agarose gel analysis of lysates prepared by either the low pH extraction—thermal flocculation process, or by pH 8 heat lysis are shown. Lanes: M, 1 kb DNA ladder; 1, 1 μg DNA from low pH extraction—thermal flocculation process; 2, 1 μg DNA from the pH 8 heat lysis process.

Definitions

Amcyan: Anemonia majano cyan fluorescent protein.

autolysin: Bacterial encoded endolysin-like protein that can mediate autolysis.

autolysis: Lysis methods that cause the cell to undergo self lysis, such as β lactam induced cell lysis, autolysin induced lysis, phiX174 phage lysis protein induced ghosting, T4 or lambda phage induced cell lysis by: phage lysozyme/phage holin coexpression; freeze thaw, or; phage lysozyme in combination with buffers that permeabilize the inner membrane, etc.

autolysis process: Peptidoglycan hydrolase digestion of the cell wall is utilized to effect cell lysis.

autolyte buffer: Low pH extraction buffer of the composition 30 mM sodium acetate, 50 mM EDTA, 8% sucrose, 0.1% Triton X-100, pH 5.2; or modifications that include up to 400 mM sodium acetate, 0-50 mM EDTA 0-100 μg/mL PEI, pH 4.7-5.5, 0.05-2% Triton X-100 or 0.5-1% SDS substituted for Triton X-100.

ccc: Covalently Closed Circular.

DNA replicon: Plasmids, cosmids, bacterial artificial chromosomes (BACs), bacteriophages, viral vectors and hybrids thereof.

E. coli: Escherichia coli, a gram negative bacteria

EDTA: ethylene diamine tetraacetic acid.

EGFP: enhanced green fluorescent protein.

endolysin: Phage encoded lysozyme, such as those encoded by the bacteriophage lambda gene R (λR), bacteriophage T4 gene e, and bacteriophage T7 lysozyme genes.

EU: Endotoxin units, KEU=kilo endotoxin units, a measurement of Lipopolysaccharide (LPS) content.

g: Gram, kg for kilogram, mg for milligram.

gDNA: Genomic DNA.

ghost band: Denatured ccc DNA.

HA: Hemagglutinin.

holin: Phage protein that inserts into the cytoplasmic membrane and forms pore allowing endolysin access to cell wall.

HEWL: Chicken (hen) egg white lysozyme.

Hr(s): Hour(s).

Kd: Kilodalton.

L: Liter, mL for milliliters, µL for microliters.

low pH extraction process: Peptidoglycan hydrolase digestion of the cell wall is utilized to permeabilize cells to effect plasmid release without complete lysis of the cell or extensive extraction of gDNA by resuspension of peptidoglycan hydrolase containing cells in a low pH autolyte buffer or equivalent (e.g. citrate based buffer).

min: Minute.

$OD_{600}$: Optical density at 600 nm.

OD-unit: One OD-unit is equivalent to the amount of cells, which when suspended in a volume of 1.0 mL, gives an $OD_{600}=1.0$.

pDNA: Plasmid DNA.

PEG: Polyethylene glycol.

PEI: Polyethyleneimine.

peptidoglycan hydrolase: Murein hydrolases, including endolysin, autolysins or lysozymes that digest the cell wall (murein). Reviewed in Salazar O, Asenjo JA 2007 Biotechnol. Lett 29:985-994.

phage lysis proteins: Proteins cause the cell to undergo self lysis or ghosting such as ghosting induced by phiX 174 phage lysis protein, or cell lysis induced by T4 or lambda phage lysozyme-holin coexpression.

plasmid: Plasmids, cosmids, bacterial artificial chromosomes (BACs), bacteriophages, viral vectors and hybrids thereof.

plasmid extraction: Endolysin digestion of the cell wall is utilized in a process to permeabilize cells to effect plasmid release without complete cell lysis (endolysin mediated non-lytic cell permeabilization).

plasmid-safe nuclease: Exonuclease such as T5 exonuclease that degrades various forms of DNA but not covalently closed circular (ccc) DNA including pDNA.

PNL buffer: A solution containing approximately 7.5% PEG-8000, 1-100 mM EDTA, 10-50 mM Tris pH 7-9, and salt in the range of 0-1 M.

pNTCultra: pDNAVACCUltra DNA vaccine plasmids as disclosed in Williams, JA 2006 World Patent Application WO2006078979, with various backbone modifications or antigen genes.

precipitant: A substance that causes a precipitate to form when added to or included in a solution.

precipitate: n. A solid or solid phase separated from a solution. v. To be separated from a solution as a solid.

RBS: Ribosome Binding Sites.

RNase: Ribonuclease.

RNaseA: Bovine pancreatic ribonuclease A.

RT-PCR: Real time PCR.

SDS: Sodium dodecyl sulphate, an anionic detergent.

SDS-Calcium: $SDS-CaCl_2$, a method of forming a flocculant precipitate after sequential addition of a SDS anionic detergent component followed by a calcium chloride ($CaCl_2$) cation component. This forms Calcium Dodecyl Sulfate, a calcium surfactant that forms insoluble flocculated complexes (calcium dodecyl sulfate complexes) with protein, lipopolysaccharides, and other host cell impurities while leaving pDNA in solution.

sec: Seconds.

STET buffer: A solution containing approximately 8% sucrose or 8% glucose, 0.01-5% Triton X-100, 10-100 mM EDTA, 10-50 mM Tris pH 8.0.

synthetic anionic surfactant: Formed after sequential addition of a anionic detergent component followed by a cationic component, preferably an alkaline earth metal (e.g. Calcium Dodecyl Sulfate, a calcium surfactant formed by sequential addition of $SDS-CaCl_2$).

T5 exonuclease: Bacteriophage T5 D15 exonuclease.

TE buffer: A solution containing approximately 10 mM Tris pH 8 and 1 mM EDTA.

TFF: Tangential flow filtration or cross flow filtration.

Tris: trishydroxymethylaminomethane. Stock solutions are typically made using either Tris-base, pH adjusted down with hydrochloric acid (HCl) or with Tris-HCl, pH adjusted up with sodium hydroxide (NaOH).

WCW: Wet cell weight.

zwf: Glucose 6-phosphate dehydrogenase.

The invention relates to methods for the production and purification of plasmid DNA (pDNA) using the gram negative bacterium *E. coli* as a production host. One embodiment of the invention includes alternative cell lysis and plasmid extraction methodologies that utilize endolysin producing host strains. These methodologies eliminate alkaline, lysozyme, or heat lysis methodologies which are by nature problematic and are a major process bottleneck (FIG. 1). A summary of application of various embodiments of the invention is shown in FIG. 2.

Another major problem of purification technology has been the separation of pDNA from *E. coli* gDNA. Some embodiments of the invention disclose methods for reducing gDNA during isolation of covalently closed circular (ccc) DNA. This is accomplished, for example, through PEG flocculation of an autolysate which removes cell debris as well as gDNA. In an alternative embodiment, gDNA is reduced by extracting plasmid from cells under conditions in which gDNA is retained in the cells.

Autolysis Process Preferred Embodiments

Cells are produced in fermentation culture. After production, plasmid is purified from the cells. In a preferred embodiment, cells are lysed using autolysis. A preferred method of autolysis is to disrupt cells by release of cytoplasmic peptidoglycan hydrolase that is produced by the host strain. In a preferred embodiment, the peptidoglycan hydrolase is a bacteriophage endolysin. In a preferred embodiment, endolysin is expressed in the cytoplasm of the cell and released from the cytoplasm after cell growth by utilization of a lysis buffer that permeabilizes the inner cell membrane. This is superior to processes that utilize: 1) holin gene expression to release endolysin from the cytoplasm, or; 2) freeze thaw to release endolysin from the cytoplasm or; 3) recombinant lysozyme to degrade the cell wall. Holin gene expression during growth to release endolysin does not allow cell harvest or storage, or the control of the time and buffer composition of lysis. Freeze thaw is not a scaleable manufacturing process. Recombinant lysozyme adds prohibitive cost to plasmid production (Hoare M, Ley M S, Bracewell D G, Doig S D, Kong S, Titchener-Hooker N, Ward J M, Dunnill P. 2005 *Biotechnology Progress*. 21: 1577-1592).

The application of peptidoglycan hydrolase expressing cell lines to plasmid production is not taught in the art. A number of investigators have developed plasmid isolation processes that utilize lysozyme. These include methods for lysing EDTA-lysozyme spheroplasts based on the original description of Clewell D B 1972 *J. Bacteriol.* 110: 667-676 and Clewell D B, Helinski D R. 1970 *Biochemistry* 9:4428-4440. Boyd et al, *Supra*, 2006 discloses a large scale STET/recombinant lysozyme lysis method for plasmid production. These inventors do not contemplate utilization of autolytic cells to replace the need for exogenous lysozyme. Lysozyme is also utilized in the large scale heat lysis process of Lee and Sagar, *Supra,* 2001. These inventors also do not contemplate utilization of autolytic cells to replace the need for exogenous lysozyme as is disclosed herein.

A number of investigators have developed protein isolation processes that utilize endolysin cell lines. Crabtree S, Cronan J E. 1984 *J. Bacteriol.* 158: 354 disclose use of pJH2 (inducible lambda R and Rz endolysin, with S gene mutation, so endolysin only) to lyse *E. coli* strains by freeze thaw. The disclosure teaches using autolysis for cell lysis, and does not contemplate using autolysis for plasmid or DNA purification. Leung and Swartz, *Supra,* 2001 disclose autolytic strains using arabinose inducible phage T4 lysis proteins. In this system, lysozyme (T4 gene e endolysin) is expressed by the cell in the cytoplasm and released to the periplasm at the desired time by co-expression of a holin (membrane spanning peptide or protein) that creates a channel, allowing leakage of lysozyme from the cytoplasm to the periplasm. In an alternative embodiment, T4 endolysin is used without holin to lyse cells after a freeze thaw cycle. This disclosure teaches that autolysis requires either holin gene expression or freeze thaw for lysis. This disclosure also teaches using autolysis for protein purification, and does not contemplate using autolysis for plasmid or DNA purification. Auerbach J, Rosenberg M, 1987 U.S. Pat. No. 4,637,980, disclose lysogens which contain single copy, inducible lambda endolysin, for cell lysis. The disclosure indicates in theoretical terms that the strains can be utilized for plasmid purification, but data to support this is not disclosed in the application. Other autolytic *E. coli* strains taught by Jia et al, *Supra* 2006 contain the bacteriophage λR lytic endolysin gene integrated into the genome. The endolysin is induced by arabinose, which then causes the *E. coli* to be lysed after a freeze-thaw cycle. This disclosure teaches that autolysis with endolysin protein containing cells requires freeze thaw lysis; multiple examples are listed and in all cases freeze thaw was required for autolysis. This teaches away from the current disclosure of endolysin mediated autolysis in simple buffer solutions without freeze thaw. The disclosure indicates in theoretical terms that the strains can be utilized with freeze thaw for nucleic acid extraction and isolation, but data on nucleic acid extraction is not disclosed in the application. Studier FW. 1991, *J Mol. Biol.* 219: 37-44 disclose cell lines containing the pLysS or pLysE plasmids encoding constitutively produced cytoplasmic phage T7 lysozyme; theses cell lines have been utilized by dozens of investigators to lyse cells for protein isolation using one or more freeze thaw cycles or Triton X-100/EDTA lysis solutions, but have not been applied to plasmid purification.

Kloos D, Stratz M, Guttler A, Steffan R J, Timmis K N. 1994 J Bacteriol. 176: 7352-7361, and Jain V, Mekalanos JJ. 2000 *Infect Immun* 68: 986-989 disclose endolysin/holin (lambda S, R and Rz) expressing plasmids that are used to lyse cells and release DNA. Use of these systems for pDNA purification are not contemplated by the authors, and the systems are not applicable for purification of heterologous plasmids since such plasmid preparations would be contaminated with the lysis gene plasmid (the lysis genes are not integrated). As well, the systems utilize holin genes (Lambda S) for lysis.

Williams and Hodgson, *Supra,* 2006 disclose the use of endolysin/holin combination expressing cell lines for plasmid production, and the use of plasmid safe exonuclease to reduce viscosity after lysis. The authors do not disclose the use of endolysin only cell lines for plasmid production.

We disclose herein the application of endolysin expressing cell lines to plasmid production. The disclosed autolysis process using the endolysin expressing cell line embodiments of the invention is a critical design improvement in bacterial cell lysis. As discussed above, current lysis methods for plasmid production require addition of expensive lysozyme (e.g. Boyd et al, *Supra,* 2006; Zhu et al, *Supra,* 2005). This is not an optimal manufacturing process, due to cost and regulatory concern (lysozyme). As well, endolysin-holin lysis systems have scaling and process control issues. In-fermentor holin lysis destroys cells prior to cell testing or release by Quality Assurance and prevents normal harvest unit operations to be performed. The endolysin mediated autolysis process disclosed herein is a scaleable cost effective process that meets a long felt, but unsolved need for elimination of alkaline or heat lysis methodologies which, as discussed previously, are problematic due to specialized equipment needs, scaling issues, and tremendous lysis volumes.

Preferred peptidoglycan hydrolase genes for practicing various embodiments of the invention are chicken (hen) egg white lysozyme (HEWL), alternative lysozymes, autolysins, or bacteriophage endolysin gene products. Preferred endolysin genes are the bacteriophage lambda R, the bacteriophage T4 gene e, or the bacteriophage T7 lysozyme genes. Alternative peptidoglycan hydrolase genes that may be utilized to practice various embodiments of the invention, and a discussion of their action, are disclosed in Salazar and Asenjo, *Supra,* 2007 and are included herein by reference.

Extraction Process Preferred Embodiments

In a preferred embodiment, plasmid is extracted from cells without complete cell lysis. A preferred method of plasmid extraction is to disrupt cells by release of cytoplasmic endolysin that is produced by the host strain and permeabilize the cell wall under conditions in which: 1) the cell does not completely lyse, and 2) plasmid is released from the cell. In a preferred embodiment the conditions in which, 1) the cell does not completely lyse, and 2) plasmid is released from the cell, comprise low pH treatment (pH 4.7-6.9) of endolysin containing cells with nonionic or ionic detergents (low pH extraction process). In a preferred embodiment, the low pH extraction process is used to extract a soluble protein from the cell. The inventors have surprisingly determined that this can be accomplished by permeabilizing the inner membrane of an endolysin cell line, or by permeabilizing the inner membrane and outer membrane of an non-endolysin cell line in the presence of lysozyme (FIG. 3). Optionally, outer membrane permeabilizing compounds such as EDTA are included to improve the yield of extracted plasmid DNA with endolysin expressing cell lines.

A preferred composition of the extraction solution contains 0.03-0.4 M sodium acetate, 0-50 mM EDTA, 0-8% sucrose pH 4.7-6.0 in which the nonionic detergent is 0.05-1% Triton X-100. Yet another preferred composition of the extraction solution contains 0.03-0.4 M sodium acetate, 0-50 mM EDTA, 0-8% sucrose pH 4.7-6.0 in which the ionic detergent is 0.5-1% SDS. Yet another preferred composition of the extraction solution contains 0.03M sodium acetate, 50 mM EDTA, 0-8% sucrose pH 4.8-5.2 in which the nonionic detergent is 0.05-1% Triton X-100. Yet another preferred composition of the extraction solution contains 0.03M sodium acetate, 50 mM EDTA, 8% sucrose pH 5.0 in which the ionic detergent is 0.5-1% SDS. Yet another preferred composition of the extraction solution contains 0.4M sodium acetate, 10 mM EDTA, pH 4.8. Yet another preferred composition of the extraction solution contains 0.03M sodium acetate, 50 mM EDTA, 8% sucrose pH 5.0. Alternative outer membrane-permeabilizing compounds, such as polyethyleneimine (Helander I M, Alakomi H L, Latva-Kal K, Koski P. 1997. *Microbiology* 143:3193-3199) may also be included, in addition to, or replacing EDTA. Yet another preferred composition of the extraction solution contains 0.03M sodium acetate, 1 mM EDTA, 50 µg/mL polyethyleneimine, 8% sucrose, pH 5.2 in which the nonionic detergent is 0.05-0.1% Triton X-100. Various ionic and or nonionic detergents are also contemplated for use in place of Triton X-100. For example, various compounds that permeabilize the outer membrane are discussed in Vaara M. 1992 Microbiological Reviews 56: 395-411 and Leung and Swartz, Supra, 2001, and are included herein by reference.

Resuspension of cells in these solutions results in extraction of pDNA without substantial extraction of gDNA or cell lysis, or excessive viscosity. The inventors disclose herein that other salts or acids (e.g. potassium acetate, lithium acetate, sodium citrate, acetic acid, citric acid) may also be used in this process. Additional preferred components and concentrations can be determined by one skilled in the art. Autolytic cells containing pDNA can be resuspended or buffer exchanged with the extraction solution to recover pDNA. The inventors disclose herein that pDNA extraction occurs quickly upon resuspension of concentrated autolytic cells or autolytic cell paste in the extraction solution.

The use of endolysin expressing strains in the plasmid extraction method embodiments of the invention is a critical design improvement in extraction of pDNA from cells. Chemical methods for non-lytic permeabilization of bacterial cells have been described in the art. Genomic DNA release from E. coli has been reported in the presence of EDTA and low ionic strength (i.e. TE buffer). Inclusion of salt reduced DNA release, as did elimination of EDTA (Paul J H, David A W. 1989 Appl. Environ. Micro. 55: 1865-1869). Subsequently, leakage of low levels of plasmid from cells under similar low ionic conditions has been reported. Plasmid leakage was observed in aqueous solutions, for example 10 mM Tris 10 mM EDTA, pH 8.5, water, 10 mM Tris/1% Tween 20. Yield was low, and much of the released plasmid was nicked or linearized. Addition of protease K was required to obtain significant amounts of plasmid leakage, and much of the released plasmid remained nicked or linearized (Baker M, Taylor M. 2003 World Patent Application WO03046177). Although acceptable for analytical sample preparation, nicked plasmid is difficult to remove; as well, enzyme treatments are not economical in large scale manufacture. In the case of EDTA permeabilization, EDTA is known to permeabilize cells at sensitive sites adjacent to division septa; this permeabilization could account for the low yield of plasmid leakage without enzymatic treatment since division septa are present on <1% of stationary phase cells, and only 20-30% of mid-log phase cells (Shellman V L, Pettijohn D E. 1991 J Bacteria 173:3047-3059).

In another example, harsh conditions, heating the bacteria at 80-95° C. in a permeabilization solution containing a non-ionic detergent (0.07% Triton X-100) a metal chelating agent (10 mM EDTA), and optionally an ionic detergent (1% lithium lauryl sulfate) were employed to release ribosomal RNA and gDNA suitable for analytical applications (Clark K A, Kacian D L. 1998 U.S. Pat. No. 5,837,452). The integrity of released DNA was not assessed, nor was release of pDNA.

Disclosed herein, the inventors have identified that non-endolysin fermentation production cells are resistant to EDTA or non-ionic detergent extraction using the conditions of Clark and Kacian, Supra, 1998 and/or Baker and Taylor, Supra, 2003. This unexpected observation demonstrates that non-lytic plasmid extraction methods taught in the art are not applicable to plasmid fermentation cells. We disclose herein the novel observation that plasmid fermentation cells expressing endolysin are permissive to plasmid DNA extraction in a variety of buffer conditions.

While not limiting the application of the invention embodiments, the resistance of fermentation cells to plasmid extraction may be related to the observation that E. coli cells vary tremendously in their resistance to sonication, electroporation (Calvin N M, Hanawalt P C. 1988 J. Bacteriol. 170: 2796-2801), or pressure treatment (Manas P, Mackey B M. 2004 Appl Environ Microbiol. 70: 1545-54) depending on the stage of growth or growth temperature. In general, log phase cells are more sensitive, while stationary cells are more resistant to lysis or leakage. However, late stage stationary phase anoxic saturated cultures utilized for reported plasmid leakage studies (e.g. Baker and Taylor, Supra, 2003) are less healthy, and may leak plasmid due to cell membrane weakening in response to anoxia. The unexpected observation that the presence of endolysin facilitates plasmid extraction from fermentation cells enables the application of plasmid extraction to large scale plasmid production from fermentation cells.

The use of a slightly acidic solution to extract plasmid from cells, with or without endolysin, is not taught in the art. Rather, the art teaches that endolysin and lysozyme function poorly at low pH. Characterization of the activity of HEWL, T4 endolysin (T4 gene e) (Jensen H B, Kleppe K. 1972, Eur. I Biochem 28:116-122) and lambda R endolysin (Evrard C, Fastrez J, Soumillion P. 1999 FEBS letters 460, 442-446) demonstrated very little activity of all these enzymes below pH 6. Consistent with this, poor protein release and lysis with the Xja cell line (integrated lambdaR endolysin) in a 100 mM sodium acetate buffer at pH 5, or pH 5.5-6.5 using Tris or phosphate buffers is taught by Jia, et al, Supra, 2006.

Plasmid purification itself is generally not done at low pH. One heat lysis process has been developed wherein bacteria are captured on a filter cake, and lysed at 70° C. in a pH 4.7 citrate buffer. In this case, plasmid is retained on the filter cake after lysis. Lysozyme is utilized, but in a previous neutral pH fragilization step rather than in the lysis buffers (O'Mahony K, Freitag R, Hilbrig F, Schumacher I, Muller P. 2007 Biotechnol Prog. 23: 895-903). This study does not teach low pH extraction of plasmid (cells are lysed under conditions in which plasmid is not released), and teaches away from the current embodiment of the invention as it further teaches that lysozyme will not function in a low pH lysis buffer.

Homogenization of cells preconditioned at pH 4-4.5 has been reported to improve cell debris removal after homogenization through reduced biomass-biomass interaction (Gehart R L, Daignault R A 2004 World Patent Application WO2004022581). This method is utilized in protein purification after homogenization; the authors did not contemplate use of the method without homogenization or to extract pDNA.

The art has demonstrated that treatment of cells with low amounts of lysozyme can be used to isolate "lysozyme nucleoids" in which cytoplasmic protein and RNA is released while the nucleoid retains largely intact cell boundaries and DNA (Reviewed in Murphy L D, Zimmerman S B 2001 J Structural Biol. 133: 75-86). These studies do not teach that pDNA is released separate from gDNA. Consistent with this in a plasmid purification process in which lysozyme EDTA spheroplasts are isolated prior to lysis for plasmid purification, plasmid was associated with the spheroplasts; this teaches that plasmid is not released by lysozyme-EDTA treatment (Wicks. IP, Howell M L, Hancock T, Kohsaka H, Olee T, Carson D A. 1995 Human Gene Therapy 6: 317-323).

A variety of studies that demonstrated that the majority of pDNA in a cell with relaxed replication such as ColE1 is separable from gDNA likewise did not identify conditions for extracting plasmid (e.g. Kline B C, Miller J R, Cress D E, Wlodarczyk M, Manis J J, Often M R. 1976. *J Bacteriol.* 127: 881-889).

Autolysis Process Lysate Clarification Preferred Embodiments

The product of the autolysis process, as opposed to the low pH extraction process (which doesn't liberate gDNA) or alkaline or heat lysis (which selectively denatures gDNA) is very viscous, creating processing problems. In one preferred embodiment of the invention, viscosity is reduced by digesting gDNA utilizing a coexpressed plasmid safe nuclease as described in Williams and Hodgson, *Supra*, 2006. In another preferred embodiment of the invention, viscosity is reduced by flocculating and removing gDNA and cell debris.

A variety of different flocculants can be used to aggregate host cell debris. Several are disclosed in Boyd et al, *Supra*, 2006 and are included herein by reference. In one preferred embodiment of the invention, gDNA and cell debris are removed by flocculation with polyethylene glycol (PEG).

By way of example, consider the following methods to purify pDNA with the PEG lysis process 1) A preferred composition of the PEG lysis buffer contains concentrations of PEG and a salt in which pDNA is soluble and gDNA and/or other impurities are insoluble. For example, a preferred composition contains 7.5% w/v PEG-8000, and 0.1-0.2 M NaCl. Additional preferred components and concentrations can be determined by one skilled in the art, for example, 10 mM EDTA, 50 mM Tris, and 0.05 to 2% Triton X-100.

2) A preferred embodiment is the use of this PEG lysis process for purification of pDNA from autolytic strains. Suspension of autolytic cells in the PEG lysis buffer lyse readily without freeze-thaw. This process may also be used with non-autolytic cells, and addition of lysozyme may be used to aid lysis.

3) In another preferred embodiment, protein and other impurities can be precipitated and removed by heat treatment and clarification of the PEG lysate. A preferred heat treatment is performed by heating the lysate to 65° C.-75° C. for at least 15 minutes.

4) In another preferred embodiment, pDNA may optionally be recovered from the lysate after clarification by precipitation. A preferred method of precipitation of the pDNA from the PEG lysate is performed by raising the NaCl concentration of the solution to >0.3M NaCl. Precipitation of pDNA by this method also results in the removal of RNA, since RNA remains soluble and will be separated from the precipitated pDNA.

5) In a preferred embodiment an ionic detergent such as SDS is added, followed by addition of calcium ($Ca^{2+}$) to complex with the SDS, gDNA, protein, lipopolysaccharides, and other host cell impurities, (e.g. SDS-Calcium treatment to make calcium dodecyl sulfate) leaving the pDNA in solution. These flocculant precipitates can then be removed by solid-liquid separation.

It is known in the art that PEG can be added to lysates to aid removal of gDNA and PEG flocculation allows debris removal with low speed centrifugation. For example, Chen Z. Ruffner D 1998 World Patent Application WO9816653 describes adding magnesium chloride to 1 M and PEG to 3.3% to alkaline lysates to precipitate cell debris RNA, gDNA and proteins from pDNA, to facilitate lysate clarification. In Boyd et al, *Supra*, 2006, PEG is used to flocculate gDNA and host cell debris from a lysozyme mediated lysate. Neither of these disclosures teaches PEG flocculation of autolysates. The novel and new combination of PEG flocculation with endolysin mediated autolysis disclosed herein is demonstrated to provide an efficient method for lysate clarification and gDNA reduction.

Low pH Extraction Process Clarification Preferred Embodiments

By way of example, consider the following methods to purify pDNA after extraction of pDNA from endolysin or lysozyme expressing strains 1) A clarified pDNA solution may be recovered from the cell matter in the extraction mixture by various methods known to those skilled in the art including, but not limited to: batch centrifugation, continuous centrifugation, flocculation of impurities, precipitation of impurities, body feed filtration, rotary vacuum filtration, normal flow filtration, TFF. Various methods of clarifying lysates are discussed in Hoare et al, *Supra*, 2005 and are included herein by reference.

2) In a preferred embodiment, the extraction mixture, or the plasmid containing supernatant from the extraction, is subjected to heat treatment (65-90° C.) for precipitation of proteins and flocculation of the extraction mixture. Heat treatment may be performed in batch or continuous mode. A preferred heat treatment is performed in continuous flow mode in the temperature range of 65-90° C. for 20-90 seconds (sec).

3) In a preferred embodiment an ionic detergent such as SDS is added, followed by addition of calcium ($Ca^{2+}$) to complex with the SDS, gDNA, protein, lipopolysaccharides, and other host cell impurities, (e.g. SDS-Calcium treatment to make calcium dodecyl sulfate) leaving the pDNA in solution. These flocculant precipitates can then be removed by solid-liquid separation.

4) Another preferred embodiment is the use of expanded bed adsorption (EBA), fluidized bed adsorption, or batch adsorption to recover the pDNA from the extraction mixture. Unlike traditional packed beds, EBA columns do not require a highly clarified feed stream. EBA columns are fed from below, creating an expanded resin bed that allows particulates to flow around the beads to avoid clogging. EBA is optimally operated at a flow rate such that the upward flow velocity exceeds the sedimentation velocity of the particulates in the feed, but does not exceed the sedimentation velocity of the resin. Expanded bed anion exchange adsorption resins and columns are commercially available (e.g. Streamline DEAE, Streamline Q XL; GE Healthcare). Application of EBA chromatography to capture pDNA from crude lysates has been reported (Ferreira G N, Cabral J M, Prazeres D M. 2000. *Bioseparation* 9: 1-6; Theodossiou I, Søndergaard M, Thomas O R. 2001. *Bioseparation* 10: 31-44)

5) Another preferred embodiment is the use of tangential flow filtration or cross flow filtration (TFF) for separation of plasmid from impurities. For, example, the pDNA may be recovered from the extraction mixture by TFF with a membrane that has a pore size that allows the pDNA, but not the cells, to permeate (e.g. 0.2 µm or 0.45 µm). Preferred membrane materials, pore sizes, and operating parameters can be determined by one skilled in the art.

6) Optionally, the extraction mixture is subjected to TFF with a membrane that has a pore size that retains the pDNA, but allows smaller impurities (e.g. RNA, proteins) to be removed in the filtrate prior to further processing. This method could be integrated with fermentation harvest by TFF (e.g. with a 500 kD or 750 kD membrane) by following cell concentration with diafiltration with the extraction solution.

7) Another preferred embodiment is the use of TFF for combined cell concentration, buffer exchange, and pDNA extraction and recovery after fermentation. For example, a membrane with a pore size that retains cells, but allows pDNA to permeate, may be used first as a harvest step to concentrate a fermentation culture. Once the cells have been sufficiently concentrated to remove the bulk of the culture medium, the plasmid extraction solution may be added (either batch-wise or continuously by diafiltration); continued TFF then results in recovery of the extracted pDNA in the filtrate.

Plasmid Purification Preferred Embodiments

The resulting pDNA liquor after primary clarification may be purified in a downstream process. Boyd et al, *Supra*, 2006 summarizes a number of downstream processes that are compatible with clarified lysates; these methods are included herein by reference.

We contemplate utilizing host strains expressing endolysin, and optionally plasmid-safe nucleases, to produce plasmid enriched feed streams from high yield fermentation culture in exemplary plasmid purification processes. The combination of endolysin mediated autolysis with flocculation, and/or endolysin mediated plasmid extraction processes with exemplary downstream purification processes provide cost effective methodologies for plasmid production for gene therapy and DNA vaccination applications.

Endolysin Expression Preferred Embodiments

Expression of the endolysin and/or nuclease genes may be driven by constitutive or, more preferably, inducible promoters. Inducible promoters that are preferred include, but are not limited to, lambda PR and PL, other phage promoters such as T5 or T7, synthetic promoters such as tac and trc, endogenous promoters such as lac, cold shock promoters (cspA), araBAD, stationary phase or starvation promoters, growth rate (rmf), pH (cadA), or anoxia responsive (nar) promoters. Induction can be by increased temperature (PL, tac) with thermolabile repressors (lambda repressor, lac repressor, respectively), decreasing temperature (cspA; cold shock promoter), inducers (IPTG for tac, trc and lac; Arabinose for AraBAD) or cellular or environmental changes (e.g. entry into stationary phase, pH or oxygen shift, glucose or amino acid starvation; reviewed in: Makrides S C. 1996 *Microbiol. Rev.* 60: 512-538). Alternatively, the gene may be induced by a regulated antisense RNA or by a chemical inducer binding to a riboswitch control region in the RNA leader.

Host Strains for Autolytic Gene Expression

In a preferred embodiment, the endolysin gene is expressed from a plasmid that is compatible with a expression plasmid containing a target protein gen. In another preferred embodiment, the endolysin gene is integrated into the genome. For applications where a plasmid DNA rather than a protein is the product, the endolysin gene is preferably integrated into the genome. Strain engineering can be performed in any strain of bacteria that is suitable for plasmid production.

Compatibility of endolysin cell lines with fed-batch processes in animal product free NTC3019 fermentation media optimized for plasmid production (disclosed in Carnes and Williams, *Supra*, 2006 and included herein by reference) is demonstrated herein. Other plasmid fermentation processes known in the art (see Background of the Invention) are also contemplated for use with the endolysin cell line embodiments of the invention. An investigator skilled in the art could modify or create de novo, if necessary, endolyin expressing cell lines with alternative endolysin expression control. For example, in alternative preferred hosts as needed for adaptation to different plasmid fermentation processes, such as the defined media fed-batch process of Huber, H., Weigl, G., Buchinger, W 2005 World Patent Application WO2005097990 in the preferred host strain *E. coli* JM108 (Huber, H., Pacher, C., Necina, R., Kollmann, F., Reinisch, C 2005 World Patent Application WO2005098002).

EXAMPLES

The methods and compositions of the invention are further illustrated in the following examples. These are provided by way of illustration and are not intended in any way to limit the scope of the invention.

Example 1

Fermentation Process Optimization

Carnes and Williams, *Supra*, 2006 disclosed methods for fed-batch fermentation, in which plasmid-containing *E. coli* cells are grown at a reduced temperature during part of the fed-batch phase, during which growth rate is restricted, followed by a temperature up-shift and continued growth at elevated temperature in order to accumulate plasmid; the temperature shift at restricted growth rate improves yield and purity of plasmid (FIG. 4).

This process takes advantage of the temperature sensitivity of high copy number plasmids. In the preferred process, the initial temperature setpoint is 30° C., at which the plasmid is maintained stably at low levels while biomass can accumulate efficiently. During this period, the specific growth rate is controlled at approximately $\mu=0.12$ $h^{-1}$ by an exponential feeding strategy. Induction of plasmid accumulation is performed when the cell density is in the range of 25-60 $OD_{600}$ by shifting the temperature to 42° C. and continued exponential nutrient feeding for up to 15 hours.

After induction of plasmid production at 42° C., the cells are harvested. Typically, the fermentor is cooled directly to around 15° C. prior to harvest. It was unexpectedly found that a hold at 25° C. post plasmid production prior to cooling to around 15° C. for cell harvest improved plasmid yield (Table 1) and quality since the percentage of nicked plasmid was reduced after the hold (FIG. 5; sample 41 is after a 2 hr 25° C. hold). Improved yields are seen when the hold is performed at 30° C. rather than 25° C. and from 0.5 hr to >3 hr holds at 25° C. (Table 1). Analysis of total cellular DNA (plasmid and genomic) from before and after the hold did not reveal the loss of any specific plasmid isoforms during the hold. Although the basis for the yield improvement is unknown, without restricting the application of the embodiments of the invention the inventors speculate that the improved yield is the result of completion of replication of plasmid replication intermediates, and the improved quality due to providing an opportunity for DNA polymerase I and DNA ligase to remove replication primers and seal and supercoil the plasmid. Holding cells prior to harvest at a temperature that does not support extensive plasmid replication while allowing plasmid repair improves yields and quality. It is likely, due to reduced enzyme activity at low temperature, that longer hold periods will be required at reduced temperatures, such as 15° C., than are needed at 25° C. for maximal yield improvement.

Note that this example also demonstrates differences in yield from different plasmid backbones, with the pNTCUltra vectors surprisingly yielding approximately twice the production yield of the gWiz derived plasmid (Genlantis, San Diego Calif.). Although the basis for the yield improvement is unknown, without restricting the application of the invention embodiments, we speculate that one possibility is that the improved yield is the result of increased leading strand primer transcription. As a result, the pNTCUltra backbone may have maximized RNAII promoter dependent replication priming using by using the pUC origin in an optimal orientation relative to other DNA vaccine plasmid components.

competent cells, competent cells were made and transformed according to the manufacturers instructions (Zymo Research). LB media was added to the transformed competent cells after ½ hr incubation on ice and the cells incubated for 1 hr outgrowth in a shaker incubator. Incubations (post transformation shaking and post plating incubation) were

TABLE 1

Process hold step post 42° C. increases plasmid yield

| Run ID # | Host | Plasmid+ | Induction T = 0 $OD_{600}$ | Induction Time | Induction end T = E $OD_{600}$ | Post induction hold | Specific Yield T = E (mg/L/ $OD_{600}$) | Specific Yield T = E + hold (mg/L/ $OD_{600}$) | Specific yield increase (hold) (mg/L/ $OD_{600}$) |
|---|---|---|---|---|---|---|---|---|---|
| RF41 | DH5α | pNTCUltra1 | 32 | 15 | 80 (lysis†) | 2 hrs 25° C. | 15.7 | 16.3 | 0.6 |
| RF36 | DH5α | pNTCUltra1 | 40 | 11 | 93 | 1 hr 25° C. | 13.9 | 16.2 | 2.3 |
| RF48 | DH5α | pNTCUltra1 | 40 | 14 | 98 | 1 hr 25° C. | 14.7 | 16.9 | 2.2 |
| RF73 | DH5α | pNTCUltra1 | 49 | 12.5 | 104 | 1 hr 25° C. | 16.0 | 20.4 | 4.4 |
| RF96 | DH5α | pNTCUltra2 | 44 | 12 | 102 | 1 hr 25° C. | 15.5 | 21.2 | 4.7 |
| RF47 | DH5α | gWiz-D | 52 | 8 | 86 | 1 hr 25° C. | 8.4 | 9.6 | 1.2 |
| RF6A | DH5α | gWiz-D | 39 | 8.5 | 85 | 1 hr 10° C. | 8.7 | 8.4 | −0.3 |
| LS-01016 | DH5α | gWiz-D | 54 | 7 | 97 | 0.5 hr 10° C. | 8.6 | 8.5 | −0.1 |
| RF84+++ | DH5α SpoT- | pNTCUltra1 | 38 | 12 | 95 | 1 hr 25° C. | 12.8 | 16.7 | 3.9 |
| RF8+++ | DH5α TopA- | pNTCUltra1 | 38 | 12 | 78 | 1 hr 25° C. | 15.6 | 18.8 | 3.2 |
| RF67+++ | DH5α + zwf | pNTCUltra1 | 31 | 14 | 76 | 1 hr 30° C. | 14.9 | 16.3 | 1.4 |
| RF33 | DH5α | pNTCUltra3 | 41 | 11.5 | 87 | 3 hrs 25° C. | 14.0 | 17.5 | 3.5 |

+All plasmids contain pUC origin. pNTCUltra1-3 have different backbones and antigen genes. gWiz-D = gWiz derived.
†Loss of ≥5 $OD_{600}$ from the previous time point.
+++DH5α host strains derivatized with a SpoT mutation (decreases stringent response), TopA mutation (removes DNA endonucleaase) or overexpressing zwf gene products, respectively.

Example 2

Seed Stock Process Optimization

Creation of seed stocks from transformations performed at 30° C., rather than 37° C., unexpectedly increased plasmid yield, productivity and seed stock viability.

Transformations were performed using either Z competent cells (Zymo Research, Orange Calif.) or electrocompetent cells using standard methodologies. Briefly, electrocompetent cells (in 10% glycerol) were electroporated with pDNA [one of three kanamycin resistant pNTCUltra DNA Vaccine plasmids containing influenza hemagglutinin (HA) genes from H1, H3 or H5 serotypes] using the BioRad (Hercules, Calif.) micropulser electroporator per manufacturers instructions (2.5 kV, 25 uF, 100Ω, 0.1 cm cuvette, 25 μL cells) and cells transferred to 0.5 mL SOC media in a falcon 10 tube. Transformed cells were outgrown by shaking 1 hr, and then plated onto Luria-Bertani (LB)+kanamycin plates. For Z performed at either 30° C. or 37° C. Seed stocks were created from saturated cultures grown in LB media at either 30° C. or 37° C.

Shake flask and fermentation plasmid yields (performed as described in Example 1) for seed banks of the pNTCUltra influenza DNA vaccine plasmids manufactured at either 30° C. or 37° C. are summarized in Table 2. The minipreps at 30° C. and 37° C. were grown from the seed stock immediately after manufacture. Glycerol stock viability was determined after >1 week at −80° C. storage. The high yielding H5 construct is insensitive to temperature, while plasmids with the H1 and H3 inserts have higher yields and seed stock viability after creation of cryopreserved seed stocks at 30° C. rather than 37° C. No yield differences were observed between seed stocks made with Z competent or electrocompetent cells.

TABLE 2

Seed stock preparation

| pNTCUltra Plasmid antigen | Seed stock preparation | Specific yield in 30° C. miniprep (mg/L/$OD_{600}$) | Specific yield in 37° C. miniprep (mg/L/$OD_{600}$) | Glycerol stock viable | Fermentation yield |
|---|---|---|---|---|---|
| H1 influenza | 30° C. | 1.4 | 1.3 | Yes | 252 mg/L |
|  | 37° C. | 2.0 | 2.5 | No | Inviable cell line |
| H3 influenza | 30° C. | 1.27 | 3.7 | Yes | 570 mg/L |
|  | 37° C. | 1.59 | 0.67 | No | Inviable cell line |

TABLE 2-continued

Seed stock preparation

| pNTCUltra Plasmid antigen | Seed stock preparation | Specific yield in 30° C. miniprep (mg/L/OD$_{600}$) | Specific yield in 37° C. miniprep (mg/L/OD$_{600}$) | Glycerol stock viable | Fermentation yield |
|---|---|---|---|---|---|
| H5 influenza | 30° C. | 1.5 | 9.8 | Yes | 1,290 mg/L |
|  | 37° C. | 1.7 | 10.4 | Yes | 1,260 mg/L |

The surprising observation of increased plasmid yield and viability of seed stocks transformed and manufactured at low temperature is not taught in the art. Application of this embodiment of the invention solved the problem of obtaining manufacturing cell lines for "difficult plasmids' and resulted in successful production of 3/3 plasmids compared to only 1/3 using standard transformation at 37° C. as taught in the art.

Several cell lines have been developed to improve stability of inherently unstable plasmids through reduction in plasmid copy number. For example, the ABLE C and ABLE K strains (Stratagene, La Jolla Calif.) utilize E. coli DNA polymerase I mutation while the GBE180 cell line (DH5α-pcnB) utilizes the E. coli pcnB mutation to lower pMB1 or ColE1 origin plasmid copy number (Pierson V L, Barcak G J. 1999, Focus 21:18-19). The copycutter EPI400 cell line (Epicentre Technologies, Madison Wis.) contains an inducible pcnB mutation to lower pMB1 or ColE1 origin plasmid copy number during transformation and propagation, and optionally inducing copy number via induction of pcnB expression (Haskins D. 2004 *Epicentre Forum* 11: 5-6). However, the authors teach the use of these cells lines for production of inherently unstable plasmids, not stable plasmids. As well, these cell lines are not optimal for plasmid production, since the alteration of the cell line either permanently reduces copy number (ABLE and DH5α-pcnB) or requires a copy number inducer (EPI400).

It is known in the art that reducing copy number will help stability and improve yield of expression plasmids that produce a toxic protein. For example, Hershberger C L, Rosteck Jr P R. 1992 European Patent EP0493926 discloses various strain or plasmid modification methods to lower the copy number of an expression vector plasmid, thereby stabilizing the expression vector to improve production yield of the encoded heterologous polypeptide. In a recent review, Saida F, Uzan M, Odaert B, Bontems F. 2006, *Current Protein and Peptide Science* 7: 47-56 summarize various approaches to reduce plasmid copy number to improve expression of toxic genes in *E. coli*. These authors do not contemplate using reduced temperature to lower the copy number. Many of these strategies require either strain or vector modifications that permanently reduce copy number, or alter the vector sequences. Such approaches are not acceptable for high yield production of existing DNA vaccine plasmids. As well, DNA vaccine plasmids are not designed to contain *E. coli* expressed genes, so production of a toxic product should not be expected. Therefore, a investigator skilled in the art would not apply these approaches to DNA vaccine plasmids.

Joshi A, Jeang K T, 1993. *Biotechniques* 14:883 teach that unstable HIV-1 proviral genomes can be stabilized by transformation at 30° C. compared to 37° C. This instability is probably due to recombination between the two long terminal repeats in the vectors. The authors do not teach that transformation at 30° C. improves plasmid yield, or improves stability of non-repetitive plasmids. The Stb12 and Stb14 cell lines were developed to improve stability of unstable insert (retroviral long terminal repeats or direct repeats) containing vectors. The manufacturer (Invitrogen, Carlsbad Calif.) indicates these cell lines must be transformed at 30° C. rather than 37° C. for maximum performance (Trinh T, Jessee J, Bloom F R. Hirsch V. 1994 *Focus* 16:78-80). The authors do not teach that transformation at 30° C. improves plasmid yield, or improve stability of non-repetitive plasmids.

As indicated above, the DNA vaccine plasmids tested in Table 2 are eukaryotic expression vectors, and are not designed to express encoded genes in *E. coli*. To confirm this, a version of the vector backbone with EGFP rather than influenza HA was created, and transformed into DH5α cells. Cultures containing the plasmids were grown at 37° C. until saturated, the cells pelleted and washed 2× with PBS, and clarified cell lysates made by sonication of the cells in TE buffer (this buffer is compatible with EGFP). No detectable EGFP was present in cell lysates, compared to control cell lines without the plasmid, as quantifiable using a FLX800 microplate fluorescence reader with samples in black 96 well assay plates. The assay was repeated using lysates from electrotransformed cells that were outgrown by shaking either 1 hr at 37° C. or 2 hr at 30° C. and stored at 4° C. to allow EGFP maturation prior to lysate preparation. No detectable EGFP was detected in the cell lysates. This demonstrates that the improvement in yield at 30° C. compared to 37° C. is not due to a transient or constitutive burst of antigen expression after transformation or growth at 37° C. As well, the vectors are non-repetitive and do not contain direct repeats or long terminal repeats. Therefore, the surprising observation of improved yield (and viability) of these non-expressed, non-repetitive plasmids from seed stocks created at 30° C., rather than 37° C., is not taught in the art described above. Other applications of these embodiments of the invention can be determined by an investigator skilled in the art. For example, application of low temperature seed stock growth to seed stock creation for defined media fermentation may eliminate the costly and time consuming step of extensive prescreening of colonies to identify rare high producing plasmids (Prather K L J, Edmonds M C, Herod J W. 2006 *Appl Microbiol Biotechnol* 73:815-826; Chartrain, M., Bentley, L. K., Krulewicz, B. A., Listner, K. M., Sun, W., Lee, C. B 2005 World Patent Application WO2005078115).

Example 3

Endolysin Strain Engineering

DH5α strains containing integrated inducible endolysin genes were constructed using chromosome engineering. Methods for chromosome engineering (insertion or deletion of genes) are well known in the art, for example, lambda red gam recombination (Murphy KC 1998 J. Bact. 180: 2063-2071; Datsenko K A, Wanner B L. 2000 *Proc. Natl. Acad. Sci.* (USA).; 97:6640-6645). Alternatively, replication incompetent plasmids can be site specifically integrated into the genome at bacteriophage attachment sites utilizing bacteriophage recombinase expressing plasmids. Plasmid kits, to allow integration at various bacteriophage attachment sites have been developed (Haldimann and Wanner J. *Bacteriol.* 2001: 6384-6393) and are generally available (*E. coli* genetic stock center, Yale N H). These methods are included herein by reference. For example, integration of a gene at the bacteriophage HK022 attachment site requires cloning a gene to be expressed into a modified integration plasmid such as pAH144 (FIG. 6). This plasmid contains the R6K conditional replication origin (which requires engineered pir+ host cells such as BW23474 for propagation; the R6K origin is non functional in DH5α) a multiple cloning site, a streptomycinR and spectinomycinR resistance marker (spec/strep) and the lambda attachment site.

pAH144 was modified herein to allow expression of cloned genes from the pR promoter (pR and C1857ts lambda repressor included on the plasmid such that gene expression is repressed at 30° C. but induced at 37-42° C.). The gene of interest was cloned under the control of this promoter.

pAH144 Heat Inducible Endolysin Vectors:

Vectors were made by standard restriction digestion mediated transfer of fragments between vectors. All cloning was performed in the BW23474 cell line with selection on spec/strep. All clones were sequence verified.

pAH144-Lambda C1857tsrepressor-PR PL (=pAH144-Lambda repressor)

The pND213 (Love C A, Lilley P E, Dixon N E 1996 *Gene* 176:49-53) native stuffer protein expression vector was digested with BamHI/PstI and the smaller fragment (2724, 1345) containing the phage lambda C1857ts lambda repressor, PR and PL promoters upstream of a multiple cloning site was purified. pAH144 (*E. coli* genetic stock center, Yale N H) was digested with BamHIH/PstI and the linear vector (2.45 kb) purified. The two fragments were ligated and transformed into the BW23474 cell line. pAH144-Lambda repressor (FIG. 6) recombinants were selected on spec/strep at 35 ug/mL each, and confirmed by restriction digestion and sequencing with RgnB-f and tL3-r primers (Haldimann and Wanner *Supra.* 2001).

pAH144-Lambda Repressor-zwf

Insert genes were made by polymerase chain reaction (PCR) amplification from gDNA, using primers that incorporated restriction sites to be compatible with the NcoI and EcoRI cloning sites in pAH144-lambda Repressor parent vector (FIG. 6). This was accomplished using the actual restriction enzymes, or, in cases where these sites were present internally in the PCR fragments, by digestion with AarI type IIS enzyme. The 5' end of the primer contains 4-6 bases, then the AarI site, 4 bases, then the 4 by sticky end of the NcoI or EcoRI enzyme. Cleavage of the PCR product with AarI (Fermentas, Vilnius, Lithuania) cleaves after +4 and +8 (bottom strand) to generate a 4 by sticky end. Methods for use of AarI in cloning are disclosed in Williams, *Supra,* 2006 and are included herein by reference.

To make the pAH144 lambda repressor zwf construct, the *E. coli* zwf gene (Genbank M55005, region spanning the ATG start codon to the stop codon) was PCR amplified from DH5α gDNA and digested to generate NcoI EcoRI fragment and cloned into NcoI/EcoRI compatible pAH 144-Lambda Repressor (prepared as two fragments; NotI/NcoI: 2777, 619, 437 and EcoRI/NotI: 2820, 1013). The 3 fragment ligation with zwf fragment and two bolded vector fragments was transformed into the BW23474 cell line and selected on spec/strep and sequence verified (pAH144-Lambda Repressor-zwf).

(SEQ ID NO: 1)
pAH 144-Lambda Repressor zwf-lambdaR=pAH144-zwf-lambdaR=pAH144-zwf-λR For multiple cistron vectors, a polycistronic linker was included after the zwf gene to create the pAH144-lambda repressor-Zwf bicistron compatible vector. To make the pAH144 lambda repressor zwf-lambdaR construct (FIG. 6), the lambdaR endolysin gene (Genbank J02459 by 45493-45969) was PCR amplified from purified lambda DASH II DNA (Stratagene, La Jolla Calif.) with primers that created flanking NdeI-EcoRI sites. The restriction digested fragment was cloned into NdeUEcoRI cleaved pAH144-lambda repressor-Zwf vector and confirmed by sequencing. The bicistronic linker between zwf and lambdaR has the following sequence.

(SEQ ID NO: 2)
Zwf gene-lambdaR endolysin gene linker
Zwf gene-TAActcgAGGAGATATACATATG LambdaR endolysin gene—EcoRI TAA is Zwf stop codon, AGGA is second cistron RBS, ATG is lambdaR start codon, CTCGAG is XhoI, CATATG is NdeI pAH144-zwf-t4 Gene e-lambdaR The T4 gene e endolysin gene was cloned upstream of lambdaR endolysin gene (downstream of zwf) as a 3 cistron system in pAH144. This allows heat induction of endolysin (both lambda and T4) during production of the plasmid, potentially making more endolysin protein by having two endolysin genes.

pAH144-zwf-lambdaR was digested with XhoI and NdeI and the 5750 by linear vector fragment purified. The T4 gene e gene (Genbank AF158101.6 by 66997-66503) was PCR amplified from T4 gDNA [American Type Culture Collection (ATCC) Manassas Va.] using primers that created XhoI and NdeI sites for cloning, and ribosome binding sites before and after gene e (to allow expression of gene e from the upstream RBS, and lambdaR from the downstream RBS. The 0.53 kb PCR product was XhoI/NdeI digested, and cloned into the vector fragment. The ligation was transformed into BW23474 and recombinants selected with spec/strep. The clone was confirmed by sequencing.

An investigator skilled in the art of cloning can make overexpression vectors for other phage endolysins, lysozymes or autolysins using the strategies and vectors described above.

Transformation of DH5α containing the pAH69 helper with the pAH144 derivative plasmid to be integrated (i.e. pAH144-zwf-lambdaR and pAH144-zwf-T4 gene e-lambdaR) results in integration of the pAH144 plasmid into the genome at the phage HK022 attachment site; recombinants were selected with spec/strep and integration verified using PCR as described in Haldimann and Wanner *Supra.* 2001.

Integration into other phage attachment sites, using pR or pAra modified integration plasmids may be performed as described in Haldimann and Wanner *Supra.* 2001, by modifying the relevant CRIM plasmids, as described herein.

Arabinose Inducible Endolysin Cell Lines (araB-lambdaR):

For comparison purposes, a DH5α strain that contains arabinose inducible lambdaR endolysin (DH5α AraC λR) was created by genome mass transfer (copending application Williams US patent application US60931890) of gDNA from the XJa strain (Zymo Research, Seattle Wash.), a JM109 derivative with lambda R endolysin integrated into the arabinose locus (Jia et al, *Supra* 2006).

Example 4

Endolysin Strain Fermentation

Plasmid DNA (pNTCUltra plasmids) production fermentations with DH5α, and integrated endolysin expressing strains DH5α-pAH144-zwf-lambdaR or DH5α-pAH144-zwf-T4 gene e-lambdaR cell lines, were performed using the inducible fermentation process of Carnes and Williams, Supra, 2006. Endolysin activity was determined using a simple STET buffer lysis assay. Briefly, 15 $OD_{600}$ of cells were pelleted and resuspended in 1 mL of ice cold STET buffer containing 2% Triton X-100. The time for the cells to lyse was determined by observation of culture clearing and is a measurement of relative endolysin activity. As summarized in Table 3, strongly autolytic cells were produced using a cell line with a single integrated copy of the pAH144 lambda repressor zwf-lambdaR plasmid. Surprisingly, endolysin expression (time for autolysis) with pAH144 lambda repressor zwf-lambdaR was dramatically improved compared to arabinose inducible DH5α AraC λR. Combination of lambdaR and T4 gene e (pAH144-zwf-T4 gene e-λR) resulted in even more potent autolysis. The pAH144 lambda repressor zwf-lambdaR cell line is non toxic, and glycerol stocks maintained in this cell line show no loss of viability or fermentation productivity after storage at –80° C. For example, RF135 is a repeat of the same cell line as RF101, after storage of the glycerol stock 9 months at –80° C. As well, no reduction of plasmid yield or integrity, compared to the DH5α parent, was observed in fermentation production with this cell line.

Example 5

Heat Inducible Endolysin Cell Line NTC3012

For production of a wide variety of potential plasmids, it is preferable that the host strain not have integrated plasmid replication origins in the chromosome (e.g. R6K). The pAH144-zwf-λR plasmid was amplified by PCR to delete the R6K replication origin, ligated to form a circle, and integrated into the phage HK022 attachment site in DH5α using the pAH69 plasmid as described in Example 4 and below.

The pAH144-zwf-λR plasmid (FIG. 6) was PCR amplified to delete the R6K replication origin using the following primers.

(SEQ ID NO: 3)
R6KdF01:

cgtgag<u>cacctgc</u>aactGTGTtgaactgctgatcttcagatcctctac (SEQ ID NO: 4)
R6KdR01:

ctccag<u>cacctgc</u>ttttACACAggaacacttaacggctgacatg

The 5.3 kb linear product was DpnI digested (to eliminate parent plasmid), AarI digested (to create compatible sticky ends for ligation), purified, and ligated (to make exonuclease resistant circles for integration). The ligation was electroporated into pAH69 HK022 integration plasmid containing DH5α cell line and colonies were selected with spec/strep.

TABLE 3

Autolysis using Endolysin expressing cell lines

| Run ID # | Production strain | Strain Description | Induction++ $OD_{600}$ | Induction time (hours) | Specific Yield (mg/L/ $OD_{600}$) | Volumetric Yield (mg/L) | Autolysis† |
|---|---|---|---|---|---|---|---|
| RF41 | DH5α | Control | 32 (42° C.) | 15 | 16.3 | 1200 | |
| RF48 | | | 40 (42° C.) | 14 | 16.9 | 1690 | |
| RF73 | | | 49 (42° C.) | 12.5 | 20.4 | 2040 | |
| RF70 | DH5α-AraC λR | arabinose inducible endolysin (0.2% arabinose induction) | 28 (42° C. plasmid) 64 (AraC-λR = 9 hr post 42° C.) | 12 | 13.4 | 900 | Yes (15 min lysis) |
| RF90 | | | 41 (42° C. plasmid) 109 (AraC-λR = 11 hr post 42° C.) | 11 | 11.8 | 1390 | Weak (2 hr lysis) |
| RF91 | DH5α pAH144-zwf-λR | Heat inducible zwf-endolysin cassette | 44 (42° C. shift) | 11 | 13.3 | 1608 | Yes (2 min lysis) |
| RF101 | DH5α pAH144-zwf-λR | Heat inducible zwf-endolysin cassette | 45 (42° C. shift) | 10 | 14.6 | 1746 | Yes (5 min lysis) |
| RF135 | DH5α pAH144-zwf-λR | Heat inducible zwf-endolysin cassette | 50 (42° C. shift) | 10.5 | 18.0 | 2050 | Yes (5 min lysis) |
| RF94 | DH5α pAH144-zwf-T4 gene e-λR | Heat inducible zwf-dual endolysin cassette | 43 (42° C. shift) | 11 | 11.0 | 665 | Yes (0.5 min lysis) |

†At harvest using STET assay. A typical non-autolytic DH5α fermentation requires >8 hrs to clear in this assay. Autolysis of AraC-λR during 30° C. growth restriction phase prior to induction was observed (13 min lysis).
++Plasmid induction at 42° C. is coincident with endolysin induction with heat inducible pAH144 host strains. For DH5α-AraC λR, plasmid induction at 42° C. is independent of endolysin induction (arabinose addition).

The cell line (NTC3012) was confirmed with PCR using P1-P4 primers as described (Haldimann and Wanner *Supra.* 2001); these primer sites are retained in the amplified minicircle vector.

The correct integration was confirmed by PCR analysis of the 3 cell lines [DH5α parent and two autolytic cell lines; NTC3012 PCR product cell line and DH5α pAH144-zwf-λR plasmid integration cell line (Example 4)] using the primer pairs below.

```
R6K PCR product
R6KF01: GGCTTCTCAGTGCGTTACATC      (SEQ ID NO: 5)

R6KR01: ctaaaccctcatggctaacgtact   (SEQ ID NO: 6)
```

These primers amplify the R6K replication origin region of the pAH144 plasmid removed in the PCR product. As expected, no product was observed in the PCR integrated cell line NTC3012 or DH5α, and a 230 by product was observed with the DH5α pAH144-zwf-λR plasmid integrated cell line.

```
    Flanking R6K PCR product
                                    (SEQ ID NO: 7)
    R6KF02:

gtcagccgttaagtgttcctg (overlaps R6KDR01 primer)

(SEQ ID NO: 8)
    R6KR02: caagatccggccacgatgcg
```

These primers amplify the region flanking the R6K origin that is present in both the plasmid and the PCR product. As expected, a 78 by product was detected in the NTC3012 cell line, a 419 by product in the DH5α pAH144-zwf-λR plasmid integrated cell line, and no product in DH5α. This confirms that the NTC3012 cell line has a specifically integrated PCR product without the R6K origin.

The pAH69 helper plasmid was eliminated, and master and working cell banks of the autolysis cell line created. The cell line has been transformed with several different pNTCultra plasmids and fermented in the NTC inducible fermentation process of Carnes and Williams, *Supra,* 2006. As expected, the cell line performs identically (growth rate, viability, plasmid yield and autolytic activity) to the pAH144-zwf-λR plasmid integrated cell line and the parent DH5α cell lines (for growth rate, viability, and plasmid yield). This demonstrates that deletion of the R6K origin does not adversely affect the autolytic activity of the cell line after integration, and that the integrated endolysin has no effect on plasmid production compared to endolysin free DH5α.

A key advantage of the heat inducible NTC3012 cell line is that it requires no inducer (e.g. arabinose) or process modification when used in the NTC inducible fermentation process. An additional unexpected advantage of NTC3012 is that endolysin expression was better repressed in the absence of inducer (i.e. at 30° C. during the growth phase) than in comparable arabinose controlled endolysin cell lines (DH5α-AraC λR). The art teaches that the arabinose promoter is more tightly regulated than the pR or pL heat inducible promoters (Guzman L M, Belin D, Carson M J, Beckwith J. 1995. *J. Bacteriol.* 177: 4121-4130). However, while no endolysin activity was detected prior to heat induction with the NTC3012 zwf-lambdaR cell line (>8 hrs autolysis), the DH5α AraC λR demonstrated detectable endolysin prior to the 42° C. heat shift in the absence of the arabinose inducer (13 minute autolysis immediately prior to temperature shift in RF90, Table 3). This may be due to unexpected leakiness of the arabinose promoter under growth restricted conditions.

Example 6

Autolysis with STET Buffer

Cell paste harvested from shake flask cultures of autolytic cell line (DH5α pAH144-zwf-T4 gene e-λR; see Example 4) harboring the pNTCUltral plasmid was resuspended to a density of approximately 30 $OD_{600}$ with STET buffer. Lysis occurred within 5 minutes of resuspension due to autolysis, and was marked by a visual clearing of the suspension and increase in viscosity. Cell paste from a culture of a non-autolytic cell line, *E. coli* DH5α, was also resuspended to approximately 30 $OD_{600}$ with STET buffer and two 5 mL aliquots were made. Two thousand five hundred (2500) units of Ready-Lyse™ Lysozyme (Epicentre) was added to one 5 mL aliquot of the non-autolytic, DH5α suspension.

All suspensions were allowed to age 30 minutes at room temperature (20-25° C.). The suspension of autolytic cells became the most visually clear. The suspension of DH5α with added lysozyme became somewhat more clear and viscous. No cell lysis was observed in the DH5α suspension to which no lysozyme had been added. FIG. 7 shows the three STET cell suspension aliquots after aging 30 minutes at room temperature. The tube on the left shows the 30 $OD_{600}$ STET suspension with non-autolytic DH5α. The tube in the middle shows the 30 $OD_{600}$ STET suspension with non-autolytic DH5α to which 2500 units Ready-Lyse™ Lysozyme (Epicentre, Madison Wis.) was added. The tube on the right shows the 30 $OD_{600}$ STET suspension of cell line DH5α pAH144-zwf-T4 gene e-λR pNTCUltral, which lysed efficiently without addition of lysozyme. This demonstrates that endolysin can substitute for lysozyme in a STET/lysozyme process.

Example 7

Effect of the Composition of Lysis Solution Containing Glucose and/or Triton X-100 and EDTA Cell paste from an lambdaR autolytic fermentation was resuspended at a concentration of 10 mL buffer per gram (g) wet cell weight (WCW) with 50 mM Tris pH 8.5 buffer containing varying amounts of Triton X-100 (0.04% or 2.0%), EDTA (1 mM or 50 mM), and glucose (0% or 8%); the full factorial was used, giving 8 different buffer compositions. The resuspended cells all lysed by autolysis and were incubated at 37° C. for 35 minutes, then centrifuged at 13000 g for 10 minutes. One (1) mL of supernatant from each of the 8 lysates was heated to 68° C. for 30 minutes, then centrifuged at 13000 g for 10 minutes. Equal volume samples from each lysate were analyzed by agarose gel electrophoresis (FIG. 8). The best plasmid quality was obtained with the combination of 8% glucose and 50 mM EDTA.

Example 8

Autolysis with Solution Containing PEG and Different Amounts of NaCl

Five cell paste samples of 0.3-0.5 g WCW from a lambdaR autolytic fermentation were each resuspended with a different lysis solution at 10 mL per g WCW. The lysis solutions all contained 7.5% PEG-8000, 50 mM Tris pH 8.0, 10 mM EDTA, and 1% Triton X-100. The difference in the lysis solutions was the concentration of NaCl, which had a range of 0 M-0.4 M NaCl. Each of the 5 cell suspensions underwent autolysis and was aged for 40 minutes at room temperature. Then, 0.5 mL samples were centrifuged at 13000 g for 10 minutes to pellet the insoluble material and give a clear supernatant. The supernatants were recovered from the pelleted material. The pelleted material from the autolysis containing 0.4M NaCl was resuspended and extracted with 0.5 mL of TE buffer, and then pelleted again by centrifugation; the clear supernatant was recovered. Samples from the clear autolysis and TE extraction supernatants were pre-stained with SYBR Green II and analyzed by agarose gel electrophoresis (FIG. 9).

This example shows that in a lysis buffer containing approximately 7.5% PEG-8000, increasing concentrations of NaCl reduce the solubility of DNA. FIG. 9 shows that the supercoiled pDNA is solubilized in autolysis with the solution containing up to 0.2M NaCl. The plasmid is not solubilized in autolysis when the solution contains 0.3M or greater NaCl. Lanes 2, 3, and 4 in FIG. 9 show decreasing amounts of higher molecular weight DNA, such as gDNA, while the pDNA remains soluble as the NaCl concentration increases from 0M, to 0.2 M. Thus, a selective solubilization of pDNA was achieved. Neither the gDNA nor the pDNA was solubilized when the autolysis solution contained 0.3 M or 0.4 M NaCl, as shown by the absence of plasmid or gDNA bands in lanes 5, 6, and 7 of FIG. 9. In these samples the RNA remained soluble. The supernatant from the autolysis that did not contain any NaCl was much more viscous than the autolysis supernatants that contained NaCl.

To further show that the plasmid was not solubilized in an autolysis solution containing 7.5% PEG-8000, 50 mM Tris pH 8.0, 10 mM EDTA, 1% Triton X-100, and 0.4M NaCl, the pellet of insoluble material obtained from this autolysis after centrifuging was resuspended in 0.5 mL TE buffer to dissolve the DNA. The DNA solubilized from the pellet is shown by Lane 8 in FIG. 9.

Example 9

Composition of a Lysis Solution in which pDNA is Selectively Soluble

The following solution is useful for performing autolysis or lysozyme lysis and is referred to herein as "PNL buffer".

| | | |
|---|---|---|
| | PEG-8000 | 7.5% |
| | EDTA | 10 mM |
| | Tris | 50 mM |
| | NaCl | 0.15 M |
| | pH 8 | |

Host cell gDNA, cell debris, and other impurities are largely insoluble in this solution. However, pDNA is soluble in this solution. The insoluble gDNA and other insoluble host cell impurities may be removed by solid-liquid separation, such as settling, centrifugation, or filtration. Addition of small quantities of detergent or surfactant aids lysis (e.g. 0.02-5% Triton X-100 or SDS).

Example 10

Preparation of Clarified Lysate by Autolysis in PNL Buffer for pDNA Recovery

Approximately 40 g WCW of cell paste from an autolytic E. coli host strain fermentation (cell line DH5α pAH144-zwf-T4 gene e-λR/pNTCUltra1 plasmid) had a plasmid content of approximately 122 mg pDNA. The cell paste was thoroughly suspended with 520 mL of PNL buffer as described in Example 9 Composition of a lysis solution in which pDNA is selectively soluble. Approximately 1.3 mL of 20% Triton X-100 was added to the suspension and mixed well, and then allowed to stand still at room temperature. Within 15 minutes, autolysis had occurred and insoluble impurities (e.g. including gDNA and cell debris) separated from the liquid lysate and floated. This insoluble material was removed by pouring the lysate through two layers of Miracloth and filtration through a 0.2 μm polyethersulfone capsule filter. Approximately 500 mL of clarified lysate containing the pDNA was obtained by this process.

Example 11

Figure 10:
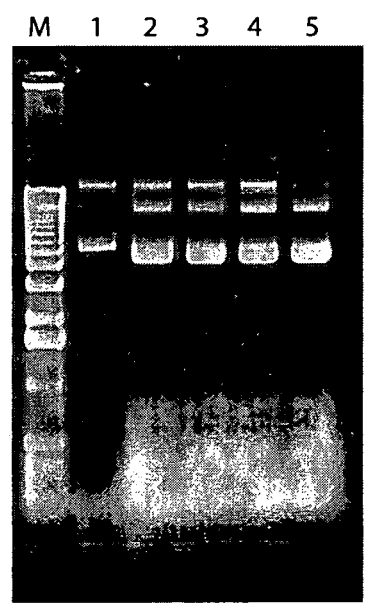

Preparation of Clarified Lysate by Autolysis in PNL Buffer with SDS and $Ca^{2+}$ for pDNA Recovery Approximately 109 g WCW of cell paste (RF91) from an autolytic E. coli host strain was thoroughly suspended with 1.4 L of PNL buffer composed as described in Example 9: Composition of a lysis solution in which pDNA is selectively soluble. Throughout this autolysis process, 0.5 mL samples were taken and centrifuged to obtain a clear lysate for agarose gel electrophoresis analysis. One (1) μL from each sample was run on agarose gel electrophoresis, and the gel was post-stained with SYBR Green II. The cell suspension was mixed with a motor driven impeller for 30 minutes to insure complete resuspension (FIG. 10, lane 1). Seven (7) mL of 20% SDS was added to the suspension and mixing continued for 60 minutes at room temperature. FIG. 10, lanes 2 and 3 show the lysate samples after 30 minutes and for the full 60 minutes, respectively, and it can be seen that pDNA release was complete after 30 minutes. Then, 3.36 mL of 5M $CaCl_2$ was slowly added with continuous mixing (FIG. 10, lane 4). The mixture still appeared somewhat viscous, and another 0.14 mL of 5M $CaCl_2$ was added, and a decrease in the amount of the highest molecular weight DNA is clear in FIG. 10, lane 5, without any significant plasmid loss. The viscosity of this autolysis mixture dropped and mixing was stopped. The autolysis mixture was allowed to stand still at room temperature. After 50 minutes, the insoluble material settled to the bottom of the container. The autolysis mixture was clarified by centrifuging for 20 minutes at 12000 g, followed by filtration through a 0.2 μm polyethersulfone capsule filter. Approximately 1.3 L of clarified lysate containing the pDNA was recovered.

Example 12

Preparation of Clarified Lysate by Lysozyme Lysis in PNL Buffer for pDNA Recovery Lysozyme can be substituted for endolysin for use with PNL buffer in preparing a clarified lysate as described below. An investigator skilled in the art would add approximately 13 volumes of PNL buffer per g WCW of cell paste from a non-autolytic E. coli host strain such as DH5α and thoroughly suspended the cells as described in Example 9: Composition of a lysis solution in which pDNA is selectively soluble). Recombinant lysozyme is added to a final concentration as determined by one skilled in the art. Triton X-100 is added to the suspension and mixed well, and then allowed to stand still at room temperature. The mixture is incubated for lysis to occur and insoluble impurities (e.g. including gDNA

Example 13

Purification of pDNA from a Clarified Lysate Produced by Autolysis with PNL Buffer Approximately 111 g WCW of cell paste was harvested from 450 mL of a fermentation (RF91) with an autolytic *E. coli* host strain. This cell paste had a plasmid content of approximately 724 mg pDNA. The cell paste was thoroughly suspended with 1.4 L of PNL buffer (described in Example 9: Composition of a lysis solution in which pDNA is selectively soluble). Seven (7) mL of 20% Triton X-100 was added to the suspension and mixed well, and then allowed to stand still at room temperature. Autolysis occurred, and the insoluble material was separated from the liquid lysate by centrifugation and 0.2 μm filtration. Approximately 1.4 L of clarified lysate containing the pDNA was recovered. Approximately 2.8 L of 0.675 M NaCl was mixed with the clarified lysate, to make a final NaCl concentration of 0.5M NaCl. Approximately 105 mL of 20% Triton X-100 was added to make a final Triton X-100 concentration of about 0.5%. This lysate solution was chilled in an ice water bath for 30 minutes. Then the mixture was pumped through a Pall Mustang™ Q anion exchange membrane capsule with a 60 mL membrane bed volume. The anion exchange capsule was then washed with 5.3 L of 0.6M NaCl, 25 mM Tris, 1 mM EDTA, pH 8.0. The plasmid was eluted from the anion exchange capsule with 794 mL of a solution containing 1M NaCl, 25 mM Tris, 1 mM EDTA, pH 8.0. The plasmid concentration of the elution pool was 0.564 mg/L and the absorbance ratio $A_{260}$ nm/$A_{280}$ nm was 1.88. A total of 447 mg of purified pDNA was recovered by this process, which is a 62% yield.

Example 14

Purification of pDNA Using Autolysis and Filter Membranes

Plasmid DNA from 260 mL of clarified lysate, prepared as described in Example 10: Preparation of clarified lysate by autolysis in PNL buffer for pDNA recovery, was purified by a non-chromatographic method. Approximately 15.6 mL of 5 M NaCl was mixed with the 260 mL of clarified lysate, making a final NaCl concentration of 0.42 M. The pDNA became insoluble and precipitated, which was observed visually by the hazy appearance of the mixture.

This precipitation mixture was slowly pumped through a Whatman 0.2 μm Polycap 36TC polyethersulfone filter capsule. The entire volume was pumped through the filter capsule and the filtrate was clear (i.e. the haze was removed). Then, a mixture of 100 mL of PNL buffer and 6 mL of 5 M NaCl, in which plasmid is not soluble, was pumped through the filter capsule as a wash. Pumping was continued until the liquid in the filter capsule was removed as much as possible. The filter capsule was then filled with TE buffer pH 8.0, in which pDNA is soluble. The TE buffer was slowly pumped through the filter capsule and the TE filtrate was collected. Two separate 5 mL fractions were collected first, followed by a third 75 mL fraction. Samples of the clarified lysate, filtrate after plasmid precipitation, wash filtrate, and the three TE filtrate fractions were analyzed by agarose gel electrophoresis. As shown in FIG. 11 the plasmid was precipitated by the addition of NaCl to 0.42 M to the clarified PNL buffer lysate. This precipitated pDNA was removed by filtration, and was then recovered by dissolving in TE buffer as the TE buffer was pumped through the filter. As shown by FIG. 11, the pDNA was present in the second 5 mL TE filtrate fraction and in the 75 mL TE filtrate fraction. The DNA concentration and absorbance ratio $A_{260\ nm}/A_{280\ nm}$ of these two fractions was:

| Second 5 mL fraction: | 0.41 mg/mL | $A_{260\ nm}/A_{280\ nm}$ = 1.8 |
| 75 mL fraction: | 0.36 mg/mL | $A_{260\ nm}/A_{280\ nm}$ = 1.8 |

Thus, a total of 29 mg of plasmid was recovered in this non-chromatographic method. RNA removal was achieved since the RNA stayed in solution and was removed in the filtrate as the precipitated pDNA was retained on the filter membrane.

Example 15

Purification of pDNA by Autolysis and Cross Flow Filtration

Approximately 20 g WCW of autolytic cell paste (RF91) was resuspended with 260 mL of PNL buffer (described in Example 9: Composition of a lysis solution in which pDNA is selectively soluble). After complete resuspension, Triton X-100 was added to a final concentration of 0.1%. Autolysis occurred rapidly. The lysate was centrifuged to remove the insoluble material. The supernatant was recovered and heated to 65° C. for 20 minutes, which caused the lysate to become very turbid due to the precipitation of proteins. The precipitated material was then removed by centrifugation and filtration. Approximately 200 mL of clear lysate was recovered.

This lysate was buffer exchanged and concentrated by TFF with a 300 kD molecular weight cut-off polyethersulfone membrane cassette with medium screen channels. The membrane area was 0.2 ft². A trans-membrane pressure (TMP) of 15 psig was maintained. The filtrate was recirculated back to the feed for the initial 20 minutes. Then, diafiltration with TE buffer pH 8.0+1% Triton X-100 was started. The total diafiltration volume was 1000 mL. Then, the retentate plasmid pool was concentrated to 100 mL, followed by diafiltration with 400 mL of TE buffer pH 8.0. Finally, the retentate plasmid pool was concentrated to a final volume of 63 mL, which had a plasmid concentration of 1.34 mg/mL. Concentration and buffer exchange of plasmid lysates can significantly increase plasmid binding capacity of subsequent chromatography steps.

Example 16

Purification of pDNA by Autolysis and a Non-Chromatographic Process

Seven (7) g WCW of autolytic cell paste was resuspended with 200 mL PNL buffer plus 1% Triton X-100 (described in Example 9: Composition of a lysis solution in which pDNA is selectively soluble). Autolysis occurred, and then the lysate was centrifuged to remove the insoluble material. The lysate was then heated to 65° C. for 30 minutes, which caused the lysate to become very turbid due to protein precipitation. The precipitated material was removed by centrifugation, and the clear lysate was pooled into a clean bottle. Then, 10 mL of 5 M NaCl was mixed with the lysate to precipitate the pDNA, and this was chilled on ice for 10 minutes. The precipitated pDNA was pelleted by centrifugation at 12000 g for 20 minutes. The supernatant contained the soluble RNA and was removed. The pDNA was dissolved in 200 mL of 50 mM Tris pH 8.0. Hydrated calcium silicate was added to the pDNA solution to a final concentration of 20 g/L. This mixture was kept suspended by rocking for about 13 hours at room temperature. The hydrated calcium silicate was then removed by 0.4μ filtration. The pDNA was precipitated by addition of 24 mL 3M sodium acetate pH 5.2 and 171 mL of 2-propanol. The precipitation was chilled for 10 minutes and then centrifuged for 30 minutes at 12000 g to pellet the pDNA. The DNA pellet was washed with 70% ethanol and then air dried for 5 minutes. Finally, the pDNA was dissolved with 10 mL of TE buffer pH 8.0. This pDNA solution had a plasmid concentration of 0.58 mg/mL and an absorbance ratio $A_{260\,nm}/A_{280\,nm}$ of 1.89. The plasmid yield from this process was approximately 48%. Samples from this process were analyzed by agarose gel electrophoresis (FIG. 12).

Example 17

PEG Autolysis Process with Selective Precipitations for gDNA, Protein, and RNA Removal 1. Resuspend with PEG-NaCl Lysis buffer (PNL buffer)
   50 mM Tris
   10 mM EDTA
   7.5% PEG8000
   0.15M NaCl
   TritonX-100
   pH 8.5
2. After autolysis remove insoluble material which contains host gDNA, cell debris, and other host cell impurities.
3. Heat lysate to 65° C. to 75° C. to precipitate protein, remove precipitated material.
4. Add sufficient NaCl to cause precipitation of pDNA while leaving RNA in solution, preferably to a final concentration greater than 0.3M, more preferably to about 0.4M NaCl. Recover precipitated plasmid.

Example 18

Extraction of Plasmid from Fermentation Cells; Evaluation of Methods Described in the Art Cells from a non-autolytic pDNA fermentation were utilized without freeze thaw to evaluate the chemical extraction methods of Baker and Taylor, *Supra*, 2003. Extraction was performed as described in Baker and Taylor, *Supra*, 2003. Five (5) OD-units of cells were resuspended to 100 $OD_{600}$ in either: 1) water; 2) 10 mM Tris 1 mM EDTA, pH 8.0 (TE buffer); 3) 10 mM Tris, 10 mM EDTA, pH 8.0; or 4) 1% Triton X-100. All extracts were incubated at 37° C. for 10 min. No plasmid release was observed under any of these conditions, while RNA and gDNA were released. RNA was released to a higher level with 10 mM Tris, 10 mM EDTA pH 8.0, but no RNA was released with Triton X-100. This demonstrates that the art (Baker and Taylor, *Supra*, 2003) which teaches how to extract plasmid from shake flask cells with low ionic strength buffers is not effective with plasmid fermentation cells.

Cells from a second non-autolytic pDNA fermentation were utilized with a single freeze thaw to further evaluate chemical extraction methods of Baker and Taylor, *Supra*, 2003 and to test the conditions for nucleic acid extraction described by Clark and Kacian, *Supra*, 1998. Induced cells were from fermentation cells after plasmid induction (i.e. after growth at 42° C.) and were 78 $OD_{600}$/mL, 741 mg plasmid/L (9.5 mg plasmid/$OD_{600}$/L). Uninduced cells were from fermentation cells at 30° C. before temperature shift and were 55 $OD_{600}$/mL, 93.5 mg plasmid/L, 1.7 mg plasmid/$OD_{600}$/mL. Extractions were performed on 5 $OD_{600}$ of cells resuspended to 50 $OD_{600}$/mL with: 1) water; 2) TE; 3) 7.4 mM HEPES 7.4, 0.7% Triton X-100, 10 mM EDTA; 4) 7.4 mM HEPES 7.4, 0.7% Triton X-100, 10 mM EDTA+1% SDS; 5) 10 mM Tris, 10 mM EDTA, pH 9.3. Extracts were incubated at 37° C., 65° C., or 80° C. All SDS containing samples lysed under these conditions. No significant plasmid release was observed in unlysed samples. gDNA was released at 65° C. and 80° C. treatment. With uninduced cells, gDNA was release with water, TE and Triton X-100/EDTA at 65° C. and 80° C., but not at 37° C. With induced cells, only Triton X-100/EDTA at 65° C. and 80° C. released gDNA. Coomassie stained SDS-PAGE gels of 80° C. samples reveals protein release with water, TE and Triton/EDTA with uninduced samples, and only Triton X-100/EDTA released protein with induced samples.

This demonstrates fermentation grown cells are generally resistant to DNA and protein extraction. This also demonstrates that the art which teaches nonlytic DNA extraction with 7.4 mM Hepes, pH 7.4, 0.7% Triton X-100, 10 mM EDTA (Clark and Kacian, *Supra*, 1998) does not extract pDNA from plasmid fermentation cells, while the chemical extraction methods of Baker and Taylor, *Supra*, 2003 also do not release plasmid from plasmid fermentation cells.

Example 19

Non Lytic Chemical Extraction of Plasmid

Non lytic chemical extraction of proteins has been reported, using a variety of solutions (Choe WS, and Middelberg APJ. 2001 *Biotechnol Bioeng*. 75: 451-455). The feasibility of such extraction methods for plasmid release has not been evaluated.

Extraction of DNA from uninduced high copy fermentation cells (Example 18) was performed using Novagen bugbuster reagent (Novagen, Madison Wis.) and Pierce B-per reagent (Pierce Rockford Ill.). No lysis was observed after 30 min. After rotation overnight at room temperature, some viscosity increase was observed in both samples. Despite lysis, very little plasmid was extracted.

Extraction of DNA from induced high copy fermentation cells (Example 18) was performed using: 1) 6 M urea 1 mM EDTA pH 3; 2) 4 M urea, 10% sucrose, 1 mM EDTA, 50 mM glycine, pH 9.5; 3) Pellet from 1, resuspended in 8 M urea, 3 mM EDTA; 4) Pellet from 2, resuspended in 0.5% acetic acid, 1% NP40. Uninduced cells were extracted with: 5) 100 mM glycine, pH 3; 6) 50 mM MOPS, 200 mM $MgCl_2$, pH 3. All extractions were for 10 min at room temperature. The suspensions were clarified by centrifugation, Phenol/Chloroform extracted, supernatants precipitated with ethanol, pellets resuspended in TE and DNA and RNA resolved on agarose gels. Nucleic acids were visualized by poststaining with SYBR Green II. Limited plasmid and gDNA extraction was observed with conditions 1 and 2, less extraction with 3 and 6, and no extraction with 4 and 5. Plasmid yield and extraction quality were very low in all conditions.

Urea/EDTA extraction was further evaluated. Induced high copy fermentation cells were washed with PBS and resuspended to 6.5 $OD_{600}$/mL in 8M urea, 3 mM EDTA, 0.1 M Tris, pH 9.2 (Choe and Middelberg, *Supra*, 2001). Nucleic acids were extracted in presence of: 1) no additional additive; 2) 0.25% final Cetyl trimethylammonium bromide (CTAB); 3) 0.1 M $CaCl_2$; 4) 3% PEG 3350; 5) 35 mM spermidine. Samples were rotated overnight at room temperature. Flocculation was observed in sample 2, sample 3 was granular, sample 5 slightly clumpy, samples 1 and 4 were homogeneous. No lysis was observed. The samples were centrifuged (large pellet was observed in sample 2), the supernatants extracted with Phenol/chloroform to remove protein, and samples resolved on an agarose gel. Nucleic acids were visualized by SYBR Green II poststain. Plasmid and gDNA was present in the PBS wash and urea extractions with and without PEG. CTAB and $CaCl_2$ prevented DNA extraction. Plasmid extraction, with less gDNA contamination, was observed in the presence of spermidine. Overall, extracted plasmid yields were low and the released plasmid was heavily contaminated with gDNA.

Extractions were performed on uninduced and induced cells with 8M urea, 3 mM EDTA, 0.1 M Tris, pH 9.2 solution for 1 hr (rather than overnight). Lysis was observed with uninduced cells, and the sample became highly viscous. In induced cells, plasmid extraction was observed after 1 hr, with high amounts of gDNA, but not RNA contamination. The released plasmid was intact but yields and purity were low.

Collectively, these results demonstrate that while analytical amounts of plasmid can be extracted from fermentation cells using a variety of chemical treatments, the yield and purity are low. A method to improve the quality and yield of plasmid extraction is needed.

Example 20

Extraction of Plasmid from Endolysin Containing Cells

Various plasmid extraction methods outlined in Examples 19 and 20 were evaluated with endolysin containing autolytic cells. Surprisingly, plasmid was efficiently extracted from endolysin cells using a variety of conditions, including:
$H_2O$,
1 mM EDTA,
0.1% Triton X-100,
10 mM Tris, (pH 8.0),
50 mM Tris, (pH 8.0),
50 mM Tris, (pH 8.0), 1 mM EDTA,
50 mM Tris, (pH 8.0) 10 mM EDTA
and sucrose containing buffers.

Plasmid extraction was efficient with freshly harvested fermentation cells or frozen cell pellets. This demonstrates that the failure to extract plasmid from fermentation cells utilizing methods described in the art is due to the barrier function of the cell wall, and can be overcome by inclusion of endolysin in the cell cytoplasm.

Example 21

Extraction of pDNA from Endolysin Containing Cells Using Acetate Solutions

In order to manufacture pDNA at large scale, the extraction process ideally should not result in a very viscous mixture. It was surprisingly determined that extraction at acidic pH prevents the mixture from becoming very viscous. Acetate solutions are preferred as buffers in the desired pH range. To evaluate the effect of acetate salt concentration on extraction and mixture properties, 2 g aliquots of frozen autolytic NTC3012 cell paste containing 5.2 mg plasmid per g WCW were resuspended with 20 mL (10 volumes) of solution containing 10 mM EDTA and 0-0.4 M potassium acetate or 0-0.4 M sodium acetate, pH 4.8-4.9; 1 mL aliquots from these cell suspensions were additionally treated with 0.1% Triton X-100 (B samples) or 1% PEG8000 (C samples) (Table 4).

TABLE 4

Extraction of pDNA from endolysin containing cells using acetate solutions

| | A | B | C |
|---|---|---|---|
| 1 | 10 mM EDTA | 1A + 0.1% Triton X-100 | 1A + 1% PEG8000 |
| 2 | 0.1 M potassium acetate, 10 mM EDTA | 2A + 0.1% Triton X-100 | 2A + 1% PEG8000 |
| 3 | 0.2 M potassium acetate, 10 mM EDTA | 3A + 0.1% Triton X-100 | 3A + 1% PEG8000 |
| 4 | 0.3 M potassium acetate, 10 mM EDTA | 4A + 0.1% Triton X-100 | 4A + 1% PEG8000 |
| 5 | 0.4 M potassium acetate, 10 mM EDTA | 5A + 0.1% Triton X-100 | 5A + 1% PEG8000 |
| 6 | 10 mM EDTA | 6A + 0.1% Triton X-100 | 6A + 1% PEG8000 |
| 7 | 0.1 M sodium acetate, 10 mM EDTA | 7A + 0.1% Triton X-100 | 7A + 1% PEG8000 |
| 8 | 0.2 M sodium acetate, 10 mM EDTA | 8A + 0.1% Triton X-100 | 8A + 1% PEG8000 |
| 9 | 0.3 M sodium acetate, 10 mM EDTA | 9A + 0.1% Triton X-100 | 9A + 1% PEG8000 |
| 10 | 0.4 M sodium acetate, 10 mM EDTA | 10A + 0.1% Triton X-100 | 10A + 1% PEG8000 |

All extraction mixtures containing potassium acetate (2-5) or sodium acetate (7-10) were non-viscous. Extractions 1 and 6, which contained no acetate salt, were viscous.

Samples from the A group in Table 4 were centrifuged immediately following resuspension and the supernatant was saved. Then the extraction mixtures were held at room temperature for 2 hours, after which samples were centrifuged to obtain clear supernatant. One (1) µL of each extraction supernatant was run on 1% agarose (FIG. 13). As shown by the gel picture in FIG. 13, plasmid extraction was rapid and did not appear to increase after 2 hours of incubation. Sodium acetate resulted in the best plasmid extraction. The addition of Triton X-100 significantly increased the extraction of plasmid. The highest amount of plasmid was extracted using 0.4 M sodium acetate, 10 mM EDTA, with 0.1% Triton X-100.

Example 22

Effects of pH and Sodium Acetate Concentration

To further evaluate the effect of sodium acetate concentration and pH on plasmid extraction and viscosity, samples of the same frozen cell paste used in Examples 21 were resuspended with 10 volumes of 0.4-1.0 M sodium acetate, 10 mM EDTA, at pH 4.5, 5.0, and 5.5. Triton X-100 was added to 0.1% after resuspension. The pH 4.5 extractions were all non-viscous. At pH 5.0 the extractions were more viscous, and the viscosity increased with increasing sodium acetate concentration. The extractions at pH 5.5 were most viscous. Plasmid release was maximal at pH 5.0 and pH 5.5 (FIG. 14). This example, along with Example 21, shows that plasmid can be efficiently extracted over a wide range of acetate salt concentrations at a slightly acidic pH.

Example 23

Large Scale Plasmid Isolation by Extraction of pDNA from Endolysin Containing Cells Approximately 100 g WCW of frozen cell paste of endolysin containing cells from a fermentation with a specific plasmid yield of approximately 3.1 mg pDNA/g WCW was resuspended with 1000 mL of 0.4 M sodium acetate, 10 mM EDTA, pH 4.8 by vigorous mixing on a stir plate. Triton X-100 was added to a final concentration of 0.1% w/v, and mixing was continued to thoroughly distribute the Triton X-100. The mixture was incubated at 37° C. for 20 minutes. The mixture remains non-viscous and was centrifuged for 25 minutes at 12000 g to remove cells and debris. Approximately 850 mL of supernatant was recovered with a total DNA concentration of 0.32 mg DNA/mL, 96% as pDNA and 4% as gDNA. Thus, the plasmid yield from the extraction was 261 mg pDNA (an 84% step yield).

Example 24

Kit for Extraction of Plasmid from Cells

The requirement for endolysin in the low pH plasmid extraction process of Examples 21-23 was further evaluated as follows. Plasmid was extracted from inducible process fermentation cells from 4 independent cell lines. 1) Plasmid 1, 5.2 kb NTC8382-41H-HA antibiotic free backbone, NTC3016 autolytic cell line [NTC8382-41H-HA is a influenza DNA vaccine plasmid and NTC3016 is a autolytic cell line derived from NTC3012 (Example 5) described in copending application Williams JA, U.S. Patent Application 60/932,160], 2) Plasmid 2, 6.5 kb kanamycin resistant (kanR) pUC origin backbone, DH5α cell line (no endolysin), 3) Plasmid 2, pAH144-zwf-lambdaR integrated cell line (Example 4) 4) Plasmid 3, 22 kb ampicillin resistant (ampR) backbone, pAH144-zwf-lambdaR integrated cell line.

Extraction was performed as follows. Twenty (20) g frozen cell paste was resuspended in 10 volumes (200 mLs) of low pH extraction buffer (30 mM sodium acetate, 50 mM EDTA, 8% sucrose, pH 4.8). Sample A was removed. Triton X100 was added to 0.1%, and Sample B removed after 10 minutes at ambient temperature, and Sample C removed after an additional 20 minutes incubation at 37° C. (typically the cells reach 30° C. in this time). Each sample (1 mL) was clarified by centrifugation, and 1 µL of each supernatant resolved on an agarose gel. Sample D was post centrifugation of the entire 200 mL extraction.

The results are shown in FIG. 15 and demonstrate that endolysin was critical for extraction (no extraction with DH5α cells). The results also demonstrated that low pH extraction releases essentially 100% of 3 different plasmids, and was not limited based on size (plasmid 3 is 22 kb) or backbone (antibiotic free versus kanR or ampR). Variable amounts of plasmid were extracted without Triton X-100.

A followup low pH extraction of inducible fermentation cells from Plasmid 2, 6.5 kb kanR pUC origin backbone, DH5α cell line (no endolysin), was performed, to determine if lysozyme can substitute for endolysin. A control extraction of the same plasmid from the pAH144-zwf-lambdaR integrated cell line (Example 4) was also performed. Approximately 20 g frozen cell paste was resuspended in 10 volumes (200 mL) of low pH extraction buffer (30 mM sodium acetate, 50 mM EDTA, 8% sucrose, pH 4.8). The pH was adjusted to 5.2 with 0.2 M NaOH. Sample A was removed. Three 50 mL samples were removed and treated as follows: Extraction 1; HEWL (Sigma, St Louis Mo.) added to 5000 U/mL. Extraction 2; Ready-Lyse lysozyme (Epicentre, Madison Wis.) added to 1200 U/mL. Extraction 3; Negative control (no lysozyme added). Triton X-100 was added to 0.1%, and the suspension incubated 40 minutes at 37° C. Sample B was then removed from each extraction. (Samples B1, 2, and 3 respectively: for the pAH144-zwf-lambdaR integrated cell line, only B3 was performed). Each sample (0.5 mL) was clarified by centrifugation, and 1 µL of each supernatant resolved on an agarose gel. The results are shown in FIG. 16, and demonstrate that either lysozyme can substitute for endolysin in the low pH extraction process. This is surprising, since HEWL has low activity at this pH range (Jensen and Kleppe, *Supra*, 1972).

The surprising observation that lysozyme can substitute for endolysin in low pH plasmid extraction enables creation of kits for plasmid extraction from general laboratory strains of *E. coli*. While many possible kits can be envisioned, one possible low pH plasmid extraction kit is demonstrated below, linking 'autolyte' extraction buffer with the Qiaprep miniprep spin column kit (Qiagen, Germany).

1. Centrifuge amount of cells expected to contain 10-20 µg of plasmid 1 min in microcentrifuge
2. Resuspend cells in 100 µL autolyte resuspension buffer.†
3. Incubate 5-10 min room temperature.
4. Pellet autolyte extracted cells by centrifuging 0.5-1 mL at about 12000 g for 2-5 min (in a bench top centrifuge).
5. Remove supernatant to fresh tube by pipetting.
6. Add 5 volumes Qiagen Buffer PB and mix.
7. Apply to the QIAprep spin column.
8. Centrifuge for 60 s. Discard the flow-through.
9. Wash QIAprep spin column by adding 0.5 mL Buffer PB and centrifuging for 1 min.
10. Discard the flow through, and wash QIAprep spin column by adding 0.75 mL Buffer PE and centrifuging for 1 min.
11. Discard the flow-through, and centrifuge for an additional 1 min to remove residual wash buffer.
12. Place the QIAprep column in a clean 1.5 mL microcentrifuge tube. To elute DNA, add 50 µl Buffer EB (10 mM Tris, pH 8.5) to the center of each QIAprep spin column, let stand for 1 min, and centrifuge for 1 min.
13. Optionally add another 50 µL Buffer EB to the center of each QIAprep spin column, let stand for 1 min, and centrifuge for 1 min. Performing the elution twice with 50 µL Buffer EB insures complete recovery of pDNA. († e.g. 30 mM sodium acetate, 50 mM EDTA, 8% sucrose, 0.1% Triton X-100, 5000 units/mL lysozyme, 100 µg/mL RNase, pH 5.2; acceptable modifications include 30-400 mM sodium acetate, 0-50 mM EDTA 0-100 µg/mL PEI, pH 4.7-5.5.)

This kit eliminates several steps required for alkaline lysis (P1, P2, N3) resulting in superior speed and flexibility. The purified plasmid is of a high quality, with excellent 260/280 ratio and integrity by gel and low levels of gDNA (due to retention of gDNA in the cell pellets). An investigator skilled in the art can adapt the plasmid extraction method embodiments of the invention to vacuum manifold devices, other spin column devices or other plasmid purification components of commercially available kits.

Example 25

Extraction of Protein from Cells

Low pH extraction was evaluated for utility in protein purification. The NTC3012 endolysin expressing cell line (Example 5) was transformed with pVEX-EGFP and pVEX-AmCyan (pVEX is a standard ampR IPTG inducible bacterial expression plasmid). These plasmids express the indicated fluorescent proteins in the cytoplasm of E. coli after IPTG induction. Fifty (50) mL bacterial cultures were grown in LB media containing ampicillin, and EGFP or AmCyan expression induced by addition of IPTG and subsequent 4 hrs growth at 42° C. (to coinduce endolysin). Five (5) mL samples were resuspended to 5 $OD_{600}$/mL in autolyte buffer (30 mM sodium acetate, 8% sucrose, 50 mM EDTA, 0.1% Triton X-100, pH 5.2) and either extracted (10 min at 37° C.) or sonicated (positive control). The suspensions were centrifuged 2 min in a microcentrifuge. The AmCyan extracted pellet was resuspended in the original volume of 50 mM sodium phosphate 0.3 M NaCl, pH 7.2, and the cells extracted 5 minutes ambient temperature, then repelleted. Release of EGFP or AmCyan in the supernatants was quantified using the FLX800 microplate fluorescence reader with black 96 well assay plates. Integrity was assessed by Coomassie stained SDS-PAGE gel analysis as described in Williams and Hodgson, Supra, 2006). The results are summarized in Table 5. Extraction efficiency superior to sonication was observed for both proteins. AmCyan required a post extraction high salt wash to release the protein from the cell mass; this resulted in a significant purification of the protein in the salt wash. This is not due to AmCyan retention in extracted cells, since the bulk of the protein was associated with the pellet after either sonication or extraction in the low salt extraction buffer (i.e. >3 fold improved yield of extraction 2 compared to sonication). The band profile of general E. coil proteins by SDS-PAGE was similar after extraction or sonication. This demonstrates that most soluble E. coli proteins (and soluble recombinant proteins overexpressed in the cell line) are quantitatively extractable from endolysin containing cells in the low pH extraction buffer, resulting in the benefits of significant purification (removal of cell mass, gDNA) without cell lysis viscosity issues normally associated with gDNA release that occurs with homogenization conditions or chemical extraction. As demonstrated in Example 24, lysozyme can be substituted for endolysin in protein extraction.

TABLE 5

Protein extraction

| Protein | Condition | Fluorescence (FU)+ | % Recovery (standardized to sonication) | Integrity (SDS-PAGE) |
|---|---|---|---|---|
| EGFP | Sonication | 3439 | 100% | Single band |
| EGFP | Extraction | 4660 | 136% | Single band |
| AmCyan | Sonication | 3864 | 100% | None detected |
| AmCyan | Extraction | 99 | 3% | None detected |
| AmCyan | Extraction 2† | 12,619 | 337% | Single band (purified) |

†High salt wash of pellet from extraction + blanked versus buffer (15 fluorescence units = FU).

Example 26

Extraction of Plasmid from Cells Using EDTA, PEI or Combinations

As diagrammed in FIG. 3, extraction of plasmid from cells requires permeabilization of the outer membrane, inner membrane, and cell wall for quantitative plasmid extraction. We have demonstrated the utility of endolysin or lysozyme for permeabilizing the cell wall, and a non ionic detergent (Triton X-100) for inner membrane solubilization, and have demonstrated that plasmid extraction efficiency is reduced in the absence of 1) endolysin or lysozyme, or 2) Triton X-100 (Example 24). Here we investigate the importance of outer membrane permeabilizers in extraction.

A series of 100 g WCW extractions (in 1 L of extraction buffer) using unfrozen NTC8382-41H-HA plasmid containing fermentation cells were performed using a low pH extraction buffer without EDTA (30 mM sodium acetate, 8% sucrose, pH 5.2) or supplemented with 10 mM EDTA (pH 5.05), 50 mM EDTA (pH 4.9) or 50 μg/mL PEI (pH 5.21). After resuspension, sample A was removed, Triton X-100 added to 0.1%, followed by a 10 minute incubation at ambient temperature (Sample B), then 20 minutes in a 37° C. bath (Sample C). The entire 1 L extract was centrifuged to remove cells (Sample D). Plasmid was purified from the sample supernatants using the miniprep kit of Example 24. The results are summarized in Table 6 and surprisingly demonstrated significant amounts of plasmid can be extracted in the absence of EDTA. The cells had not been subjected to a freeze thaw cycle, so the mechanism of outer membrane permeabilization is unknown. Extraction efficiency in low pH extraction buffer without EDTA in cells subjected to a freeze thaw cycle is similar to that in buffers with EDTA.

EDTA chelates $Mg^{++}$ releasing LPS; elimination of EDTA results in less endotoxin release during extraction (Table 6). An alternative outer membrane permeabilizer, PEI, which does not release endotoxin (LPS) increased extraction efficiency without increasing endotoxin levels in the final supernatant. This demonstrates alternative outer membrane permeabilization methods can be utilized to release plasmid, and that significant amounts of plasmid are released without any outer membrane permeabilizer.

TABLE 6

EDTA versus PEI extraction efficiency

| Extraction | Sample | Lysate plasmid concentration (μg/mL) | % recovery (versus 50 mM EDTA) | % gDNA (RT-PCR) | Endotoxin Kunits/mL+ |
|---|---|---|---|---|---|
| 50 mM EDTA (positive control) | A | 14 | 5% | | |
| | B | 81 | 30% | | |
| | C | 221 | 82% | | |
| | D | 270 | 100% | 0.26% | 2,046 |

TABLE 6-continued

EDTA versus PEI extraction efficiency

| Extraction | Sample | Lysate plasmid concentration (µg/mL) | % recovery (versus 50 mM EDTA) | % gDNA (RT-PCR) | Endotoxin Kunits/mL+ |
|---|---|---|---|---|---|
| 10 mM EDTA | A | 11 | 4% | | |
| | B | 59 | 22% | | |
| | C | 134 | 50% | | |
| | D | 155 | 57% | 0% | 4234 |
| 0 mM EDTA | A | 2 | 1% | | |
| | B | 70 | 26% | | |
| | C | 99 | 37% | | |
| | D | 100 | 37% | 0.35% | 740 |
| 0 mM EDTA + 50 ug/mL PEI | A† | 2 | 7% | | |
| | B | 159 | 59% | | |
| | C | 202 | 75% | | |
| | D | 187 | 70% | 0.46% | 467 |

†Before PEI. After PEI addition 5 µg/mL plasmid + Endotoxin units were determined using the EndoSafe PTS system (Charles River Laboratories, Wilmington MA).

The released plasmid was of a very high purity from all four extraction conditions, with <0.5% of the DNA as gDNA in the supernatant. A subsequent 0.1% Triton X-100 extraction from frozen cells in 30 mM sodium acetate, 8% sucrose extraction buffer containing 50 µg/mL PEI and 1 mM EDTA resulted in 98% extraction yield of intact plasmid with 1.6% gDNA. This demonstrates that extraction is highly selective for pDNA versus gDNA extraction. Preparation of plasmid DNA using the miniprep kit of Example 24 after overnight storage of the 0 mM EDTA extract at 4° C. demonstrated no loss of yield or integrity of plasmid. This surprisingly demonstrates that EDTA is not necessary in a low pH extraction buffer to prevent plasmid damage in the extract. This is contrary to the teachings of Baker and Taylor, Supra, 2003, where extracted plasmid was demonstrated to be heavily damaged. While not limiting the application of the embodiments of the invention, this may indicate that endogenous nucleases cannot function at this pH. Consistent with this, EDTA addition is required to prevent plasmid degradation upon pH adjustment of the extract to a higher pH (e.g. pH 8).

Approximately 1 kg WCW of frozen fermentation cell paste was extracted with 10 volumes (10 L) 30 mM Sodium Acetate, 8% sucrose extraction buffer containing 50 µg/mL PEI and 1 mM EDTA resulted in 105% extraction of intact plasmid in the clarified extract, with 1.1% gDNA. The plasmid concentration in the extract was 638 mg/L. This extraction yield was determined by comparison to analytical alkaline lysis (Qiaprep miniprep spin column kit; Qiagen, Germany). In the analytical assay, plasmid in 10 µL of fermentation harvest sample (containing approximately 2 mg WCW cells) are lysed with 250 µL P1, 250 µL P2 and 350 µL N3 (425 volumes total per volume WCW) and purified and eluted in 2×50 µL elutions as per kit instructions. Lysis at such dilute cell concentration is a high yield analytical method; large scale alkaline lysis yields at more reasonable extraction volumes (40 volumes total, including P1, P2, and P3/N3, per volume WCW) are typically about 50% of this theoretical yield. This demonstrates, at the multigram scale, that low pH extraction is significantly improved relative to alkaline lysis; yields are much higher, in approximately ¼ the total volume, with low gDNA in the extract.

Hoare et al, Supra 2006 report that diatomaceous earth does not bind plasmid at pH 7-10, and can be used as a filter aid in plasmid processing in this pH range. The compatibility of the low pH extraction process with body feed filtration with diatomaceous earth was established. No plasmid loss after treatment of a 30 mM Sodium acetate, 8% sucrose, 50 mM EDTA, 0.1% triton X-100 extract (pH 5.3) with 40 g/L diatomaceous earth (Celite 503, J T Baker, Phillipsburg N.J.) was observed.

Example 27

Extract Conditioning with Anionic Surfactants and Alkaline Earth Metal Salts

Both the autolysis process and the low pH extraction process release plasmid DNA, protein, RNA, LPS, and phospholipids from the cell. Optionally, the extract or lysate can be conditioned to remove one or more of these components. For example, for protein purification, plasmid DNA could be precipitated by addition of PEI (at higher concentrations than is used to permeabilize the cell). Gehart and Daignault, Supra, disclose various methods of conditioning low pH homogenates to remove debris and nucleic acids. These methods could also be applied to the low pH extraction embodiments of the invention, and are included herein by reference.

For plasmid DNA purification, the released protein, RNA, LPS, and phospholipids components are impurities. We disclose herein a method of conditioning lysates or extracts to remove one or more of these components by treatment of the lysate with an anionic surfactant and sequential precipitation with a cationic component (synthetic anionic detergents). Preferably, the anionic detergent component interacts with lysate or extract components, then the anionic detergent-lysate component complex is precipitated by addition of the cationic component. Preferably the cationic component is an alkaline earth metal. Various synthetic anionic detergents and calcium surfactants are reviewed in Zapf A, Beck R, Platz G, Hoffmann H.2003. Advances Colloid and Interface Science 100-102:349-380 and Rodriguez C H, Lowery L H, Scamehorn J F, Harwell J H 2001 Journal Surfactants Detergents 4: 1-14 and Rodriguez C H, Chinanasathien C, Scamehron J F, Saiwan C, Chavadej S. 1998 Journal Surfactants Detergents 1: 321-328 and are included herein by reference. While not limiting the application of the invention embodiments, a preferred surfactant-alkaline earth metal precipitate is formed by sequential SDS-Calcium treatment to form calcium dodecyl sulphate. Other cations than $CaCl_2$ also form soaps with anionic surfactants; some are described in Jian-xiao LV, Dong W, Ji-ti Z. J 2006 Dispersion Science and Technology 27: 1073-1077 and are included herein by reference.

We disclose herein application of anionic surfactants to condition extracts or lysates for plasmid purification by removal of impurities. We disclose that addition of an anionic surfactant such as SDS, followed by addition of a cation such as $Ca^{2+}$, forms insoluble flocculated complexes with the SDS, protein, lipopolysaccharides, and other host cell impurities (calcium dodecyl sulfate complexes) while leaving the pDNA in solution. The complexes can then be removed by solid-liquid separation.

The following example demonstrates that formation of surfactant-alkaline earth metal precipitates can be used to remove protein or endotoxin from plasmid containing cell extracts. A centrifuged extract prepared as described in Example 26 (870 g WCW cell paste and 8.7 L extraction buffer=30 mM sodium acetate, 8% sucrose, 1 mM EDTA, 50 µg/mL PEI buffer 0.1% Triton X-100 pH 5.0, after the extraction, pH 5.46) was conditioned with SDS-Calcium as follows. SDS was added to 0.2%, and the extract heated to 69° C. and cooled at which time $CaCl_2$ was added to 14 mM final concentration and the extract held overnight. The extract was centrifuged to remove the calcium dodecyl sulfate complexes. The conditioned extract contained 106 KEU/mL and 0.27 mg/mL protein (6.6 mg/mL protein prior to treatment) with no plasmid loss. SDS-Calcium treatment of extracts typically reduces endotoxin levels to 50-100 KEU/mL. This is a 5-40 fold reduction in endotoxin compared to unconditioned extracts (Table 6). SDS-Calcium treatment will also remove protein and endotoxin at lower temperatures (i.e. with no heating step after SDS addition prior to Calcium addition, or with an optional cooling step). As well, different concentrations can be used, for example 0.4% SDS and 28 mM $CaCl_2$. An investigator skilled in the art can determine alternative SDS-Calcium treatments wherein SDS-Calcium removes protein and endotoxin without plasmid loss as well as alternative anionic surfactant or cationic components.

The application of anionic surfactant-alkaline earth metal treatments to condition lysates or extracts for plasmid purification has not been taught in the art. Coffman J L, Shpritzer R I Vicik S M. 2007 World Patent Application WO2007035283 disclose flocculation to remove contaminants in protein solutions using combinations of cationic and anionic salts. The application of anionic surfactant-alkaline earth metal treatments to flocculate or condition cell extracts or lysates is not contemplated by the inventors. Anionic and cationic salts such as SDS precipitated with ammonium have been utilized to flocculate and remove contaminants from soil DNA isolates (Brolaski M N, Venugopal R J, Stolow D. 2006 World Patent Application WO2006073472) but the inventors did not contemplate use of these salts for other applications. SDS precipitation with high concentrations (1-4 M) ammonium or potassium salts is generally utilized in alkaline lysis to precipitate impurities and prepare clarified lysates for plasmid processing. In alkaline lysis, SDS-debris complexes are precipitated at final concentrations of 1-4 M ammonium or potassium acetate which dramatically increases lysate volumes and cost. The application of low concentrations of anionic surfactants and alkaline earth metal salts disclosed herein to flocculate or condition preexisting cell extracts or lysates has not been reported.

The following demonstrates that in addition to removal of endotoxin and protein, SDS-Calcium treatment can unexpectedly be utilized to remove RNA. Approximately 40-50 mL aliquots of a 1 L (100 g WCW cells extracted with 1 L extraction buffer) centrifuged extract prepared as described in Example 26 (extraction buffer=30 mM sodium acetate, 8% sucrose, 1 mM EDTA, 50 µg/mL PEI buffer 0.1% Triton X-100 pH 5.0, extract pH 5.7) were conditioned with SDS-Calcium under various pH, temperature and salt conditions. After adjustment of the pH and salt concentration, SDS was added to 0.2%, and the extract heated to the target temperature at which time $CaCl_2$ was added to 14 mM final concentration and the extract heated at temperature a further 10 minutes, followed by cooling to room temperature. Aliquots were electrophoresed on a gel, and analyzed for RNA by SYBR Green II prestain and plasmid by SYBR Green I prestain. Plasmid yields were quantified using the kit of Example 24. The results are shown in Table 7 and demonstrate novel removal of RNA using SDS-Calcium and heat treatment. RNA removal with SDS-Calcium heat treatment is robust and does not precipitate plasmid DNA. An investigator skilled in the art can determine alternative buffer compositions wherein SDS-Calcium heat treatment removes RNA without plasmid loss. Eon-Duval A; Gumbs K and Ellett C 2003 *Biotechnol Bioeng* 83: 544-553 disclose use of high salt concentration (>0.5 M $CaCl_2$) to precipitate RNA from alkaline lysates without plasmid loss. Bhikhabhai R, 1999 European Patent EP0964923 disclose use of high salt concentration (0.2 M $CaCl_2$) to precipitate RNA from alkaline lysates. Detraz NJF, Rigaut G. 2006 World Patent Application WO2006060282 disclose use of 0.2 M $CaCl_2$ to precipitation RNA and endotoxin. Collectively, the art teaches that RNA or endotoxin precipitation with $CaCl_2$ occurs only at high salt concentration (>0.2 M $CaCl_2$). Thus, while $CaCl_2$ precipitation of RNA at high concentrations (0.2 to 1 M) of $CaCl_2$ is taught in the art, RNA removal at low concentrations (e.g. 14 mM $CaCl_2$) using SDS-Calcium with heating is an unexpected observation that is not taught in the art.

TABLE 7

SDS-Calcium conditioning of a plasmid extract to remove RNA

| pH | Temperature (° C.) | NaCl | RNA removal** | % recovery plasmid† |
|---|---|---|---|---|
| 5.7 (no SDS/Ca) | Room temp | Not added | – | 100% (untreated) |
| 5.5 | 60 | Not added | – | |
| | 65 | | + | |
| | 70 | | + | |
| 5.7 | 65 | Not Added | – | 91% |
| | | 0.05 M | – | |
| | | 0.1 M | – | |
| | | 0.2 M | +/– | |
| | | 0.3 M | +/– | |
| | | 0.4 M | + | 98% |
| | | 0.5 M | + | 95% |
| | | 0.6 M | + | 97% |
| 6.0 | 60 | Not added | – | |
| | 65 | | +/– | |
| | 70 | | + | |
| 6.5 | 60 | Not Added | – | |
| | 65 | | – | |
| | 70 | | + | |
| 6.0 | 60 | 0.6 M | + | |
| | 65 | | + | |
| | 70 | | + | |

†Versus untreated, first line.
**– = no RNA removed, +/– = partial RNA removal, and + = removal of high molecular weight RNA band as revealed by agarose gel electrophoresis in the presence of Sybrll stain.

Example 28

Improved Solid Liquid Separation by Thermal Flocculation of an Autolytic Extraction Mixture Acid Extraction—Thermal Flocculation Fifty (50) g WCW of autolytic cell paste from a plasmid fermentation (specific plasmid yield=4.6 mg pDNA/g WCW)

was mixed with 20 volumes (20 L/kg WCW) of Extraction Buffer (30 mM sodium acetate, 10 mM EDTA, 8% sucrose, pH 5.2), and stirred for 20 minutes to ensure complete resuspension. This cell suspension was treated with 0.1% Triton X-100 and stirred for 10 more minutes to allow complete release of the plasmid DNA into solution. This extraction mixture was not viscous. A 1 mL analytical sample at this point was centrifuged for 5 minutes at 17,000 RCF to pellet the solids; analysis of the supernatant at this point confirmed complete pDNA release.

The lysate prepared above was passed through a heat exchange apparatus consisting of a first stainless steel coil immersed in a 70° C. water bath followed by a second stainless steel coil immersed in an ice water bath. The flow rate was set such that the residence time, τ, in each coil was 20 sec. The cooled lysate exiting the heat exchangers was collected in a bottle. The lysate remained non-viscous, and, surprisingly, much of the cell debris had flocculated and quickly began to settle. The lysate was stored for about 16 hours at 4° C. FIG. 17 A shows the resulting lysate, with the settled flocculated cell debris. Approximately 80% of the original volume was recovered after separation of the flocculated material by filtration through two layers of Miracloth (Calbiochem).

pH 8 Heat Lysis Process

Autolytic cell paste from the same plasmid fermentation was also prepared similarly to the continuous heat lysis method described by Zhu et al, *Supra*, 2005, which describes a lysozyme/heat lysis process at pH 8.0. Approximately 50 g WCW of cell paste was resuspended in 20 volumes (about 20 $OD_{600}$) of TE buffer (10 mM Tris, 50 mM EDTA, pH 8.0), and stirred for 10 minutes to completely resuspend the cells. Then the cell suspension was adjusted to 0.1M NaCl and 2% Triton X-100 (lysozyme was not added since this cell paste contained endolysin). After the 20 minute incubation, the cell suspension was very viscous. It was given the same thermal treatment described in the above paragraph by pumping through the heat exchanger apparatus, and was collected in a bottle. This method did not result in any separation of cell debris by flocculation or sedimentation. This lysate was still slightly viscous. As shown in FIG. 17 B, after 16 hours, the cell debris remained suspended throughout the entire volume.

DNA concentration from both lysates was quantified using the kit of Example 28; the amount of gDNA was quantified by RT-PCR. One (I) mL samples from before and after the thermal treatments were briefly centrifuged to obtain clear samples for testing. The results are shown in Table 8.

TABLE 8

| | Thermal treatment | | | |
|---|---|---|---|---|
| Sample | | DNA concentration | % pDNA | % gDNA |
| Acid Extraction | Before thermal treatment | 0.227 mg/mL | 98.8% | 1.2% |
| | After thermal treatment | 0.228 mg/mL | 99.0% | 1.0% |
| pH 8 heat lysis | Before thermal treatment | 0.220 mg/mL | 92.5% | 7.5% |
| | After thermal treatment | 0.244 mg/mL | 72.3% | 27.7% |

This example demonstrates the new and unexpected result of improved flocculation and sedimentation of cell debris, with greatly reduced gDNA contamination, achieved by thermal treatment of a crude extract prepared by the low pH extraction procedure.

Agarose gel analysis of 1 μg samples of DNA from both heat treated lysates is shown in FIG. 18, showing significantly less open circle plasmid and gDNA in the lysate from the low pH extraction process after heat treatment (lane 1), in comparison to the lysate from the pH 8 heat lysis process (lane 2).

Thus, the reader will see that the endolysins and associated production process embodiments of the invention provide compositions and methods for improved plasmid production.

While the above description contains many specifications, these should not be construed as limitations on the invention, but rather as an exemplification of one preferred embodiment thereof. Many other variations are possible. For example Boyd et al, *Supra*, 2006 describes a STET/recombinant lysozyme lysis procedure performed at 20° C. or 37° C., preferably with an additional alkaline pH shift to denature gDNA. Lee and Sagar, *Supra*, 2001 describes a heat lysis method that also requires recombinant lysozyme. A limitation of both heat and lysozyme lysis method is the need for large amounts of recombinant lysozyme. The availability of recombinant lysozyme, needed for efficient recovery from both these processes is an issue for large scale production. Application of an endolysin producing cell line embodiment of the invention to the lysozyme lysis process of Boyd et al, *Supra*, 2006 or heat lysis process of Lee and Sagar, *Supra*, 2001 would eliminate the need for costly recombinant lysozyme.

Accordingly, the scope of the invention should be determined not by the embodiments illustrated, but by the appended claims and their legal equivalents.

We claim:

1. A method for extraction of plasmid DNA from gram negative bacterial cells, comprising the steps of:
   a. introducing at least one gene encoding at least one peptidoglycan hydrolase into said bacterial cells, each bacterial cell having cytoplasm, a cytoplasmic membrane, an outer bacterial membrane, and an inner bacterial membrane;
   b. growing said bacterial cells in the presence of said plasmid;
   c. directing production of said peptidoglycan hydrolase from the introduced gene into the cytoplasm of the cells; and
   d. permeabilizing the cytoplasmic membrane at a slightly acid pH in the range of pH 4.5-6.0,
   whereby said method extracts said plasmid DNA from bacterial cells without complete cellular lysis.

2. The method of claim 1 wherein said peptidoglycan hydrolase is chosen from the group consisting of: bacteriophage lambda gene R product, bacteriophage T4 gene e product, bacteriophage T7 lysozyme, and hen egg white lysozyme.

3. The method of claim 1 wherein said peptidoglycan hydrolase is expressed from a heat inducible promoter, an isopropyl thiogalactopyranoside inducible promoter, or an arabinose inducible promoter.

4. The method of claim 1 wherein said peptidoglycan hydrolase is expressed from the bacterial chromosome or from an extra-chromosomally replicating plasmid.

5. The method of claim 1 wherein said step of permeabilizing the cytoplasmic membrane is performed with a non-ionic detergent.

6. The method of claim 1 including the step of permeabilizing the outer bacterial membrane with a component selected from the group consisting of: chelators, ethylenediamine tetraacetic acid, polyethyleneimine, freeze-thaw process, and combinations thereof.

7. The method of claim 1 further comprising the step of flocculating cell debris after extraction, using flocculating agents selected from the group consisting of: polyethylene glycol, synthetic anionic surfactant flocculating agents, SDS-calcium, polyethyleneimine, neutral flocculants, and combinations thereof or by heat treatment.

8. The method of claim 1 wherein said gram negative bacterial cells are *Escherichia coli*.

9. A method for extraction of plasmid DNA from gram negative bacterial cells, the method comprising:
   a. suspending cells in a solution at a slightly acid pH of approximately pH 4.5-6.0 to form a re-suspension;
   b. permeabilizing a bacterial inner membrane and bacterial outer membrane;
   c. adding peptidoglycan hydrolase; and
   d. incubating the re-suspension to extract said plasmid DNA from said bacterial cells without complete cellular lysis.

10. The method of claim 9 wherein said peptidoglycan hydrolase is selected from the group consisting of: bacteriophage lambda gene R product, bacteriophage T4 gene e product, bacteriophage T7 lysozyme, and hen egg white lysozyme.

11. The method of claim 9 wherein said step of permeabilizing the bacterial inner bacterial membrane is performed with a non-ionic detergent.

12. The method of claim 9 wherein said step of permeabilizing the bacterial outer membrane is performed with a component selected from the group consisting of: chelators, ethylenediamine tetraacetic acid, polyethyleneimine, freeze-thaw process, and combinations thereof.

13. The method of claim 9 further comprising a step of flocculating cell debris after extraction with flocculating agents or with a component selected from the group consisting of: heat treatment, polyethylene glycol, alkaline pH shift, synthetic anionic surfactant flocculating agents, SDS-calcium, polyethyleneimine, and neutral flocculants.

14. The method of claim 9 wherein said gram negative bacterial cells are *Escherichia coli* cells.

* * * * *

SEQUENCE LISTING

```
<160> NUMBER OF SEQ ID NOS: 8

<210> SEQ ID NO 1
<211> LENGTH: 5764
<212> TYPE: DNA
<213> ORGANISM: Artificial Sequence
<220> FEATURE:
<223> OTHER INFORMATION: Description of Artificial Sequence:
      pAH144-zwf-lambdaR

<400> SEQUENCE: 1
ctgcaggtga tgattatcag ccagcagaga ttaaggaaaa cagacaggtt tattgagcgc      60
ttatctttcc ctttattttt gctgcggtaa gtcgcataaa aaccattctt cataattcaa     120
tccatttact atgttatgtt ctgagggag tgaaaattcc cctaattcga tgaagattct     180
tgctcaattg ttatcagcta tgcgccgacc agaacacctt gccgatcagc caaacgtctc     240
```

```
ttcaggccac tgactagcga taactttccc cacaacggaa caactctcat tgcatgggat    300
cattgggtac tgtgggttta gtggttgtaa aaacacctga ccgctatccc tgatcagttt    360
cttgaaggta aactcatcac ccccaagtct ggctatgcag aaatcacctg gctcaacagc    420
ctgctcaggg tcaacgagaa ttaacattcc gtcaggaaag cttggcttgg agcctgttgg    480
tgcggtcatg gaattacctt caacctcaag ccagaatgca gaatcactgg cttttttggt    540
tgtgcttacc catctctccg catcaccttt ggtaaaggtt ctaagcttag gtgagaacat    600
ccctgcctga acatgagaaa aaacagggta ctcatactca cttctaagtg acggctgcat    660
actaaccgct tcatacatct cgtagatttc tctggcgatt gaagggctaa attcttcaac    720
gctaactttg agaattttg caagcaatgc ggcgttataa gcatttaatg cattgatgcc     780
attaaataaa gcaccaacgc ctgactgccc catccccatc ttgtctgcga cagattcctg    840
ggataagcca agttcatttt tctttttttc ataaattgct ttaaggcgac gtgcgtcctc    900
aagctgctct tgtgttaatg gtttcttttt tgtgctcata cgttaaatct atcaccgcaa    960
gggataaata tctaacaccg tgcgtgttga ctatttttacc tctggcggtg ataatggttg   1020
catgtactaa ggaggttgta tggaacaacg cataaccctg aaagattatg caatgcgctt   1080
tgggcaaacc aagacagcta agatctctc acctaccaaa caatgccccc ctgcaaaaaa    1140
taaattcata taaaaaacat acagataacc atctgcggtg ataaattatc tctggcggtg   1200
ttgacataaa taccactggc ggtgatactg agcacatcag caggacgcac tgaccaccat   1260
gaaggtgacg ctcttaaaaa ttaagccctg aagaagggca gcattcaaag cagaaggctt   1320
tggggtgtgt gatacgaaac gaagcattgg gatcctaagg aggtttaatc gacccatggc   1380
ggtaacgcaa acagcccagg cctgtgacct ggtcattttc ggcgcgaaag gcgaccttgc   1440
gcgtcgtaaa ttgctgcctt ccctgtatca actggaaaaa gccggtcagc tcaacccgga   1500
cacccggatt atcggcgtag gcgtgctga ctgggataaa gcggcatata ccaaagttgt    1560
ccgcgaggcg ctcgaaactt tcatgaaaga aaccattgat gaaggtttat gggacaccct   1620
gagtgcacgt ctggattttt gtaatctcga tgtcaatgac actgctgcat tcagccgtct   1680
cggcgcgatg ctggatcaaa aaaatcgtat caccattaac tactttgcca tgccgcccag   1740
cacttttggc gcaatttgca aagggcttgg cgaggcaaaa ctgaatgcta accggcacg    1800
cgtagtcatg gagaaaccgc tggggacgtc gctggcgacc tcgcaggaaa tcaatgatca   1860
ggttggcgaa tacttcgagg agtgccaggt ttaccgtatc gaccactatc ttggtaaaga   1920
aacggtgctg aacctgttgg cgctgcgttt tgctaactcc ctgtttgtga ataactggga   1980
caatcgcacc attgatcatg ttgagattac cgtggcagaa gaagtgggga tcgaagggcg   2040
ctggggctat tttgataaag ccggtcagat gcgcgacatg atccagaacc acctgctgca   2100
aattctttgc atgattgcga tgtctccgcc gtctgacctg agcgcagaca gcatccgcga   2160
tgaaaaagtg aaagtactga agtctctgcg ccgcatcgac cgctccaacg tacgcgaaaa   2220
aaccgtacgc gggcaatata ctgcgggctt cgcccagggc aaaaaagtgc gggatatct    2280
ggaagaagag ggcgcgaaca agagcagcaa tacagaaact tcgtggcga tccgcgtcga    2340
cattgataac tggcgctggg ccggtgtgcc attctacctg cgtactggta acgtctgcc    2400
gaccaaatgt tctgaagtcg tggtctattt caaaacacct gaactgaatc tgtttaaaga   2460
atcgtggcag gatctgccgc agaataaact gactatccgt ctgcaacctg atgaaggcgt   2520
ggatatccag gtactgaata agttcctgg ccttgaccac aaaacataacc tgcaaatcac    2580
caagctggat ctgagctatt cagaaacctt taatcagacg catctggcgg atgcctatga   2640
```

-continued

```
acgtttgctg ctggaaacca tgcgtggtat tcaggcactg tttgtacgtc gcgacgaagt    2700
ggaagaagcc tggaaatggg tagactccat tactgaggcg tgggcgatgg acaatgatgc    2760
gccgaaaccg tatcaggccg gaacctgggg acccgttgcc tcggtggcga tgattacccg    2820
tgatggtcgt tcctggaatg agtttgagta actcgaggag attacatatg gtagaaatca    2880
ataatcaacg taaggcgttc ctcgatatgc tggcgtggtc ggagggaact gataacggac    2940
gtcagaaaac cagaaatcat ggttatgacg tcattgtagg cggagagcta tttactgatt    3000
actccgatca ccctcgcaaa cttgtcacgc taaacccaaa actcaaatca acaggcgccg    3060
gacgctacca gcttctttcc cgttggtggg atgcctaccg caagcagctt ggcctgaaag    3120
acttctctcc gaaaagtcag gacgctgtgg cattgcagca gattaaggag cgtggcgctt    3180
tacctatgat tgatcgtggt gatatccgtc aggcaatcga ccgttgcagc aatatctggg    3240
cttcactgcc gggcgctggt tatggtcagt tcgagcataa ggctgacagc ctgattgcaa    3300
aattcaaaga agcgggcgga acggtcagag agattgatgt atgataagaa ttctcatgtt    3360
tgacagctta tcactgatca gtgaattaat ggcgatgacg catcctcacg ataatatccg    3420
ggtaggcgca atcactttcg tctctactcc gttacaaagc gaggctgggt atttcccggc    3480
ctttctgtta tccgaaatcc actgaaagca cagcggctgg ctgaggagat aaataataaa    3540
cgaggggctg tatgcacaaa gcatcttctg ttgagttaag aacgagtatc gagatggcac    3600
atagccttgc tcaaattgga atcaggtttg tgccaatacc agtagaaaca gacgaagaag    3660
ctagctaatg ctctgtctca ggtcactaat actatctaag tagttgattc atagtgactg    3720
gatatgttgc gttttgtcgc attatgtagt ctatcattta accacagatt agtgtaatgc    3780
gatgattttt aagtgattaa tgttattttg tcatcctta ggtgaataag ttgtatattt    3840
aaaatctctt taattatcag taaattaatg taagtaggtc attattagtc aaaataaaat    3900
catttgtcga tttcaatttt gtcccatggc taattcccat gtcagccgtt aagtgttcct    3960
gtgtcactca aaattgcttt gagaggctct aagggcttct cagtgcgtta catccctggc    4020
ttgttgtcca caaccgttaa accttaaaag ctttaaaagc cttatatatt cttttttttc    4080
ttataaaact taaaaccttaa gaggctattt aagttgctga tttatattaa ttttattgtt    4140
caaacatgag agcttagtac gtgaaacatg agagcttagt acgttagcca tgagagctta    4200
gtacgttagc catgagggtt tagttcgtta aacatgagag cttagtacgt taaacatgag    4260
agcttagtac gtgaaacatg agagcttagt acgtactatc aacaggttga actgctgatc    4320
ttcagatcct ctacgccgga cgcatcgtgg ccggatcttg cggccgctcg gcttgaacga    4380
attgttagac attatttgcc gactaccttg gtgatctcgc ctttcacgta gtggacaaat    4440
tcttccaact gatctgcgcg cgaggccaag cgatcttctt cttgtccaag ataagcctgt    4500
ctagcttcaa gtatgacggg ctgatactgg gccggcaggc gctccattgc ccagtcggca    4560
gcgacatcct tcgcgcgat tttgccggtt actgcgctgt accaaatgcg ggacaacgta    4620
agcactacat ttcgctcatc gccagcccag tcgggcggcg agttccatag cgttaaggtt    4680
tcatttagcg cctcaaatag atcctgttca ggaaccggat caaagagttc ctccgccgct    4740
ggacctacca aggcaacgct atgttctctt gcttttgtca gcaagatagc cagatcaatg    4800
tcgatcgtgg ctggctcgaa gatacctgca agaatgtcat tgcgctgcca ttctccaaat    4860
tgcagttcgc gcttagctgg ataacgccac ggaatgatgt cgtcgtgcac aacaatggtg    4920
acttctacag cgcggagaat ctcgctctct ccaggggaag ccgaagtttc caaaggtcg    4980
```

```
ttgatcaaag ctcgccgcgt tgtttcatca agccttacgg tcaccgtaac cagcaaatca      5040
atatcactgt gtggcttcag gccgccatcc actgcggagc cgtacaaatg tacggccagc      5100
aacgtcggtt cgagatggcg ctcgatgacg ccaactacct ctgatagttg agtcgatact      5160
tcggcgatca ccgcttccct catgatgttt aactttgttt tagggcgact gccctgctgc      5220
gtaacatcgt tgctgctcca taacatcaaa catcgaccca cggcgtaacg cgcttgctgc      5280
ttggatgccc gaggcataga ctgtacccca aaaaaacagt cataacaagc catgaaaacc      5340
gccactgcgc cgttaccacc gctgcgttcg gtcaaggttc tggaccagtt gcgtgagcgc      5400
atacgctact tgcattacag cttacgaacc gaacaggctt atgtccactg gttcgtgcc      5460 ttcatccgta tcgatggccc ccgatggtag tgtggggtct ccccatgcga gagtagggaa      5520
ctgccaggca tcaaataaaa cgaaaggctc agtcgaaaga ctgggccttt cgttttatct      5580
gttgtttgtc ggtgaacgct ctcctgagta ggacaaatcc gccgggagcg atttgaacg      5640 ttgcgaagca acggcccgga gggtggcggg caggacgccc gccataaact gccaggcatc      5700
aaattaagca gaaggccatc ctgacggatg gccttttgc gtggccagtg ccaagcttgc      5760
atgc                                                                  5764

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Zwf
      gene-lambdaR endolysin gene linker

<400> SEQUENCE: 2
taactcgagg agatatacat atg                                              23

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: R6KdF01

<400> SEQUENCE: 3
cgtgagcacc tgcaactgtg ttgaactgct gatcttcaga tcctctac                   48

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: R6KdR01

<400> SEQUENCE: 4
ctccagcacc tgcttttaca caggaacact taacggctga catg                       44

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: R6KF01

<400> SEQUENCE: 5
ggcttctcag tgcgttacat c                                                21

<210> SEQ ID NO 6
```

```
<211> LENGTH: 24
<212> TYPE: DNA
<213> ORGANISM: Artificial Sequence
<220> FEATURE:
<223> OTHER INFORMATION: Description of Artificial Sequence: R6KR01

<400> SEQUENCE: 6 ctaaccctc atggctaacg tact                                           24

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: R6KF02

<400> SEQUENCE: 7
gtcagccgtt aagtgttcct g                                             21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: R6KR02

<400> SEQUENCE: 8
caagatccgg ccacgatgcg                                               20
```